US008263785B2

(12) United States Patent
Anzalone et al.

(10) Patent No.: US 8,263,785 B2
(45) Date of Patent: Sep. 11, 2012

(54) PROCESS FOR THE PREPARATION OF CHYMASE MODULATORS

(75) Inventors: Luigi Anzalone, West Chester, PA (US); Penina Feibush, Ambler, PA (US); Ilias Konstantinos Dorziotis, Somerville, NJ (US); Xun Li, New Hope, PA (US); Frank J. Villani, Perkasie, PA (US)

(73) Assignee: Janssen Pharmaceutica N.V. (BE)

( * ) Notice: Subject to any disclaimer, the term of this patent is extended or adjusted under 35 U.S.C. 154(b) by 373 days.

(21) Appl. No.: 12/608,585

(22) Filed: Oct. 29, 2009

(65) Prior Publication Data

US 2010/0145075 A1 Jun. 10, 2010

Related U.S. Application Data

(60) Provisional application No. 61/197,815, filed on Oct. 29, 2008.

(51) Int. Cl.
*C07D 495/00* (2006.01)
(52) U.S. Cl. ......................................................... 549/5
(58) Field of Classification Search ........................ 549/5
See application file for complete search history.

(56) References Cited

U.S. PATENT DOCUMENTS

| | | |
|---|---|---|
| 7,459,444 B2 | 12/2008 | Hawkins et al. |
| 2005/0043313 A1 | 2/2005 | South et al. |
| 2005/0176769 A1 | 8/2005 | Hawkins et al. |
| 2006/0264673 A1 | 11/2006 | Buchwald et al. |
| 2007/0123504 A1 | 5/2007 | Bolin et al. |

FOREIGN PATENT DOCUMENTS

| | | |
|---|---|---|
| WO | WO 02/085838 A1 | 10/2002 |
| WO | WO 2004/013094 A2 | 2/2004 |
| WO | Wo 2004/013094 A3 | 2/2004 |

OTHER PUBLICATIONS

PCT/US09/62568 International Search Report, dated Jan. 4, 2010.
de Paulis, "Novel Autocrine and Paracrin Loops of the Stem cell Factor / Chymase Network", *Intl. Arch. Allerg. Immunol.*, 1999, pp. 422-425, vol. 118.
Longey, B.J., et al., "Chymase cleavage of stem cell factor yields a bioactive soluble product?", *Proc. Natl. Acad. Sci.*, 1997. pp. 9017-9021, vol. 94.
Chowdhury, S., et al., "The First Example of a Catalytic Hunsdieker Reaction: Synthesis of β-Halostyrenes", *J. Org. Chem.*, 1997, pp. 199-200, vol. 62.
Chunxiang, K., et al., Stereoselective Synthesis of (E)-β-Arylvinyl Halides by Microwave-Induced Hunsdieker Reaction, *Synlett*, 2000, pp. 1439-1442, vol. 10.
Chowdhury, S., et al., "Manganese (II) catalysed Hunsdieker reaction: A facile entry to α-(dibromomethyl) benzenemethanol", *Tet. Lett.*, 1996, pp. 2623-2624, vol. 37, issue 15.
Jiang, et al., "Copper-Catalyzed Coupling of Amides and Carbamates with Vinyl Halides" Organic Letters, 2003, pp. 3667-3669, vol. 5, issue 20.
Ramesh, et al., Transition Metal Catalyzed reactions of Aryl, Vinyl, bifunctional Vinyl Halides and Nitrenes and Their Application the the Synthesis of Lactones, Lactams and Heterocycles. A Thesis submitted to the University of Pune for the Degree of Doctor of Philosophyin Chemistry 2007, p. 30.
Fristad, et. al., Conversion of Alkenenes to 1,2-Diazides and 1,2-Diamines. Journal of Organic Chemistry, 1985, pp. 3647-3649, vol. 50.

*Primary Examiner* — Taofiq A Solola
(74) *Attorney, Agent, or Firm* — Yuriy P. Stercho

(57) ABSTRACT

The present invention is a process for the preparation of chymase modulators, useful in the treatment of inflammatory and serine protease mediated disorders.

19 Claims, No Drawings

PROCESS FOR THE PREPARATION OF CHYMASE MODULATORS

CROSS REFERENCE TO RELATED APPLICATIONS

This application claims the benefit of U.S. Provisional Application No. 61/197,815, filed on Oct. 29, 2008, which is incorporated by reference herein in its entirety.

FIELD OF THE INVENTION

The present invention is a process for the preparation of chymase modulators, useful in the treatment of inflammatory and serine protease mediated disorders.

SUMMARY OF THE INVENTION

The present invention is directed to a process for the preparation of compounds of formula (I)

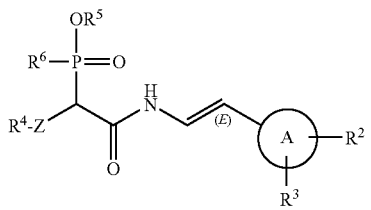

wherein

is independently selected from the group consisting of aryl, heteroaryl, and benzo fused heterocyclyl; optionally substituted with $R^2$ and $R^3$;

$R^2$ is one to three substituents independently selected from the group consisting of methoxy, $C_{2-6}$alkoxy, $NH_2$, $NH(C_{1-6}$alkyl), aryl, heteroaryl, halogen, hydroxy, and nitro;

wherein the $C_{1-4}$alkyl and $C_{2-6}$ alkoxy substituents of $R^2$ are optionally substituted with a substituent independently selected from the group consisting of $-NR^{11}R^{12}$, aryl, heteroaryl, one to three halogens and hydroxy; wherein $R^{11}$ and $R^{12}$ are substituents independently selected from the group consisting of hydrogen, $C_{1-6}$ alkyl, and aryl; wherein the $C_{1-6}$alkyl substituent of $R^{11}$ or $R^{12}$ is optionally substituted with a substituent selected from the group consisting of hydroxy, aryl, $-C(=O)C_{1-4}$alkoxy, and $-NR^{15}R^{16}$;

wherein said $R^{15}$ and $R^{16}$ are substituents independently selected from the group consisting of hydrogen, $C_{1-6}$ alkyl, and aryl, alternatively, $R^{15}$ and $R^{16}$ are taken together with the atoms to which they are attached to form a ring of five to seven members;

$R^3$ is one to three substituents independently selected from the group consisting of $C_{1-6}$alkyl, $C_{2-6}$alkenyl, $C_{1-6}$alkoxy, $-OCH_2(C_{2-6})$alkenyl, $NH_2$, $-NH(C_{1-6}$alkyl), $-N(C_{1-6})$dialkyl, $-NHC(=O)Cy$, $-N(C_{1-6}$alkyl)$C(=O)Cy$, $-C(=O)C_{1-4}$alkoxy, $-C(=O)NR^{17}R^{18}$, $-C(=O)NHcycloalkyl$, $-C(=O)N(C_{1-6}$alkyl)cycloalkyl, $-C(=O)NHCy$, $-C(=O)N(C_{1-6}$alkyl)Cy, $-C(=O)Cy$, $-OC(=O)NR^{19}R^{20}$, halogen, hydroxy, nitro, cyano, aryl, and aryloxy;

wherein alkyl and alkoxy are optionally substituted with one to three substituents independently selected from the group consisting of $-NR^{21}R^{22}$, $-NHcycloalkyl$, $-N(C_{1-6}$alkyl)cycloalkyl, $-NHCy$, $-N(C_{1-6}$alkyl)Cy, aryl, heteroaryl, halogen, $-C(=O)NR^{23}R^{24}$, $-OC(=O)NR^{25}R^{26}$, $-C(=O)(C_{1-4})$alkoxy, and $-C(=O)Cy$; wherein alkenyl is optionally substituted on a terminal carbon with aryl and $-C(=O)NR^{27}R^{28}$; and, wherein aryl and cycloalkyl are optionally substituted with one to three substituents independently selected from $R^{14}$;

each $R^{14}$ is independently hydrogen, $C_{1-6}$alkyl, $C_{1-6}$alkoxy, $C_{2-6}$alkenyl, $C_{1-6}$alkylthio, $-NH_2$, $-NH(C_{1-6})$alkyl, $-N(C_{1-6})$dialkyl, aryl, heteroaryl, aryloxy, heteroaryloxy, halogen, hydroxy, or nitro; wherein any one of the foregoing $C_{1-6}$alkyl- or $C_{1-6}$alkoxy-containing substituents of $R^{14}$ is optionally substituted on a terminal carbon atom with a substituent selected from $-NR^{29}R^{30}$, aryl, heteroaryl, one to three halogen atoms, or hydroxy;

$R^{17}$, $R^{18}$, $R^{19}$, $R^{20}$, $R^{21}$, $R^{22}$, $R^{23}$, $R^{24}$, $R^{25}$ and $R^{26}$ are substituents independently selected from the group consisting of hydrogen, $C_{1-6}$alkyl and aryl; wherein the $C_{1-6}$alkyl and aryl are each optionally substituted with hydroxy, aryl, aryloxy, $-C(=O)$-aryl, $-C(=O)C_{1-4}$alkoxy, $NH_2$, $-NH(C_{1-6}$alkyl), or $-N(C_{1-6})$dialkyl; alternatively, $R^{17}$ and $R^{18}$, $R^{19}$ and $R^{20}$, $R^{21}$ and $R^{22}$, $R^{23}$ and $R^{24}$ or $R^{25}$ and $R^{26}$ are taken together with the atoms to which they are attached to form a ring of five to seven members;

$R^{27}$ and $R^{28}$ are independently hydrogen; $C_{1-6}$alkyl optionally substituted with hydroxy, aryl, $-C(=O)C_{1-4}$alkoxy, $NH_2$, $-NH(C_{1-6}$alkyl) or $-N(C_{1-6})$dialkyl; or aryl; alternatively, $R^{27}$ and $R^{28}$ are taken together with the atoms to which they are attached to form a ring of five to seven members;

$R^{29}$ and $R^{30}$ are independently hydrogen, $C_{1-6}$alkyl optionally substituted with hydroxy, aryl, $-C(=O)C_{1-4}$alkoxy, $NH_2$, $-NH(C_{1-6}$alkyl), or $-N(C_{1-6})$dialkyl; or aryl; alternatively, $R^{29}$ and $R^{30}$ are taken together with the atoms to which they are attached to form a ring of five to seven members;

Cy is a heterocyclyl optionally substituted with a substituent selected from the group consisting of $C_{1-6}$ alkyl, $C_{1-6}$alkylC(=O)$C_{1-6}$alkyl, $-C_{1-6}$alkylC(=O)$C_{1-6}$alkoxy, $C_{1-6}$alkylC(=O)aryl, $-C(=O)(C_{1-6})$alkyl, $-C(=O)(C_{1-6})$alkoxy, $-C(=O)aryl$, $-SO_2aryl$, aryl, heteroaryl, and heterocyclyl; wherein aryl and the aryl portion of the $C_{1-6}$alkylC(=O)aryl, $-C(=O)aryl$ and $-SO_2aryl$ are optionally substituted with one to three substituents independently selected from the group consisting of $C_{1-6}$alkyl, $C_{1-6}$alkoxy, halogen, hydroxy, $NH_2$, $NH(C_{1-6}$alkyl), or $-N(C_{1-6})$dialkyl; and wherein heterocyclyl is optionally substituted with aryl, one to three halogen atoms, or one to three oxo substituents; and, wherein heterocyclyl is optionally spiro-fused to said Cy;

$R^5$ is selected from the group consisting of hydrogen; $C_{1-3}$alkyl optionally substituted with $NH_2$, $-NH(C_{1-6})$alkyl, $C_{1-6}$alkylcarbonyloxy, $C_{1-6}$alkoxycarbonyloxy, $C_{1-6}$alkylcarbonylthio, $(C_{1-6})$alkylaminocarbonyl, $di(C_{1-6})$alkylaminocarbonyl, one to three halogens, or hydroxy;

and aryl optionally substituted with $C_{1-6}$alkyl, $C_{1-6}$alkoxy, $C_{2-6}$ alkenyl, $-NH_2$, $-NH(C_{1-6})$alkyl, $-N(C_{1-6})$dialkyl, aryl, heteroaryl, aryloxy, heteroaryloxy, halogen, hydroxy, or nitro;

alternatively, when $R^6$ is $C_{1-8}$alkoxy, $R^5$ and $R^6$ are taken together with the atoms to which they are attached to form a 5-8 membered monocyclic ring;

and provided that $R^5$ is other than $C_{1-3}$alkyl substituted with $di(C_{1-6})$alkylamino-carbonyl when ring system A is 3,4- difluoro-phenyl, $R^6$ is OH, and $Z$-$R^4$ is 5-chloro-benzothiophen-3-yl; and provided that $R^5$ is other than $C_{1-3}$alkyl substituted with $C_{1-6}$alkylcarbonylthio when ring system A is 3,4-difluoro-phenyl, $R^6$ is $CH_3$, and $Z$-$R^4$ is 5-chloro-benzothiophen-3-yl;

$R^6$ is selected from the group consisting of $C_{1-6}$alkyl, $C_{1-8}$alkoxy, heteroaryl, aryl, and hydroxy; wherein alkyl and $C_{1-8}$alkoxy are optionally substituted on a terminal carbon atom with a substituent selected from $C_{1-3}$alkoxy, aryl, or hydroxy; and alkoxy is optionally substituted on a terminal carbon with a substituent independently selected from the group consisting of $C_{1-6}$alkylcarbonyloxy, and di($C_{1-6}$)alkylaminocarbonyl; and wherein heteroaryl and aryl are optionally substituted with one to three substituents independently selected from the group consisting of aryl, hydroxy, $C_{1-6}$alkoxy, and halogen;

Z is a bicyclic aryl or bicyclic heteroaryl;

$R^4$ is one to three substituents selected from the group consisting of H, $C_{1-6}$alkyl, $C_{1-6}$alkenyl, $C_{1-6}$alkoxy, aryl ($C_{2-6}$)alkenyl, halogen, —C(=O)Cy, —C(=O)$NR^{31}R^{32}$, aryl, —$CO_2H$, oxo, and cyano; wherein the alkyl and alkoxy are optionally substituted with a substituent independently selected from the group consisting of —$NR^{33}R^{34}$, aryl, one to three halogen atoms, and hydroxy; wherein the aryl is optionally substituted with a substituent independently selected from the group consisting of hydrogen, $C_{1-6}$alkyl, $C_{1-6}$alkoxy, aryl, halogen, hydroxy, and nitro;

wherein said $R^{31}$, $R^{32}$, $R^{33}$, and $R^{34}$ are substituents independently selected from the group consisting of hydrogen, $C_{1-6}$ alkyl, and aryl, wherein alkyl is optionally substituted with hydroxy, aryl, —C(=O)$C_{1-4}$alkoxy, $NH_2$, NH($C_{1-6}$ alkyl), or —N($C_{1-6}$)dialkyl; or $R^{31}$ with $R^{32}$, or $R^{33}$ with $R^{34}$ are optionally taken together with the atoms to which they are attached to form a ring of five to seven members;

and pharmaceutically acceptable salts thereof; comprising the steps of

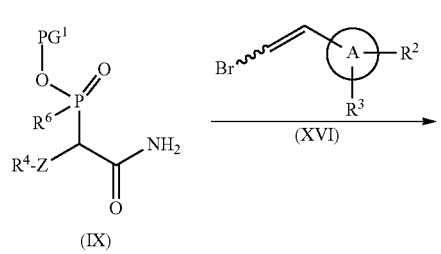

(a) reacting a compound of formula (IV), wherein $PG^1$ is an oxygen protecting group; with a source of nitrogen; in the presence of $CO_2$ gas; in an organic solvent; to yield the corresponding compound of formula (IX);

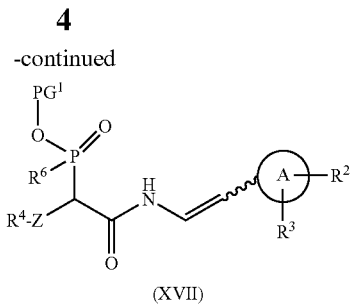

(b) reacting the compound of formula (IX) with a compound of formula (XVI); in the presence of CuI; in the presence of an inorganic base; in the presence of a ligand; in an organic solvent or mixture thereof; to yield the corresponding compound of formula (XVII);

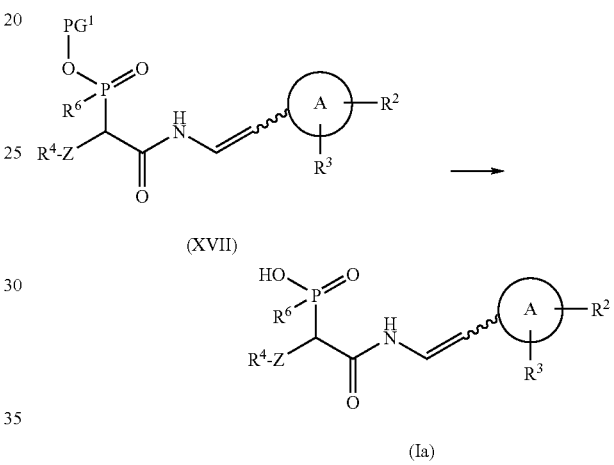

(c) de-protecting the compound of formula (XVII); to yield the corresponding compound of formula (Ia); and

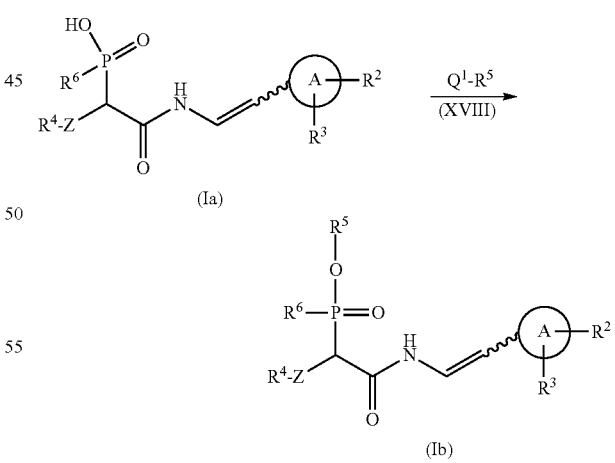

(d) optionally reacting the compound of formula (Ia) with a compound of formula (XVIII), wherein $Q^1$ is a leaving group and wherein $R^5$ is other than hydrogen; in the presence of an organic base; in an organic solvent; to yield the corresponding compound of formula (Ib), wherein $R^5$ is other than hydrogen.

The present invention is further directed to processes for the preparation of compound of formula (I)

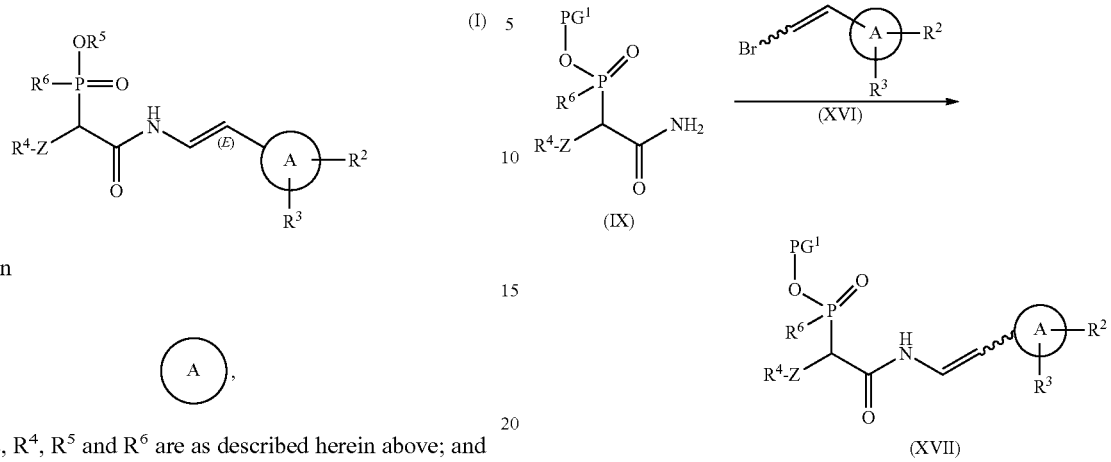

wherein $R^2$, $R^3$, Z, $R^4$, $R^5$ and $R^6$ are as described herein above; and pharmaceutically acceptable salt thereof; comprising the steps of

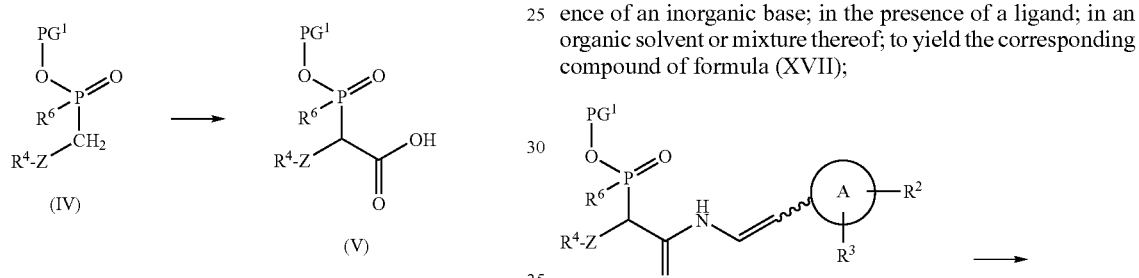

(a) reacting a compound of formula (IV) with $CO_2$; in the presence of a base; in an organic solvent or mixture thereof; to yield the corresponding compound of formula (V);

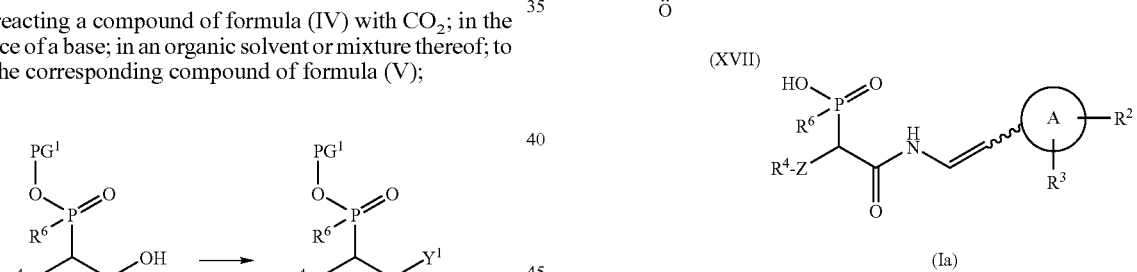

(b) activating the compound of formula (V); to yield the corresponding compound of formula (A1); wherein $Y^1$ is selected from the group consisting of chloro, —O—C(O)—$C_{1-4}$alkyl and 1-imidazolyl;

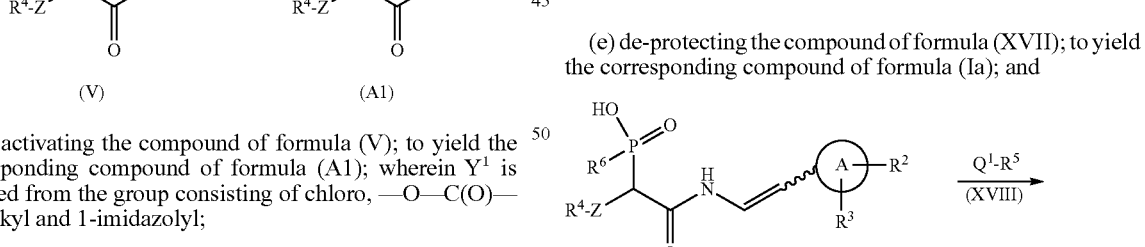

(c) reacting the compound of formula (A1) with a source of ammonia; in an organic solvent; to yield the corresponding compound of formula (IX);

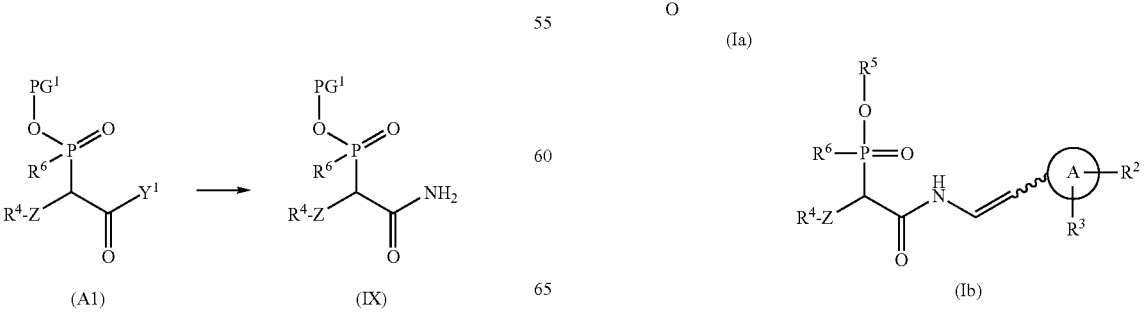

(d) reacting the compound of formula (IX) with a compound of formula (XVI); in the presence of CuI; in the presence of an inorganic base; in the presence of a ligand; in an organic solvent or mixture thereof; to yield the corresponding compound of formula (XVII);

(e) de-protecting the compound of formula (XVII); to yield the corresponding compound of formula (Ia); and (f) optionally reacting the compound of formula (Ia) with a compound of formula (XVIII), wherein $Q^1$ is a leaving group and wherein $R^5$ is other than hydrogen; in the presence of an organic base; in an organic solvent; to yield the corresponding compound of formula (Ib), wherein $R^5$ is other than hydrogen.

Step (b) of said process is preferably accomplished by:

reacting the compound of formula (V) with a source of chlorine; in an organic solvent; to yield the corresponding compound of formula (A1) wherein $Y^1$ is Cl; or reacting the compound of formula (V) with a $C_{1-4}$alkyl chloroformate; in an organic solvent; to yield the corresponding compound of formula (A1), wherein Y is —O—C(O)—$C_{1-4}$alkyl; or reacting the compound of formula (V) with CDI; in an organic solvent; to yield the corresponding compound of formula (A1), wherein $Y^1$ is 1-imidazolyl.

The present invention is further directed to processes for the preparation of compounds of formula (I)

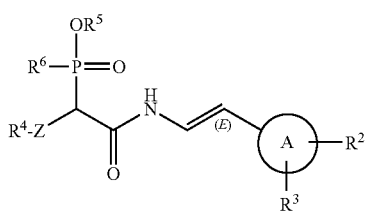

wherein

$R^2$, $R^3$, Z, $R^4$, $R^5$ are as described herein above and $R^6$ is hydroxy; and pharmaceutically acceptable salts thereof; comprising the steps of

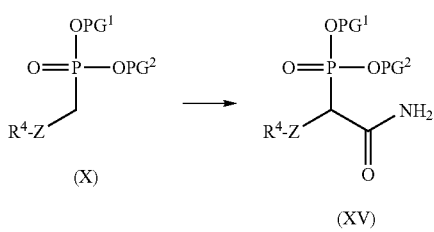

(a) reacting a compound of formula (X), wherein $PG^1$ is an oxygen protecting group and $PG^2$ is an oxygen protecting group; with a source of nitrogen; in the presence of $CO_2$ gas; in an organic solvent; to yield the corresponding compound of formula (XV);

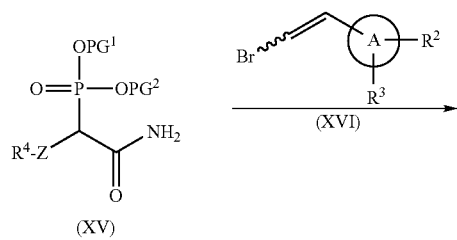

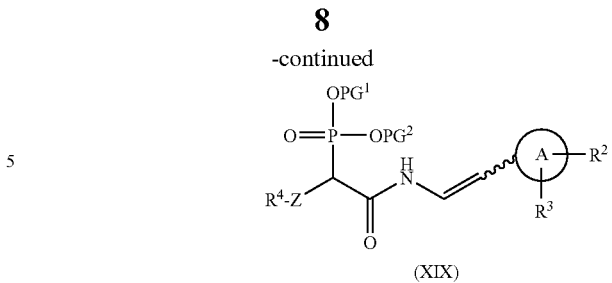

(b) reacting the compound of formula (XV) with a compound of formula (XVI); in the presence of CuI; in the presence of an inorganic base; in the presence of a ligand; in an organic solvent or mixture thereof; to yield the corresponding compound of formula (XIX);

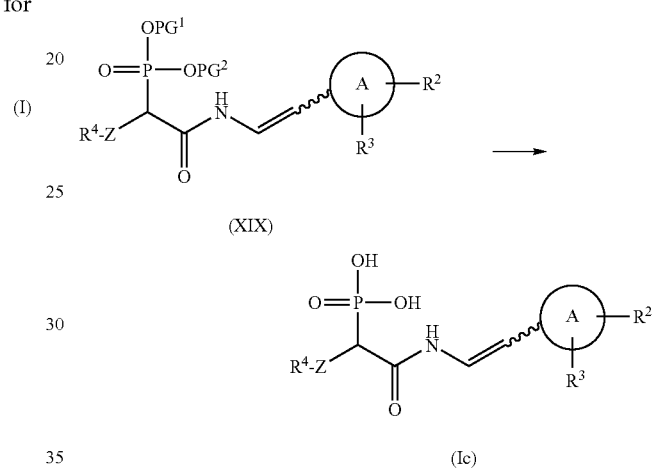

(c) de-protecting the compound of formula (XIX); to yield the corresponding compound of formula (Ic); and

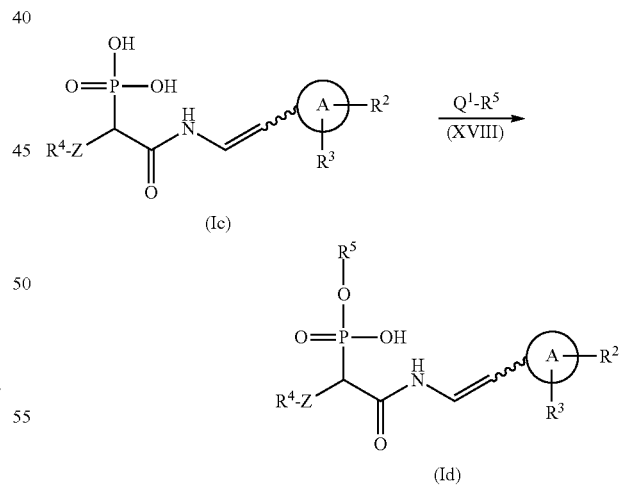

(d) optionally reacting the compound of formula (Ic) with a compound of formula (XVIII), wherein $Q^1$ is a leaving group and wherein $R^5$ is other than hydrogen; in the presence of an organic base; in an organic solvent; to yield the corresponding compound of formula (Id), wherein $R^5$ is other than hydrogen.

The present invention is further directed to a process for the preparation of compounds of formula (I)

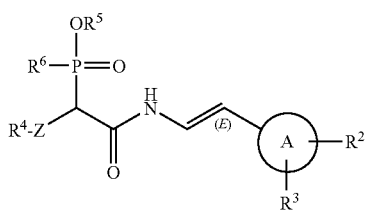

wherein

$R^2$, $R^3$, Z, $R^4$, $R^5$ are as described herein above and $R^6$ is hydroxy; and pharmaceutically acceptable salts thereof; comprising the steps of

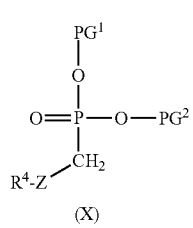 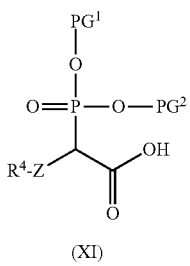

(a) reacting a compound of formula (X) with $CO_2$; in the presence of a base; in an organic solvent or mixture thereof; to yield the corresponding compound of formula (XI);

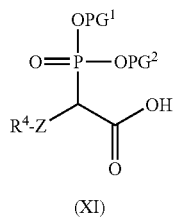 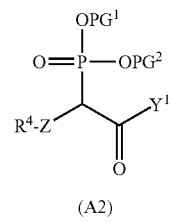

(b) activating the compound of formula (XI); to yield the corresponding compound of formula (A2), wherein $Y^1$ is selected from the group consisting of chloro, —O—C(O)—$C_{1-4}$alkyl and 1-imidazolyl;

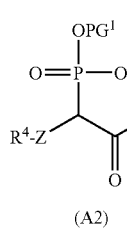 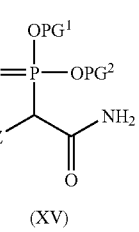

(c) reacting the compound of formula (A2) with a source of ammonia; in an organic solvent; to yield the corresponding compound of formula (XV);

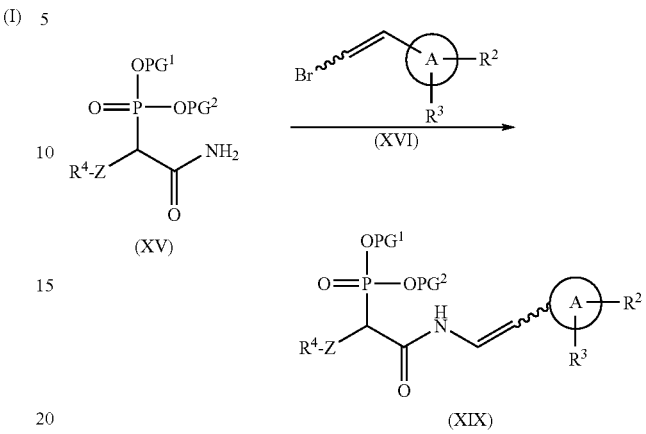

(d) reacting the compound of formula (XV) with a compound of formula (XVI); in the presence of CuI; in the presence of an inorganic base; in the presence of a ligand; in an organic solvent or mixture thereof; to yield the corresponding compound of formula (XIX);

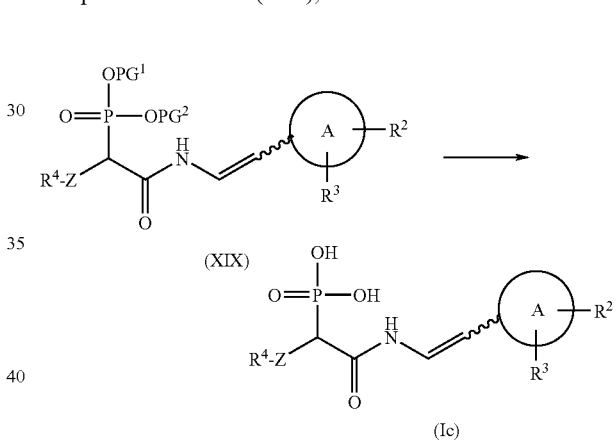

(e) de-protecting the compound of formula (XIX); to yield the corresponding compound of formula (Ic); and

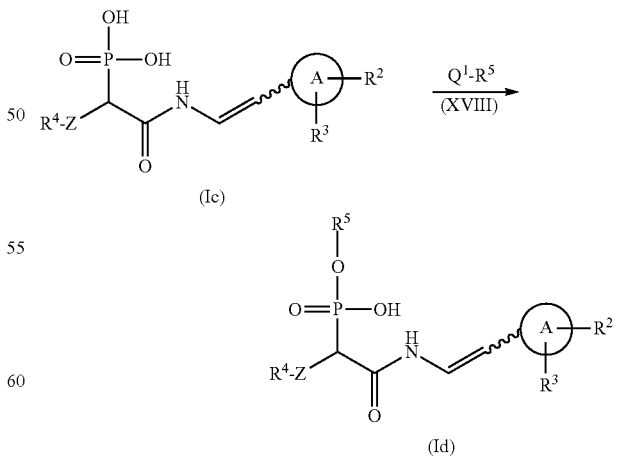

(f) optionally reacting the compound of formula (Ic) with a compound of formula (XVIII), wherein $Q^1$ is a leaving group and wherein $R^5$ is other than hydrogen; in the presence of an organic base; in an organic solvent; to yield the corresponding compound of formula (Id), wherein $R^5$ is other than hydrogen.

Step (b) of said process is preferably accomplished by:

reacting the compound of formula (V) with a source of chlorine; in an organic solvent; to yield the corresponding compound of formula (A1) wherein $Y^1$ is Cl; or reacting the compound of formula (V) with a $C_{1-4}$alkyl chloroformate; in an organic solvent; to yield the corresponding compound of formula (A1), wherein Y is —O—C(O)—$C_{1-4}$alkyl; or reacting the compound of formula (V) with CDI; in an organic solvent; to yield the corresponding compound of formula (A1), wherein $Y^1$ is 1-imidazolyl.

The present invention is further directed to compounds of formula (L)

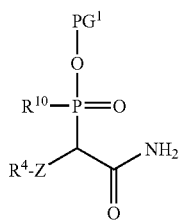

(L)

wherein $PG^1$ is an oxygen protecting group;

$R^{10}$ is selected from the group consisting of —O-$PG^2$ and $R^6$;

$PG^2$ is an oxygen protecting group $R^6$ is selected from the group consisting of $C_{1-6}$alkyl, $C_{1-8}$alkoxy, heteroaryl, aryl, and hydroxy; wherein alkyl and $C_{1-8}$alkoxy are optionally substituted on a terminal carbon atom with a substituent selected from $C_{1-3}$alkoxy, aryl, or hydroxy; and alkoxy is optionally substituted on a terminal carbon with a substituent independently selected from the group consisting of $C_{1-6}$alkylcarbonyloxy, and di($C_{1-6}$)alkylaminocarbonyl; and wherein heteroaryl and aryl are optionally substituted with one to three substituents independently selected from the group consisting of aryl, hydroxy, $C_{1-6}$alkoxy, and halogen.

Z is a bicyclic aryl or bicyclic heteroaryl;

$R^4$ is one to three substituents selected from the group consisting of H, $C_{1-6}$alkyl, $C_{1-6}$alkenyl, $C_{1-6}$alkoxy, aryl ($C_{2-6}$)alkenyl, halogen, —C(=O)Cy, —C(=O)$NR^{31}R^{32}$, aryl, —$CO_2$H, oxo, and cyano; wherein the alkyl and alkoxy are optionally substituted with a substituent independently selected from the group consisting of —$NR^{33}R^{34}$, aryl, one to three halogen atoms, and hydroxy; wherein the aryl is optionally substituted with a substituent independently selected from the group consisting of hydrogen, $C_{1-6}$alkyl, $C_{1-6}$alkoxy, aryl, halogen, hydroxy, and nitro;

wherein said $R^{31}$, $R^{32}$, $R^{33}$, and $R^{34}$ are substituents independently selected from the group consisting of hydrogen, $C_{1-6}$ alkyl, and aryl, wherein alkyl is optionally substituted with hydroxy, aryl, —C(=O)$C_{1-4}$alkoxy, $NH_2$, $NH(C_{1-6}$ alkyl), or —N($C_{1-6}$)dialkyl; or $R^{31}$ with $R^{32}$, or $R^{33}$ with $R^{34}$ are optionally taken together with the atoms to which they are attached to form a ring of five to seven members;

or a pharmaceutically acceptable salt thereof.

The present invention is further directed to a process for the preparation of compounds of formula (IX)

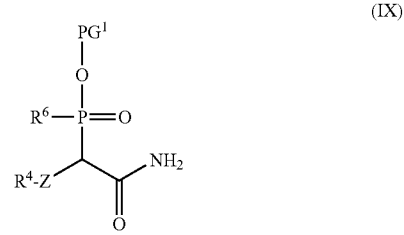

(IX)

wherein $PG^1$, $R^6$, Z and $R^4$ substituents as described herein above (compounds of formula (L) wherein $R^{10}$ is $R^6$); and pharmaceutically acceptable salts thereof; comprising the step of

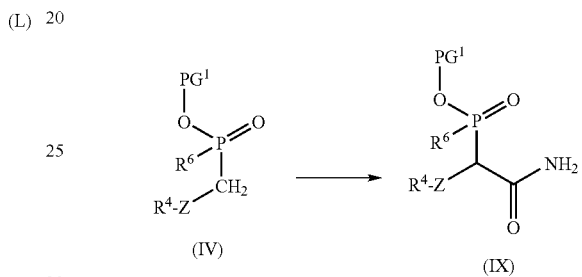

(a) reacting a compound of formula (IV), wherein $PG^1$ is an oxygen protecting group; with a source of nitrogen; in the presence of $CO_2$ gas; in an organic solvent; to yield the corresponding compound of formula (IX).

The present invention is further directed to processes for the preparation of compounds of formula (IX)

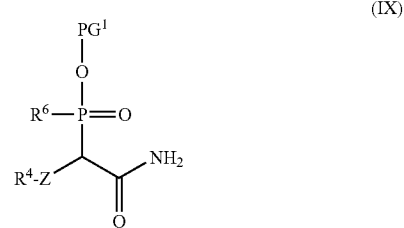

(IX)

wherein $PG^1$, $R^6$, Z and $R^4$ are as described herein above (compounds of formula (L) wherein $R^{10}$ is $R^6$); and pharmaceutically acceptable salts thereof; comprising the step of

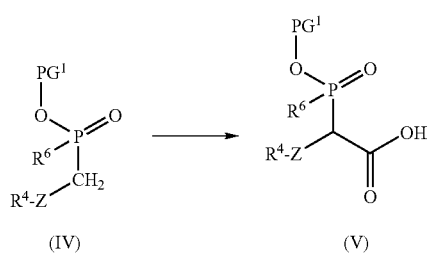

(a) reacting a compound of formula (IV) with $CO_2$; in the presence of a base; in an organic solvent or mixture thereof; to yield the corresponding compound of formula (V);

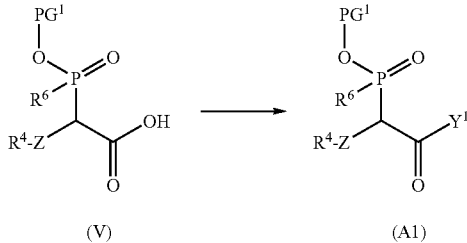

(V)  (A1)

(b) activating the compound of formula (V); to yield the corresponding compound of formula (A1); wherein $Y^1$ is selected from the group consisting of chloro, —O—C(O)—$C_{1-4}$alkyl and 1-imidazolyl;

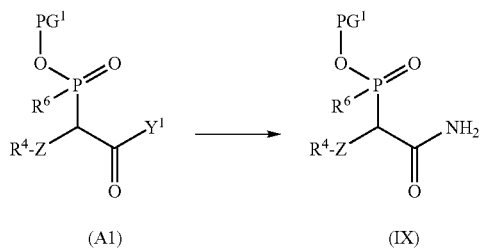

(A1)  (IX)

(c) reacting the compound of formula (A1) with a source of ammonia; in an organic solvent; to yield the corresponding compound of formula (IX).

Step (b) of said process is preferably accomplished by:

reacting the compound of formula (V) with a source of chlorine; in an organic solvent; to yield the corresponding compound of formula (A1) wherein $Y^1$ is Cl; or reacting the compound of formula (V) with a $C_{1-4}$alkyl chloroformate; in an organic solvent; to yield the corresponding compound of formula (A1), wherein Y is —O—C(O)—$C_{1-4}$alkyl; or reacting the compound of formula (V) with CDI; in an organic solvent; to yield the corresponding compound of formula (A1), wherein $Y^1$ is 1-imidazolyl.

The present invention is further directed to processes for the preparation of compounds of formula (XV)

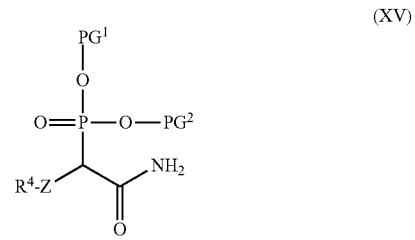

(XV)

wherein $PG^1$, $PG^2$, Z and $R^4$ are as described herein above (compounds of formula (L) wherein $R^{10}$ is —O-$PG^2$); and pharmaceutically acceptable salts thereof; comprising the step of

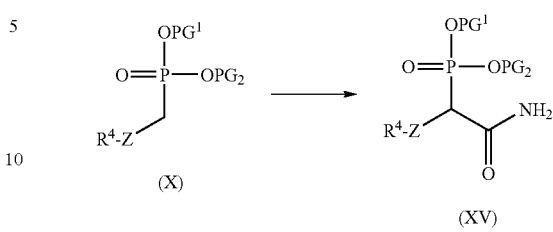

(X)  (XV)

(a) reacting a compound of formula (X), wherein $PG^1$ is an oxygen protecting group and $PG^2$ is an oxygen protecting group; with a source of nitrogen; in the presence of $CO_2$ gas; in an organic solvent; to yield the corresponding compound of formula (XV).

The present invention is further directed to processes for the preparation of compounds of formula (XV)

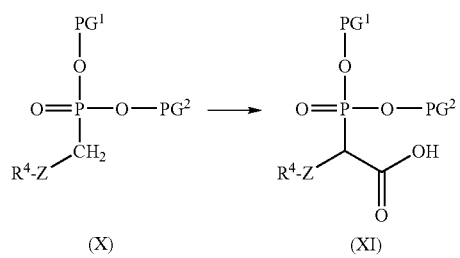

(XV)

wherein $PG^1$, $PG^2$, Z and $R^4$ are as described herein above (compounds of formula (L) wherein $R^{10}$ is —O-$PG^2$); and pharmaceutically acceptable salts thereof; comprising the step of

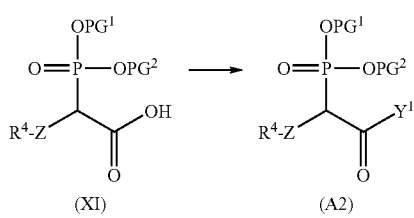

(X)  (XI)

(a) reacting a compound of formula (X) with $CO_2$; in the presence of a base; in an organic solvent or mixture thereof; to yield the corresponding compound of formula (XI);

(XI)  (A2)

(b) activating the compound of formula (XI); to yield the corresponding compound of formula (A2), wherein $Y^1$ is selected from the group consisting of chloro, —O—C(O)—$C_{1-4}$alkyl and 1-imidazolyl;

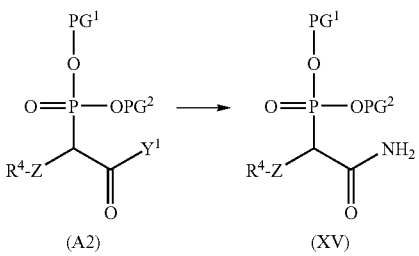

(c) reacting the compound of formula (A2) with a source of ammonia; in an organic solvent; to yield the corresponding compound of formula (XV).

Step (b) of said process is preferably accomplished by:

reacting the compound of formula (V) with a source of chlorine; in an organic solvent; to yield the corresponding compound of formula (A1) wherein $Y^1$ is Cl; or reacting the compound of formula (V) with a $C_{1-4}$alkyl chloroformate; in an organic solvent; to yield the corresponding compound of formula (A1), wherein Y is —O—C(O)—$C_{1-4}$alkyl; or reacting the compound of formula (V) with CDI; in an organic solvent; to yield the corresponding compound of formula (A1), wherein $Y^1$ is 1-imidazolyl.

The present invention is further directed to a process for the preparation of a compound of formula (III)

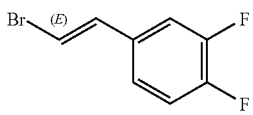

comprising the step of

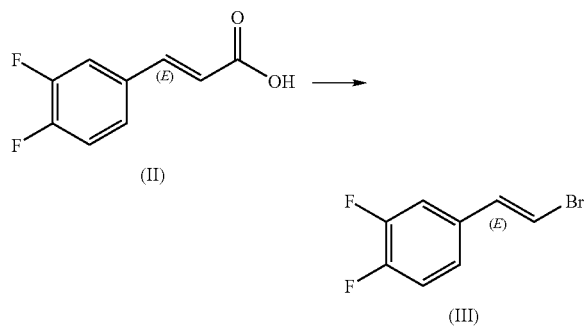

(a) reacting a compound of formula (II) with a brominating agent; in the presence of a catalyst; in a mixture of water and an organic solvent; to yield the corresponding compound of formula (III).

The present invention is further directed to a product prepared according to any of the processes described herein.

DETAILED DESCRIPTION OF THE INVENTION

The present invention is directed to a process for the preparation of compound of formula (I)

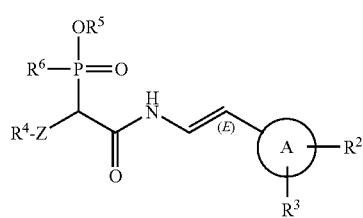

wherein Z, $R^4$, $R^5$, $R^6$, $R^2$, $R^3$ and

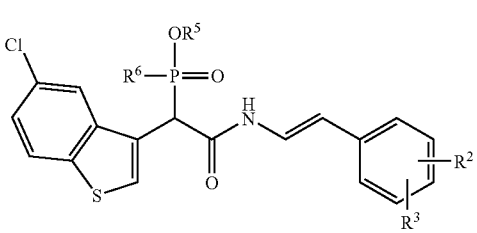

are as herein defined; and pharmaceutically acceptable salts thereof. The compounds of formula (I), prepared according to the processes described herein, are useful in methods for treating or ameliorating a serine protease-mediated disorder, as disclosed in U.S. Pat. No. 7,459,444, issued Dec. 2, 2008, which is incorporated by reference herein in its entirety.

In particular, the compounds of formula (I) are useful in treating or ameliorating a chymase mediated disorder such as, but not limited to, allergic rhinitis, viral rhinitis, asthma, chronic obstructive pulmonary diseases, bronchitis, pulmonary emphysema, acute lung injury (e.g. adult (acute) respiratory distress syndrome), psoriasis, arthritis, reperfusion injury, ischemia, hypertension, hypercardia, myocardial infarction, heart failure damage associated with myocardial infarction, cardiac hypertrophy, arteriosclerosis, saroidosis, vascular stenosis or restenosis (e.g., associated with vascular injury, angioplasty, vascular stents or vascular grafts), pulmonary fibrosis, kidney fibrosis (e.g., associated with glomerulonephritis), liver fibrosis, post surgical adhesion formation, systemic sclerosis, keloid scars, rheumatoid arthritis, bullous pemphigoid, and atherosclerosis. Additionally, the compounds of formula (I) are useful for modulating wound healing and remodeling (e.g., cardiac hypertrophy) as well as immune modulation.

In an embodiment, the present invention is directed to a process for the preparation of compounds of formula (I-S)

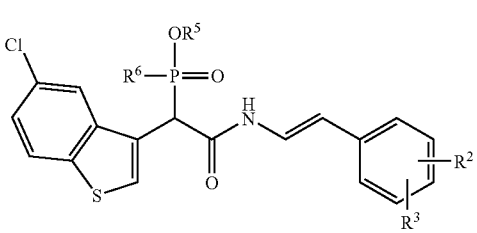

wherein
$R^2$ and $R^3$ are each independently selected from halogen;
$R^5$ is selected from the group consisting of hydrogen and $C_{1-3}$alkyl;
wherein the $C_{1-3}$alkyl is optionally substituted with $C_{1-6}$alkylcarbonyloxy or $C_{1-6}$alkoxycarbonyloxy;
$R^6$ is hydroxy;
and pharmaceutically acceptable salts thereof; as described in more detail herein.

In an embodiment, the present invention is directed to processes for the preparation of compounds of formula (I) wherein $R^6$ is other than hydroxy.

In another embodiment, the present invention is directed to processes for the preparation of compounds of formula (I) wherein $R^6$ is $C_{1-4}$alkyl.

In another embodiment, the present invention is directed to processes for the preparation of compounds of formula (I) wherein $R^6$ is hydroxy.

In an embodiment, the present invention is directed to processes for the preparation of compounds of formula (I) wherein $R^5$ is hydrogen.

In another embodiment, the present invention is directed to processes for the preparation of compounds of formula (I) wherein $R^5$ is selected from the group consisting of —CH$_2$—O—C(O)-t-butyl and —CH$_2$—O—C(O)—O-isopropyl.

In another embodiment, the present invention is directed to a process for the preparation of a compound of formula (I-A)

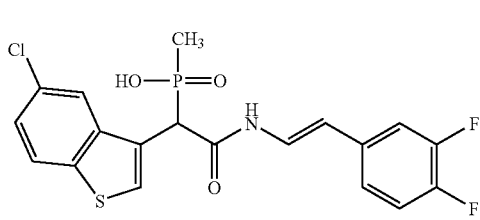
(I-A)

also known as E-{(5-chloro-benzo[b]thiophen-3-yl)-[2-(3,4-difluoro-phenyl)-vinylcarbamoyl]-methyl}-methyl-phosphinic acid, and pharmaceutically acceptable salts thereof.

In another embodiment, the present invention is directed to a process for the preparation of a compound of formula (I-B)

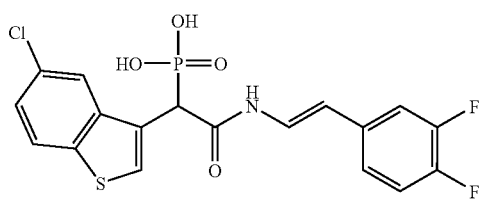
(I-B)

also known as E-{(5-Chloro-benzo[b]thiophen-3-yl)-[2-(3,4-difluoro-phenyl)-vinylcarbamoyl]methyl}-phosphonic acid, and pharmaceutically acceptable salts thereof.

In another embodiment, the present invention is directed to a process for the preparation of a compound of formula (I-C)

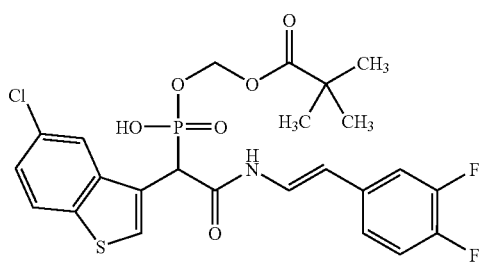
(I-C)

also known as E-{(5-chloro-benzo[b]thiophen-3-yl)-[2-(3,4-difluoro-phenyl)-vinylcarbamoyl]methyl}-hydroxy-phosphinoyloxymethyl ester 2,2-dimethyl-propionic acid, and pharmaceutically acceptable salts thereof.

In another embodiment, the present invention is directed to a process for the preparation of a compound of formula (I-D)

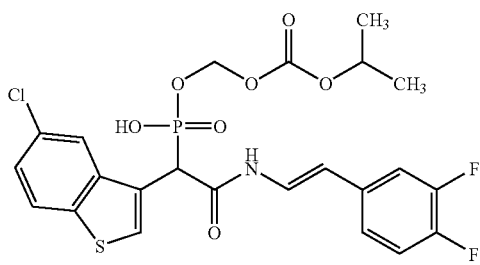
(I-D)

also known as E-{(5-Chloro-benzo[b]thiophen-3-yl)-[2-(3,4-difluoro-phenyl)-vinylcarbamoyl]-methyl}-phosphonic acid monoisopropoxycarbonyloxymethyl ester, and pharmaceutically acceptable salts thereof; as described in more detail herein.

In another embodiment, the present invention is directed to a process for the preparation of a compound of formula (I-E)

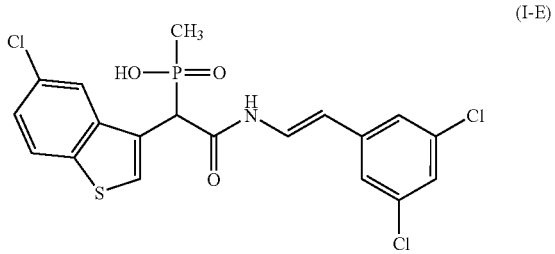
(I-E)

also known as E-{(5-Chloro-benzo[b]thiophen-3-yl)-[2-(3,5-dichloro-phenyl)-vinylcarbamoyl]-methyl}-methyl-phosphinic acid, and pharmaceutically acceptable salts thereof.

In another embodiment, the present invention is directed to a process for the preparation of a compound of formula (I-F)

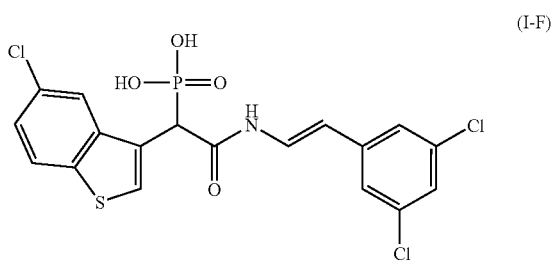
(I-F)

also known as E-{(5-Chloro-benzo[b]thiophen-3-yl)-[2-(3,5-dichloro-phenyl)-vinylcarbamoyl]-methyl}-phosphonic acid, and pharmaceutically acceptable salts thereof.

In another embodiment, the present invention is directed to a process for the preparation of a compound of formula (I-G)

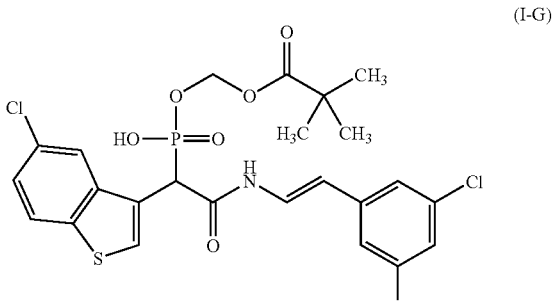
(I-G)

also known as E-{(5-chloro-benzo[b]thiophen-3-yl)-[2-(3,5-dichloro-phenyl)-vinylcarbamoyl]-methyl}-hydroxy-phosphinoyloxymethyl ester 2,2-dimethyl-propionic acid, and pharmaceutically acceptable salts thereof.

In another embodiment, the present invention is directed to a process for the preparation of a compound of formula (I-H)

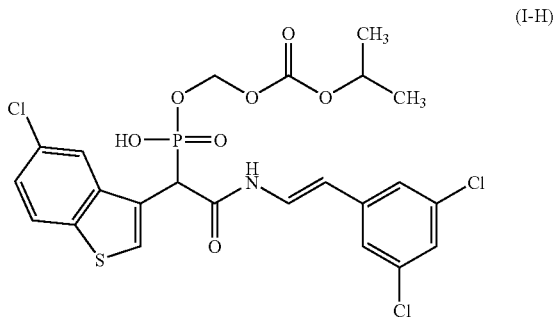

(I-H)

also known as E-{(5-Chloro-benzo[b]thiophen-3-yl)-[2-(3,5-dichloro-phenyl)-vinylcarbamoyl]-methyl}-phosphonic acid monoisopropoxycarbonyloxymethyl ester, and pharmaceutically acceptable salts thereof; as described in more detail hereinafter.

The present invention is further directed to compounds of formula (L)

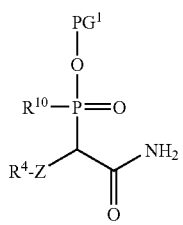

(L)

wherein $PG^1$, $R^{10}$, Z and $R^4$ are as described herein above; and pharmaceutically acceptable salts thereof.

In an embodiment, the present invention is further directed to compounds of formula (L) wherein $R^{10}$ is $R^6$; herein referred to as compounds of formula (IX)

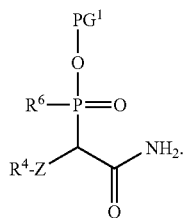

(IX)

In an embodiment, the present invention is further directed to compounds of formula (L) wherein $R^{10}$ is O-$PG^2$; herein referred to as compounds of formula (XV)

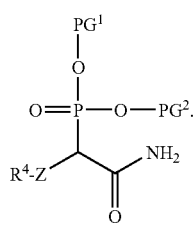

(XV)

The present invention is further directed to processes for the preparation of compounds of formula (L), as described in more detail herein.

In an embodiment, the present invention is directed to processes for the preparation of the compounds of formula (IX), as described in more detail herein. The compounds of formula (IX) are useful as intermediates in the synthesis of the compounds of formula (I).

In another embodiment, the present invention is directed processes for the preparation of compounds of formula (XV), as described in more detail herein. The compounds of formula (XV) are useful as intermediates in the synthesis of the compounds of formula (I), more particularly compounds of formula (I) wherein $R^6$ is hydroxy.

In another embodiment, the present invention is directed to processes for the preparation of a compound of formula (IX-S)

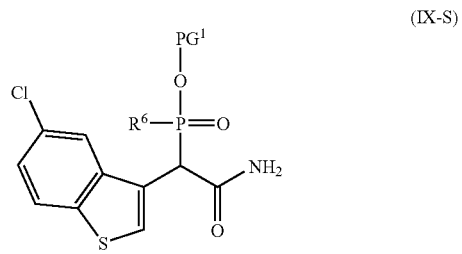

(IX-S)

wherein $PG^1$ is an oxygen protecting group (preferably $PG^1$ is selected from the group consisting of $C_{1-4}$alkyl);

$R^6$ is selected from the group consisting of $C_{1-6}$alkyl, $C_{1-6}$alkoxy, heteroaryl, aryl, and hydroxy; wherein alkyl and $C_{1-8}$alkoxy are optionally substituted on a terminal carbon atom with a substituent selected from $C_{1-3}$alkoxy, aryl, or hydroxy; and alkoxy is optionally substituted on a terminal carbon with a substituent independently selected from the group consisting of $C_{1-6}$alkylcarbonyloxy, and di($C_{1-6}$)alkylaminocarbonyl; and wherein heteroaryl and aryl are optionally substituted with one to three substituents independently selected from the group consisting of aryl, hydroxy, $C_{1-6}$alkoxy, and halogen; as described in more detail herein.

In another embodiment, the present invention is directed to a process for the preparation of a compound of formula (IX-S) wherein $R^6$ is methyl.

In another embodiment, the present invention is directed to a process for the preparation of a compound of formula (IX-S) wherein $R^6$ is hydroxy.

In another embodiment, the present invention is directed to a process for the preparation of a compound of formula (IX-S) wherein $PG^1$ is ethyl; and wherein $R^6$ is selected from the group consisting of methyl and hydroxy.

In another embodiment, the present invention is directed to processes for the preparation of a compound of formula (XV-S)

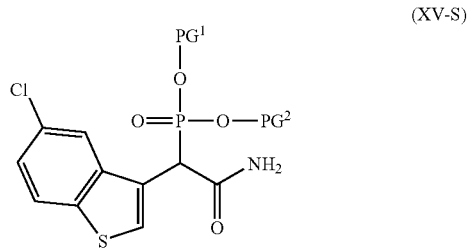

(XV-S)

wherein $PG^1$ is an oxygen protecting group and $PG^2$ is an oxygen protecting group; as described in more detail herein.

In an embodiment of the present invention, $PG^1$ and $PG^2$ are the same oxygen protecting group.

In another embodiment of the present invention, PG$^1$ and PG$^2$ are different oxygen protecting groups.

In another embodiment of the present invention, PG$^1$ and PG$^2$ are each independently selected from C$_{1-4}$alkyl.

In another embodiment of the present invention, PG$^1$ and PG$^2$ are the same and are selected from the group consisting of methyl and ethyl.

The present invention is directed to a process for the preparation of a compound selected from the group consisting of a compound of formula (III)

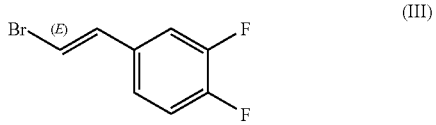

as described in more detail herein.

In an embodiment of the present invention, the compound of formula (III) is present in an excess of its trans isomer of greater than or equal to about 90%, preferably greater than or equal to about 95%, more preferably greater than or equal to about 98%, more preferably greater than or equal to about 99%.

In an embodiment, the present invention is directed to a process for the preparation of a compound of formula (I) wherein <div style="text-align:center">(A)</div> is selected from group consisting of naphthyl, benzothiazolyl, benzothiophenyl, quinolinyl, isoquinolinyl, dihydronaphthyl, indanyl, tetralinyl and benzodioxolyl when n is equal to zero; and A is selected from phenyl, pyridin-2-yl, or pyridin-3-yl when n is equal to one.

In another embodiment, the present invention is directed to a process for the preparation of a compound of formula (I) wherein <div style="text-align:center">(A)</div> is selected from phenyl, pyridin-2-yl, or pyridin-3-yl when n is equal to one.

In an embodiment, the present invention is directed to a process for the preparation of a compound of formula (I) wherein R$^2$ is a substituent independently selected from the group consisting of C$_{1-4}$alkyl, methoxy, C$_{2-4}$alkoxy, hydroxy, halogen, and —NH$_2$.

In an embodiment, the present invention is directed to a process for the preparation of a compound of formula (I) wherein R$^3$ is one to three substituents independently selected from the group consisting of C$_{1-6}$alkyl, C$_{1-6}$alkoxy, —NR$^{19}$R$^{20}$, —NHC(=O)Cy, —C(=O)NR$^{17}$R$^{18}$, —C(=O)NHcycloalkyl, —C(=O)N(C$_{1-6}$alkyl)cycloalkyl, halogen, and aryl; wherein alkyl and alkoxy are optionally substituted on a terminal carbon atom with one to three fluorine atoms, —NH$_2$, —NHCy, or —N(C$_{1-4}$alkyl)Cy; and wherein aryl and cycloalkyl are optionally substituted with a group independently selected from R$^{14}$.

In an embodiment, the present invention is directed to a process for the preparation of a compound of formula (I) wherein R$^5$ is hydrogen or C$_{1-3}$alkyl optionally substituted with C$_{1-6}$alkylcarbonyloxy, C$_{1-6}$alkoxycarbonyloxy, C$_{1-6}$alkylcarbonylthio, (C$_{1-6}$)alkylaminocarbonyl, or di(C$_{1-6}$)alkylaminocarbonyl; and alternatively, when R$^6$ is C$_{1-8}$alkoxy, R$^5$ and R$^6$ are taken together with the atoms to which they are attached to form a 6-membered monocyclic ring; and provided that R$^5$ is other than C$_{1-3}$alkyl substituted with di(C$_{1-6}$)alkylamino-carbonyl when ring system A is 3,4-difluoro-phenyl, R$^6$ is OH, and Z-R$^4$ is 5-chloro-benzothiophen-3-yl; and provided that R$^5$ is other than C$_{1-3}$alkyl substituted with C$_{1-6}$alkylcarbonylthio when ring system A is 3,4-difluoro-phenyl, R$^6$ is CH$_3$, and Z-R$^4$ is 5-chloro-benzothiophen-3-yl.

In an embodiment, the present invention is directed to a process for the preparation of a compound of formula (I) wherein R$^6$ is selected from the group consisting of methyl, ethyl, methoxypropyl, phenethyl, benzo[1,3]dioxol-5-yl-propyl, hydroxy, and C$_{1-3}$alkoxy optionally substituted with C$_{1-6}$alkylcarbonyloxy, and di(C$_{1-6}$)alkylamino-carbonyl.

In an embodiment, the present invention is directed to a process for the preparation of a compound of formula (I) wherein Z is independently selected from the group consisting of indolyl, benzothiophenyl, naphthalenyl, quinolinyl, isoquinolinyl and benzothiazolonyl.

In an embodiment, the present invention is directed to a process for the preparation of a compound of formula (I) wherein R$^4$ is one to three substituents selected from the group consisting of C$_{1-6}$alkyl, C$_{1-6}$alkenyl, aryl(C$_{2-6}$)alkenyl, halogen, and —C(=O)Cy; wherein aryl is optionally substituted with a substituent selected from halogen or C$_{1-4}$alkoxy.

In an embodiment, the present invention is directed to a process for the preparation of a compound of formula (I) wherein <div style="text-align:center">(A)</div> is a ring system of the formula:

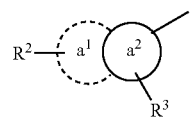

wherein the a$^1$ portion of said a$^1$a$^2$ is optionally substituted with R$^2$; and the a$^2$ portion is optionally substituted with R$^3$ and n is 0. In another embodiment, the present invention is directed to a process for the preparation of a compound of formula (I) wherein <div style="text-align:center">(A)</div> is a ring system of the formula:

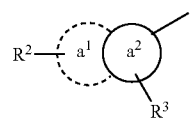

and wherein the a² portion is aromatic and

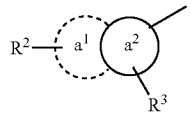

is selected from group consisting of naphthyl, benzothiazolyl, benzothiophenyl, quinolinyl, isoquinolinyl, dihydronaphthyl, indanyl, tetralinyl and benzodioxolyl.

In an embodiment, the present invention is directed to a process for the preparation of a compound of formula (I) wherein $R^2$ is a substituent independently selected from the group consisting of $C_{1-4}$alkyl, methoxy, $C_{2-4}$alkoxy, hydroxy, halogen, and —$NH_2$.

In an embodiment, the present invention is directed to a process for the preparation of a compound of formula (I) wherein $R^3$ is one to three substituents independently selected from the group consisting of $C_{1-6}$alkyl, $C_{1-6}$alkoxy, —$NR^{19}R^{20}$, —NHC(=O)Cy, —C(=O)$NR^{17}R^{18}$, —C(=O)NHcycloalkyl, —C(=O)N($C_{1-6}$alkyl)cycloalkyl, halogen, and aryl; wherein alkyl and alkoxy are optionally substituted on a terminal carbon atom with one to three fluorine atoms, —$NH_2$, NHCy, or —N($C_{1-4}$alkyl)Cy; and wherein aryl and cycloalkyl are optionally substituted with a group independently selected from $R^{14}$.

In an embodiment, the present invention is directed to a process for the preparation of a compound of formula (I) wherein $R^5$ is hydrogen or $C_{1-3}$alkyl optionally substituted with $C_{1-6}$alkylcarbonyloxy, $C_{1-6}$alkoxycarbonyloxy, $C_{1-6}$alkylcarbonylthio, ($C_{1-6}$)alkylaminocarbonyl, or di($C_{1-6}$)alkylaminocarbonyl; and alternatively, when $R^6$ is $C_{1-8}$alkoxy, $R^5$ and $R^6$ are taken together with the atoms to which they are attached to form a 6-membered monocyclic ring; provided that $R^5$ is other than $C_{1-3}$alkyl substituted with di($C_{1-6}$)alkylaminocarbonyl when ring system A is 3,4-difluoro-phenyl, $R^6$ is OH, and Z-$R^4$ is 5-chloro-benzothiophen-3-yl; and provided that $R^5$ is other than $C_{1-3}$alkyl substituted with $C_{1-6}$alkylcarbonylthio when ring system A is 3,4-difluoro-phenyl, $R^6$ is $CH_3$, and Z-$R^4$ is 5-chloro-benzothiophen-3-yl.

In an embodiment, the present invention is directed to a process for the preparation of a compound of formula (I) wherein $R^6$ is selected from the group consisting of methyl, ethyl, methoxypropyl, phenethyl, benzo[1,3]dioxol-5-yl-propyl, hydroxy, and $C_{1-3}$alkoxy optionally substituted with $C_{1-6}$alkylcarbonyloxy, and di($C_{1-6}$)alkylamino-carbonyl.

In an embodiment, the present invention is directed to a process for the preparation of a compound of formula (I) wherein Z is independently selected from the group consisting of indolyl, benzothiophenyl, naphthalenyl, quinolinyl, isoquinolinyl, and benzothiazolone.

In an embodiment, the present invention is directed to a process for the preparation of a compound of formula (I) wherein $R^4$ is one to three substituents selected from the group consisting of $C_{1-6}$alkyl, $C_{1-6}$alkenyl, aryl($C_{2-6}$)alkenyl, halogen, and —C(=O)Cy; wherein aryl is optionally substituted with a substituent selected from halogen or $C_{1-4}$alkoxy.

In an embodiment, the present invention is directed to a process for the preparation of a compound of formula (I) wherein $R^1$, ring A, $R^2$, $R^3$, $R^5$, $R^6$, Z, and $R^4$ are selected from the group consisting of

| $R^2 \diagdown\!\!\diagup R^3$ (A) | $R^5$ | $R^6$ | Z-$R^4$ |
|---|---|---|---|
| 3,4-difluoro-phenyl | H | OH | 5-Cl-benzothiophen-3-yl |
| 4-fluoro-phenyl | H | OH | 5-Cl-N-methyl-indol-3-yl |
| 3-fluoro-phenyl | H | $CH_3$ | 5-Cl-N-methyl-indol-3-yl |
| 3,4-difluoro-phenyl | H | $CH_3$ | 5-Cl-N-methyl-indol-3-yl |
| 4-amino-phenyl | H | OH | 5-Cl-benzothiophen-3-yl |
| Phenyl | H | $CH_3$ | 5-Cl-benzothiophen-3-yl |
| 3-fluoro-phenyl | H | $CH_3$ | 5-Cl-benzothiophen-3-yl |
| 3,4,5-trifluoro-phenyl | H | $CH_3$ | 5-Cl-benzothiophen-3-yl |
| 3,4-difluoro-phenyl | H | $CH_3$ | 5-Cl-benzothiophen-3-yl |
| phenyl | H | OH | 5-Cl-benzothiophen-2-yl |
| 4-fluoro-phenyl | H | OH | 5-Cl-benzothiophen-3-yl |
| 2-fluoro-phenyl | H | $CH_3$ | 5-Cl-benzothiophen-3-yl |
| 4-fluoro-phenyl | H | $CH_3$ | 5-Cl-benzothiophen-3-yl |
| pyridin-3-yl | H | OH | 5-Cl-benzothiophen-3-yl |
| 3,4-difluoro-phenyl | H | $CH_2CH_3$ | 5-Cl-benzothiophen-3-yl |
| phenyl | H | OH | naphthalen-1-yl |
| 4-methoxy-phenyl | H | OH | 5-Cl-benzothiophen-3-yl |
| 4-methyl-phenyl | H | OH | 5-Cl-benzothiophen-2-yl |
| 3,4-dimethoxy-phenyl | H | OH | 5-Cl-benzothiophen-3-yl |
| 4-hydroxy-phenyl | H | OH | 5-Cl-benzothiophen-3-yl |
| 4-chloro-phenyl | H | $CH_3$ | 5-Cl-benzothiophen-3-yl |
| 4-trifluoromethyl-phenyl | H | OH | 5-Cl-benzothiophen-3-yl |
| 2-methoxy-phenyl | H | $CH_3$ | 5-Cl-benzothiophen-3-yl |
| 2-nitro-phenyl | H | $CH_3$ | 5-Cl-benzothiophen-3-yl |
| 2-methylcarbonyloxy-phenyl | H | $CH_3$ | 5-Cl-benzothiophen-3-yl |
| 2-hydroxy-phenyl | H | $CH_3$ | 5-Cl-benzothiophen-3-yl |
| pyridin-2-yl | H | $CH_3$ | 5-Cl-benzothiophen-3-yl |
| 2-amino-phenyl | H | $CH_3$ | 5-Cl-benzothiophen-3-yl |

-continued

| R²/R³ | R⁵ | R⁶ | Z-R⁴ |
|---|---|---|---|
| 3-trifluoromethyl-phenyl | H | CH₃ | 5-Cl-benzothiophen-3-yl |
| 3-trifluoromethoxy-phenyl | H | CH₃ | 5-Cl-benzothiophen-3-yl |
| 3-methoxy-phenyl | H | CH₃ | 5-Cl-benzothiophen-3-yl |
| 2-methyl-phenyl | H | CH₃ | 5-Cl-benzothiophen-3-yl |
| 2,6-difluoro-phenyl | H | CH₃ | 5-Cl-benzothiophen-3-yl |
| 4-cyano-phenyl | H | CH₃ | 5-Cl-benzothiophen-3-yl |
| 2-ureido-phenyl | H | CH₃ | 5-Cl-benzothiophen-3-yl |
| 2-(NHC(=O))₂NH₂-phenyl | H | CH₃ | 5-Cl-benzothiophen-3-yl |
| 2-chloro-phenyl | H | CH₃ | 5-Cl-benzothiophen-3-yl |
| 3-chloro-phenyl | H | CH₃ | 5-Cl-benzothiophen-3-yl |
| 3,5-difluoro-phenyl | H | CH₃ | 5-Cl-benzothiophen-3-yl |
| 2,3-difluoro-phenyl | H | CH₃ | 5-Cl-benzothiophen-3-yl |
| 2-bromo-phenyl | H | CH₃ | 5-Cl-benzothiophen-3-yl |
| 2,3-dimethoxy-phenyl | H | CH₃ | 5-Cl-benzothiophen-3-yl |
| 3-nitro-phenyl | H | CH₃ | 5-Cl-benzothiophen-3-yl |
| 3-bromo-phenyl | H | CH₃ | 5-Cl-benzothiophen-3-yl |
| 3,5-dimethoxy-phenyl | H | CH₃ | 5-Cl-benzothiophen-3-yl |
| 2,5-difluoro-phenyl | H | CH₃ | 5-Cl-benzothiophen-3-yl |
| 3,5-dichloro-phenyl | H | CH₃ | 5-Cl-benzothiophen-3-yl |
| 2,4-difluoro-phenyl | H | CH₃ | 5-Cl-benzothiophen-3-yl |
| 3-amino-phenyl | H | CH₃ | 5-Cl-benzothiophen-3-yl |
| phenyl | —CH₂C(Me)₂CH₂O— | | naphthalen-1-yl |
| phenyl | 3-methoxy-prop-1-yl | OH | naphthalen-1-yl |
| phenyl | 3-methoxy-prop-1-yl | 3-methoxy-prop-1-yl-oxy | naphthalen-1-yl |
| phenyl | 2-(1,3-dioxolan-2-yl)-eth-1-yl | OH | naphthalen-1-yl |
| phenyl | —CH₂OC(=O)t-butyl | OH | naphthalen-1-yl |
| phenyl | —CH₂CH₂CH₂O— | | naphthalen-1-yl |
| phenyl | (2-dimethyl amino)-eth-1-yl | 2-dimethyl amino-ethoxy | naphthalen-1-yl |
| phenyl | —CH₂C(=O)NEt₂ | —OCH₂C(=O)NEt₂ | naphthalen-1-yl |
| phenyl | —(CH₂)₂SC(=O)t-butyl | —O(CH₂)₂SC(=O)t-butyl | naphthalen-1-yl |
| 3,4-difluoro-phenyl | —CH₂OC(=O)t-butyl | CH₃ | 5-Cl-benzothiophen-3-yl |
| 3,4-difluoro-phenyl | (2-dimethyl amino)-eth-1-yl | CH₃ | 5-Cl-benzothiophen-3-yl |
| 3,4-difluoro-phenyl | (2-amino)-eth-1-yl | CH₃ | 5-Cl-benzothiophen-3-yl |
| 3,4-difluoro-phenyl | —CH₂O(=O)NEt₂ | CH₃ | 5-Cl-benzothiophen-3-yl |
| 3,4-difluoro-phenyl | —CH₂OC(=O)t-butyl | —OCH₂OC(=O)t-butyl | 5-Cl-benzothiophen-3-yl |
| 3,4-difluoro-phenyl | —CH₂OC(=O)t-butyl | OH | 5-Cl-benzothiophen-3-yl |
| 3,4-difluoro-phenyl | —CH₂C(=O)NEt₂ | —OCH₂C(=O)NEt2 | 5-Cl-benzothiophen-3-yl |
| 3,4-difluoro-phenyl | —CH₂CH₂CH₂O— | | 5-Cl-benzothiophen-3-yl |
| 3,4-difluoro-phenyl | —CH₂OC(=O)methyl | OH | 5-Cl-benzothiophen-3-yl |
| 3,4-difluoro-phenyl | —CH₂OC(=O)isopropyloxy | OH | 5-Cl-benzothiophen-3-yl |
| 2-methoxy-phenyl | H | OH | 5-Cl-benzothiophen-3-yl |
| pyridin-2-yl | H | OH | 5-Cl-benzothiophen-3-yl |
| 3-trifluoromethoxy-phenyl | H | OH | 5-Cl-benzothiophen-3-yl |
| 3-methoxy-phenyl | H | OH | 5-Cl-benzothiophen-3-yl |

-continued

| $R^2$, $R^3$ | $R^5$ | $R^6$ | $Z-R^4$ |
|---|---|---|---|
| 2,6-difluoro-phenyl | H | OH | 5-Cl-benzothiophen-3-yl |
| 2-chloro-phenyl | H | OH | 5-Cl-benzothiophen-3-yl |
| 3-chloro-phenyl | H | OH | 5-Cl-benzothiophen-3-yl |
| 3,5-difluoro-phenyl | H | OH | 5-Cl-benzothiophen-3-yl |
| 2,3-difluoro-phenyl | H | OH | 5-Cl-benzothiophen-3-yl |
| 2-bromo-phenyl | H | OH | 5-Cl-benzothiophen-3-yl |
| 2,3-dimethoxy-phenyl | H | OH | 5-Cl-benzothiophen-3-yl |
| 3-nitro-phenyl | H | OH | 5-Cl-benzothiophen-3-yl |
| 3-bromo-phenyl | H | OH | 5-Cl-benzothiophen-3-yl |
| 3,5-dimethoxy-phenyl | H | OH | 5-Cl-benzothiophen-3-yl |
| 2,5-difluoro-phenyl | H | OH | 5-Cl-benzothiophen-3-yl |
| 3,5-dichloro-phenyl | H | OH | 5-Cl-benzothiophen-3-yl |
| 2,4-difluoro-phenyl | H | OH | 5-Cl-benzothiophen-3-yl |
| 3-amino-phenyl | H | OH | 5-Cl-benzothiophen-3-yl |
| 2-methoxy-phenyl | —CH$_2$OC(=O) t-butyl | CH$_3$ | 5-Cl-benzothiophen-3-yl |
| pyridin-2-yl | —CH$_2$OC(=O) t-butyl | CH$_3$ | 5-Cl-benzothiophen-3-yl |
| 3-trifluoromethoxy-phenyl | —CH$_2$OC(=O)t-butyl | CH$_3$ | 5-Cl-benzothiophen-3-yl |
| 3-methoxy-phenyl | —CH$_2$OC(=O) t-butyl | CH$_3$ | 5-Cl-benzothiophen-3-yl |
| 2,6-difluoro-phenyl | —CH$_2$OC(=O) t-butyl | CH$_3$ | 5-Cl-benzothiophen-3-yl |
| 2-chloro-phenyl | —CH$_2$OC(=O) t-butyl | CH$_3$ | 5-Cl-benzothiophen-3-yl |
| 3-chloro-phenyl | —CH$_2$OC(=O) t-butyl | CH$_3$ | 5-Cl-benzothiophen-3-yl |
| 3,5-difluoro-phenyl | —CH$_2$OC(=O) t-butyl | CH$_3$ | 5-Cl-benzothiophen-3-yl |
| 2,3-difluoro-phenyl | —CH$_2$OC(=O) t-butyl | CH$_3$ | 5-Cl-benzothiophen-3-yl |
| 2-bromo-phenyl | —CH$_2$OC(=O) t-butyl | CH$_3$ | 5-Cl-benzothiophen-3-yl |
| 2,3-dimethoxy-phenyl | —CH$_2$OC(=O) t-butyl | CH$_3$ | 5-Cl-benzothiophen-3-yl |
| 3-nitro-phenyl | —CH$_2$OC(=O) t-butyl | CH$_3$ | 5-Cl-benzothiophen-3-yl |
| 3-bromo-phenyl | —CH$_2$OC(=O) t-butyl | CH$_3$ | 5-Cl-benzothiophen-3-yl |
| 3,5-dimethoxy-phenyl | —CH$_2$OC(=O) t-butyl | CH$_3$ | 5-Cl-benzothiophen-3-yl |
| 2,5-difluoro-phenyl | —CH$_2$OC(=O) t-butyl | CH$_3$ | 5-Cl-benzothiophen-3-yl |
| 3,5-dichloro-phenyl | —CH$_2$OC(=O) t-butyl | CH$_3$ | 5-Cl-benzothiophen-3-yl |
| 2,4-difluoro-phenyl | —CH$_2$OC(=O) t-butyl | CH$_3$ | 5-Cl-benzothiophen-3-yl |
| 3-amino-phenyl | —CH$_2$OC(=O) t-butyl | CH$_3$ | 5-Cl-benzothiophen-3-yl |
| 2-methoxy-phenyl | —CH$_2$OC(=O) t-butyl | —OCH$_2$OC(=O) t-butyl | 5-Cl-benzothiophen-3-yl |
| pyridin-2-yl | —CH$_2$OC(=O) t-butyl | —OCH$_2$OC(=O) t-butyl | 5-Cl-benzothiophen-3-yl |
| 3-trifluoromethoxy-phenyl | —CH$_2$OC(=O) t-butyl | —OCH$_2$OC(=O) t-butyl | 5-Cl-benzothiophen-3-yl |
| 3-methoxy-phenyl | —CH$_2$OC(=O) t-butyl | —OCH$_2$OC(=O) t-butyl | 5-Cl-benzothiophen-3-yl |
| 2,6-difluoro-phenyl | —CH$_2$OC(=O) t-butyl | —OCH$_2$OC(=O) t-butyl | 5-Cl-benzothiophen-3-yl |
| 2-chloro-phenyl | —CH$_2$OC(=O) t-butyl | —OCH$_2$OC(=O) t-butyl | 5-Cl-benzothiophen-3-yl |
| 3-chloro-phenyl | —CH$_2$OC(=O) t-butyl | —OCH$_2$OC(=O) t-butyl | 5-Cl-benzothiophen-3-yl |

|   R² R³ | R⁵ | R⁶ | Z-R⁴ |
|---|---|---|---|
| 3,5-difluoro-phenyl | —CH₂OC(=O)t-butyl | —OCH₂OC(=O)t-butyl | 5-Cl-benzothiophen-3-yl |
| 2,3-difluoro-phenyl | —CH₂OC(=O)t-butyl | —OCH₂OC(=O)t-butyl | 5-Cl-benzothiophen-3-yl |
| 2-bromo-phenyl | —CH₂OC(=O)t-butyl | —OCH₂OC(=O)t-butyl | 5-Cl-benzothiophen-3-yl |
| 2,3-dimethoxy-phenyl | —CH₂OC(=O)t-butyl | —OCH₂OC(=O)t-butyl | 5-Cl-benzothiophen-3-yl |
| 3-nitro-phenyl | —CH₂OC(=O)t-butyl | —OCH₂OC(=O)t-butyl | 5-Cl-benzothiophen-3-yl |
| 3-bromo-phenyl | —CH₂OC(=O)t-butyl | —OCH₂OC(=O)t-butyl | 5-Cl-benzothiophen-3-yl |
| 3,5-dimethoxy-phenyl | —CH₂OC(=O)t-butyl | —OCH₂OC(=O)t-butyl | 5-Cl-benzothiophen-3-yl |
| 2,5-difluoro-phenyl | —CH₂OC(=O)t-butyl | —OCH₂OC(=O)t-butyl | 5-Cl-benzothiophen-3-yl |
| 3,5-dichloro-phenyl | —CH₂OC(=O)t-butyl | —OCH₂OC(=O)t-butyl | 5-Cl-benzothiophen-3-yl |
| 2,4-difluoro-phenyl | —CH₂OC(=O)t-butyl | —OCH₂OC(=O)t-butyl | 5-Cl-benzothiophen-3-yl |
| 3-amino-phenyl | —CH₂OC(=O)t-butyl | —OCH₂OC(=O)t-butyl | 5-Cl-benzothiophen-3-yl |
| 2-methoxy-phenyl | —CH₂OC(=O)t-butyl | OH | 5-Cl-benzothiophen-3-yl |
| pyridin-2-yl | —CH₂OC(=O)t-butyl | OH | 5-Cl-benzothiophen-3-yl |
| 3-trifluoromethoxy-phenyl | —CH₂OC(=O)t-butyl | OH | 5-Cl-benzothiophen-3-yl |
| 3-methoxy-phenyl | —CH₂OC(=O)t-butyl | OH | 5-Cl-benzothiophen-3-yl |
| 2,6-difluoro-phenyl | —CH₂OC(=O)t-butyl | OH | 5-Cl-benzothiophen-3-yl |
| 2-chloro-phenyl | —CH₂OC(=O)t-butyl | OH | 5-Cl-benzothiophen-3-yl |
| 3-chloro-phenyl | —CH₂OC(=O)t-butyl | OH | 5-Cl-benzothiophen-3-yl |
| 3,5-difluoro-phenyl | —CH₂OC(=O)t-butyl | OH | 5-Cl-benzothiophen-3-yl |
| 2,3-difluoro-phenyl | —CH₂OC(=O)t-butyl | OH | 5-Cl-benzothiophen-3-yl |
| 2-bromo-phenyl | —CH₂OC(=O)t-butyl | OH | 5-Cl-benzothiophen-3-yl |
| 2,3-dimethoxy-phenyl | —CH₂OC(=O)t-butyl | OH | 5-Cl-benzothiophen-3-yl |
| 3-nitro-phenyl | —CH₂OC(=O)t-butyl | OH | 5-Cl-benzothiophen-3-yl |
| 3-bromo-phenyl | —CH₂OC(=O)t-butyl | OH | 5-Cl-benzothiophen-3-yl |
| 3,5-dimethoxy-phenyl | —CH₂OC(=O)t-butyl | OH | 5-Cl-benzothiophen-3-yl |
| 2,5-difluoro-phenyl | —CH₂OC(=O)t-butyl | OH | 5-Cl-benzothiophen-3-yl |
| 3,5-dichloro-phenyl | —CH₂OC(=O)t-butyl | OH | 5-Cl-benzothiophen-3-yl |
| 2,4-difluoro-phenyl | —CH₂OC(=O)t-butyl | OH | 5-Cl-benzothiophen-3-yl |
| 3-amino-phenyl | —CH₂OC(=O)t-butyl | OH | 5-Cl-benzothiophen-3-yl |
| 2-methoxy-phenyl | —CH₂CH₂CH₂O— | | 5-Cl-benzothiophen-3-yl |
| pyridin-2-yl | —CH₂CH₂CH₂O— | | 5-Cl-benzothiophen-3-yl |
| 3-trifluoromethoxy-phenyl | —CH₂CH₂CH₂O— | | 5-Cl-benzothiophen-3-yl |
| 3-methoxy-phenyl | —CH₂CH₂CH₂O— | | 5-Cl-benzothiophen-3-yl |
| 2,6-difluoro-phenyl | —CH₂CH₂CH₂O— | | 5-Cl-benzothiophen-3-yl |

| R², R³ | R⁵ | R⁶ | Z-R⁴ |
|---|---|---|---|
| 2-chloro-phenyl | —CH₂ CH₂ CH₂O— | | 5-Cl-benzothiophen-3-yl |
| 3-chloro-phenyl | —CH₂ CH₂ CH₂O— | | 5-Cl-benzothiophen-3-yl |
| 3,5-difluoro-phenyl | —CH₂ CH₂ CH₂O— | | 5-Cl-benzothiophen-3-yl |
| 2,3-difluoro-phenyl | —CH₂ CH₂ CH₂O— | | 5-Cl-benzothiophen-3-yl |
| 2-bromo-phenyl | —CH₂ CH₂ CH₂O— | | 5-Cl-benzothiophen-3-yl |
| 2,3-dimethoxy-phenyl | —CH₂ CH₂ CH₂O— | | 5-Cl-benzothiophen-3-yl |
| 3-nitro-phenyl | —CH₂ CH₂ CH₂O— | | 5-Cl-benzothiophen-3-yl |
| 3-bromo-phenyl | —CH₂ CH₂ CH₂O— | | 5-Cl-benzothiophen-3-yl |
| 3,5-dimethoxy-phenyl | —CH₂ CH₂ CH₂O— | | 5-Cl-benzothiophen-3-yl |
| 2,5-difluoro-phenyl | —CH₂ CH₂ CH₂O— | | 5-Cl-benzothiophen-3-yl |
| 3,5-dichloro-phenyl | —CH₂ CH₂ CH₂O— | | 5-Cl-benzothiophen-3-yl |
| 2,4-difluoro-phenyl | —CH₂ CH₂ CH₂O— | | 5-Cl-benzothiophen-3-yl |
| 3-amino-phenyl | —CH₂ CH₂ CH₂O— | | 5-Cl-benzothiophen-3-yl |
| 2-methoxy-phenyl | —CH₂OC(=O) isopropyloxy | OH | 5-Cl-benzothiophen-3-yl |
| pyridin-2-yl | —CH₂OC(=O) isopropyloxy | OH | 5-Cl-benzothiophen-3-yl |
| 3-trifluoromethoxy-phenyl | —CH₂OC(=O) isopropyloxy | OH | 5-Cl-benzothiophen-3-yl |
| 3-methoxy-phenyl | —CH₂OC(=O) isopropyloxy | OH | 5-Cl-benzothiophen-3-yl |
| 2,6-difluoro-phenyl | —CH₂OC(=O) isopropyloxy | OH | 5-Cl-benzothiophen-3-yl |
| 2-chloro-phenyl | —CH₂OC(=O) isopropyloxy | OH | 5-Cl-benzothiophen-3-yl |
| 3-chloro-phenyl | —CH₂OC(=O) isopropyloxy | OH | 5-Cl-benzothiophen-3-yl |
| 3,5-difluoro-phenyl | —CH₂OC(=O) isopropyloxy | OH | 5-Cl-benzothiophen-3-yl |
| 2,3-difluoro-phenyl | —CH₂OC(=O) isopropyloxy | OH | 5-Cl-benzothiophen-3-yl |
| 2-bromo-phenyl | —CH₂OC(=O) isopropyloxy | OH | 5-Cl-benzothiophen-3-yl |
| 2,3-dimethoxy-phenyl | —CH₂OC(=O) isopropyloxy | OH | 5-Cl-benzothiophen-3-yl |
| 3-nitro-phenyl | —CH₂OC(=O) isopropyloxy | OH | 5-Cl-benzothiophen-3-yl |
| 3-bromo-phenyl | —CH₂OC(=O) isopropyloxy | OH | 5-Cl-benzothiophen-3-yl |
| 3,5-dimethoxy-phenyl | —CH₂OC(=O) isopropyloxy | OH | 5-Cl-benzothiophen-3-yl |
| 2,5-difluoro-phenyl | —CH₂OC(=O) isopropyloxy | OH | 5-Cl-benzothiophen-3-yl |
| 3,5-dichloro-phenyl | —CH₂OC(=O) isopropyloxy | OH | 5-Cl-benzothiophen-3-yl |
| 2,4-difluoro-phenyl | —CH₂OC(=O) isopropyloxy | OH | 5-Cl-benzothiophen-3-yl |
| 3-amino-phenyl | —CH₂OC(=O) isopropyloxy | OH | 5-Cl-benzothiophen-3-yl |
| 3-fluoro-5-chloro-phenyl | H | CH₃ | 5-Cl-benzothiophen-3-yl |
| 2-fluoro-3-chloro-phenyl | H | CH₃ | 5-Cl-benzothiophen-3-yl |
| 4-fluoro-3-chloro-phenyl | H | CH₃ | 5-Cl-benzothiophen-3-yl |
| 2-fluoro-5-chloro-phenyl | H | CH₃ | 5-Cl-benzothiophen-3-yl |
| 3,5-dibromo-phenyl | H | CH₃ | 5-Cl-benzothiophen-3-yl |
| 3-cyano-phenyl | H | CH₃ | 5-Cl-benzothiophen-3-yl |
| 2-cyano-phenyl | H | CH₃ | 5-Cl-benzothiophen-3-yl |
| 3-fluoro-5-trifluoromethyl-phenyl | H | CH₃ | 5-Cl-benzothiophen-3-yl |
| 3-fluoro-5-chloro-phenyl | H | OH | 5-Cl-benzothiophen-3-yl |
| 2-fluoro-3-chloro-phenyl | H | OH | 5-Cl-benzothiophen-3-yl |
| 4-fluoro-3-chloro-phenyl | H | OH | 5-Cl-benzothiophen-3-yl |
| 2-fluoro-5-chloro-phenyl | H | OH | 5-Cl-benzothiophen-3-yl |

-continued

| $R^2$ $R^3$ | $R^5$ | $R^6$ | $Z-R^4$ |
|---|---|---|---|
| 3,5-dibromo-phenyl | H | OH | 5-Cl-benzothiophen-3-yl |
| 3-cyano-phenyl | H | OH | 5-Cl-benzothiophen-3-yl |
| 2-cyano-phenyl | H | OH | 5-Cl-benzothiophen-3-yl |
| 3-fluoro-5-trifluoromethyl-phenyl | H | OH | 5-Cl-benzothiophen-3-yl |
| 3-fluoro-5-chloro-phenyl | —CH$_2$OC(=O) t-butyl | CH$_3$ | 5-Cl-benzothiophen-3-yl |
| 2-fluoro-3-chloro-phenyl | —CH$_2$OC(=O) t-butyl | CH$_3$ | 5-Cl-benzothiophen-3-yl |
| 4-fluoro-3-chloro-phenyl | —CH$_2$OC(=O) t-butyl | CH$_3$ | 5-Cl-benzothiophen-3-yl |
| 2-fluoro-5-chloro-phenyl | —CH$_2$OC(=O) t-butyl | CH$_3$ | 5-Cl-benzothiophen-3-yl |
| 3,5-dibromo-phenyl | —CH$_2$OC(=O) t-butyl | CH$_3$ | 5-Cl-benzothiophen-3-yl |
| 3-cyano-phenyl | —CH$_2$OC(=O) t-butyl | CH$_3$ | 5-Cl-benzothiophen-3-yl |
| 2-cyano-phenyl | —CH$_2$OC(=O) t-butyl | CH$_3$ | 5-Cl-benzothiophen-3-yl |
| 3-fluoro-5-trifluoromethyl-phenyl | —CH$_2$OC(=O) t-butyl | CH$_3$ | 5-Cl-benzothiophen-3-yl |
| 3-fluoro-5-chloro-phenyl | —CH$_2$OC(=O) t-butyl | —OCH$_2$OC(=O) t-butyl | 5-Cl-benzothiophen-3-yl |
| 2-fluoro-3-chloro-phenyl | —CH$_2$OC(=O) t-butyl | —OCH$_2$OC(=O) t-butyl | 5-Cl-benzothiophen-3-yl |
| 4-fluoro-3-chloro-phenyl | —CH$_2$OC(=O) t-butyl | —OCH$_2$OC(=O) t-butyl | 5-Cl-benzothiophen-3-yl |
| 2-fluoro-5-chloro-phenyl | —CH$_2$OC(=O) t-butyl | —OCH$_2$OC(=O) t-butyl | 5-Cl-benzothiophen-3-yl |
| 3,5-dibromo-phenyl | —CH$_2$OC(=O) t-butyl | —OCH$_2$OC(=O) t-butyl | 5-Cl-benzothiophen-3-yl |
| 3-cyano-phenyl | —CH$_2$OC(=O) t-butyl | —OCH$_2$OC(=O) t-butyl | 5-Cl-benzothiophen-3-yl |
| 2-cyano-phenyl | —CH$_2$OC(=O) t-butyl | —OCH$_2$OC(=O) t-butyl | 5-Cl-benzothiophen-3-yl |
| 3-fluoro-5-trifluoromethyl-phenyl | —CH$_2$OC(=O) t-butyl | —OCH$_2$OC(=O) t-butyl | 5-Cl-benzothiophen-3-yl |
| 3-fluoro-5-chloro-phenyl | —CH$_2$OC(=O) t-butyl | OH | 5-Cl-benzothiophen-3-yl |
| 2-fluoro-3-chloro-phenyl | —CH$_2$OC(=O) t-butyl | OH | 5-Cl-benzothiophen-3-yl |
| 4-fluoro-3-chloro-phenyl | —CH$_2$OC(=O) t-butyl | OH | 5-Cl-benzothiophen-3-yl |
| 2-fluoro-5-chloro-phenyl | —CH$_2$OC(=O) t-butyl | OH | 5-Cl-benzothiophen-3-yl |
| 3,5-dibromo-phenyl | —CH$_2$OC(=O) t-butyl | OH | 5-Cl-benzothiophen-3-yl |
| 3-cyano-phenyl | —CH$_2$OC(=O) t-butyl | OH | 5-Cl-benzothiophen-3-yl |
| 2-cyano-phenyl | —CH$_2$OC(=O) t-butyl | OH | 5-Cl-benzothiophen-3-yl |
| 3-fluoro-5-trifluoromethyl-phenyl | —CH$_2$OC(=O) t-butyl | OH | 5-Cl-benzothiophen-3-yl |
| 3-fluoro-5-chloro-phenyl | —CH$_2$ CH$_2$ CH$_2$O— | | 5-Cl-benzothiophen-3-yl |
| 2-fluoro-3-chloro-phenyl | —CH$_2$ CH$_2$ CH$_2$O— | | 5-Cl-benzothiophen-3-yl |
| 4-fluoro-3-chloro-phenyl | —CH$_2$ CH$_2$ CH$_2$O— | | 5-Cl-benzothiophen-3-yl |
| 2-fluoro-5-chloro-phenyl | —CH$_2$ CH$_2$ CH$_2$O— | | 5-Cl-benzothiophen-3-yl |
| 3,5-dibromo-phenyl | —CH$_2$ CH$_2$ CH$_2$O— | | 5-Cl-benzothiophen-3-yl |

-continued

| A (R², R³) | R⁵ | R⁶ | Z-R⁴ |
|---|---|---|---|
| 3-cyano-phenyl | —CH₂CH₂CH₂O— | | 5-Cl-benzothiophen-3-yl |
| 2-cyano-phenyl | —CH₂CH₂CH₂O— | | 5-Cl-benzothiophen-3-yl |
| 3-fluoro-5-trifluoromethyl-phenyl | —CH₂CH₂CH₂O— | | 5-Cl-benzothiophen-3-yl |
| 3-fluoro-5-chloro-phenyl | —CH₂OC(=O)isopropyloxy | OH | 5-Cl-benzothiophen-3-yl |
| 2-fluoro-3-chloro-phenyl | —CH₂OC(=O)isopropyloxy | OH | 5-Cl-benzothiophen-3-yl |
| 4-fluoro-3-chloro-phenyl | —CH₂OC(=O)isopropyloxy | OH | 5-Cl-benzothiophen-3-yl |
| 2-fluoro-5-chloro-phenyl | —CH₂OC(=O)isopropyloxy | OH | 5-Cl-benzothiophen-3-yl |
| 3,5-dibromo-phenyl | —CH₂OC(=O)isopropyloxy | OH | 5-Cl-benzothiophen-3-yl |
| 3-cyano-phenyl | —CH₂OC(=O)isopropyloxy | OH | 5-Cl-benzothiophen-3-yl |
| 2-cyano-phenyl | —CH₂OC(=O)isopropyloxy | OH | 5-Cl-benzothiophen-3-yl |
| 3-fluoro-5-trifluoromethyl-phenyl | —CH₂OC(=O)isopropyloxy | OH | 5-Cl-benzothiophen-3-yl |

In an embodiment, the present invention is directed to a process for the preparation of a compound of formula (I) selected from the group consisting of:

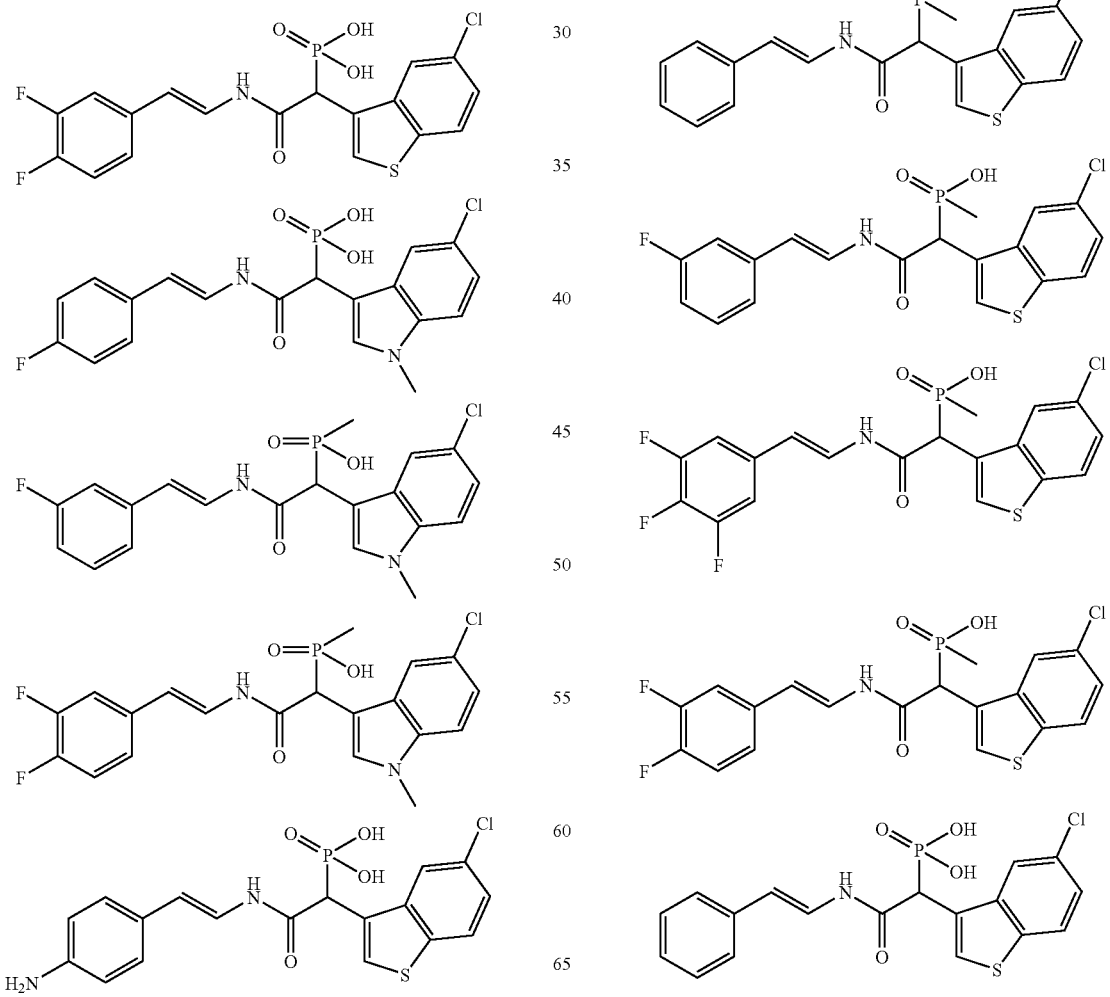

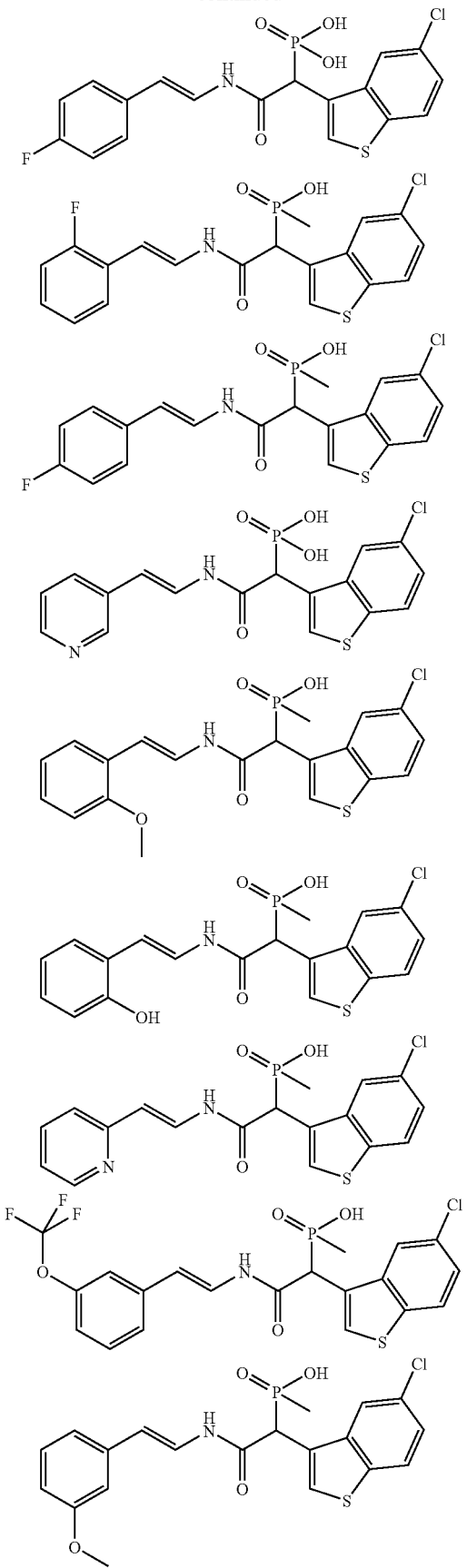
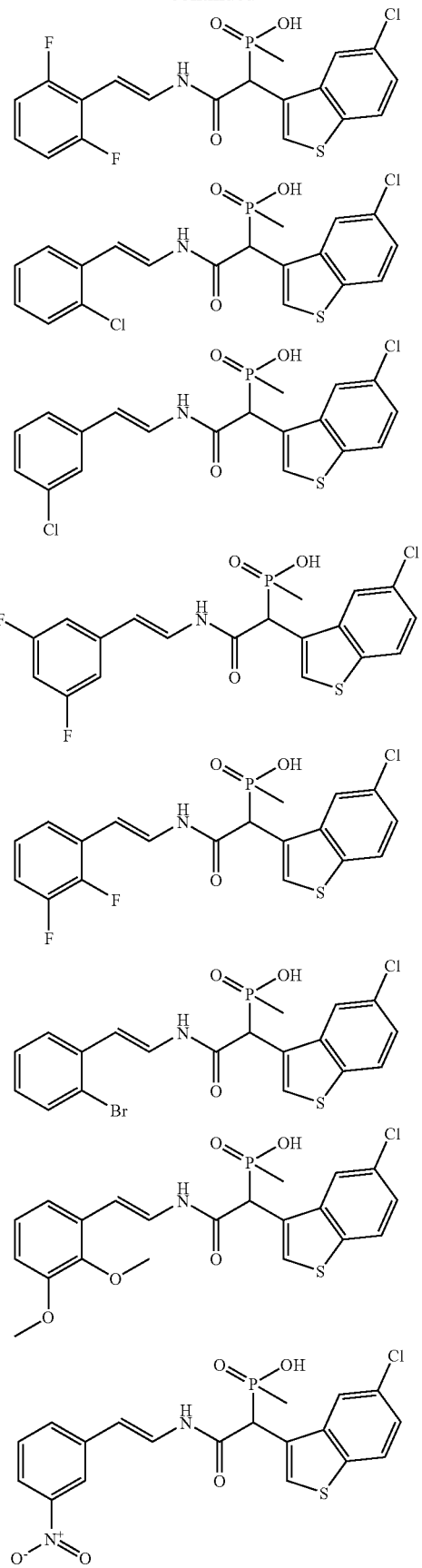

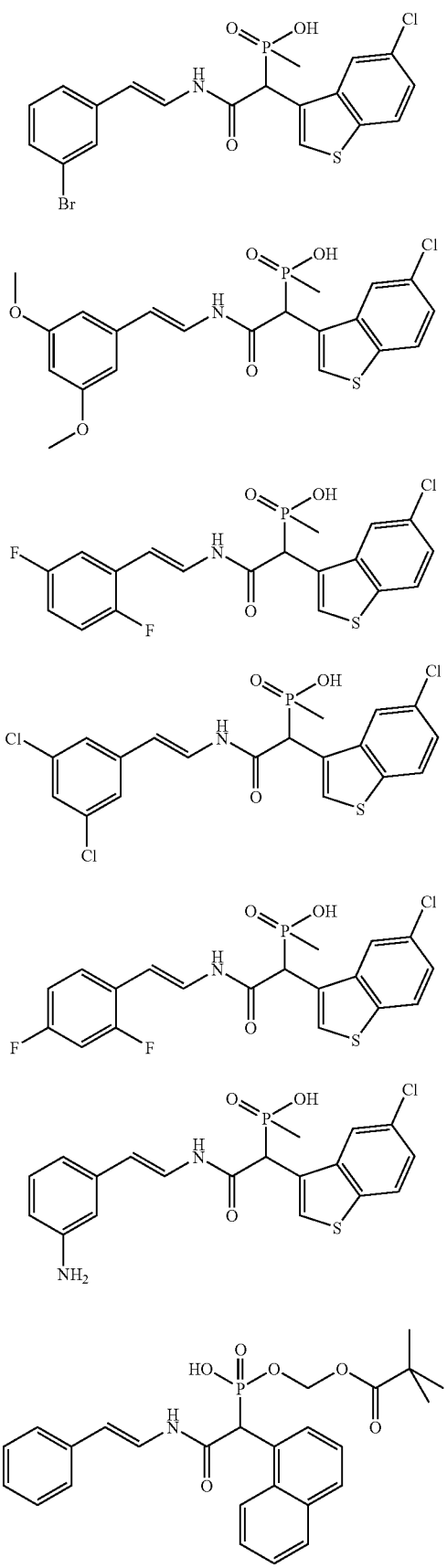
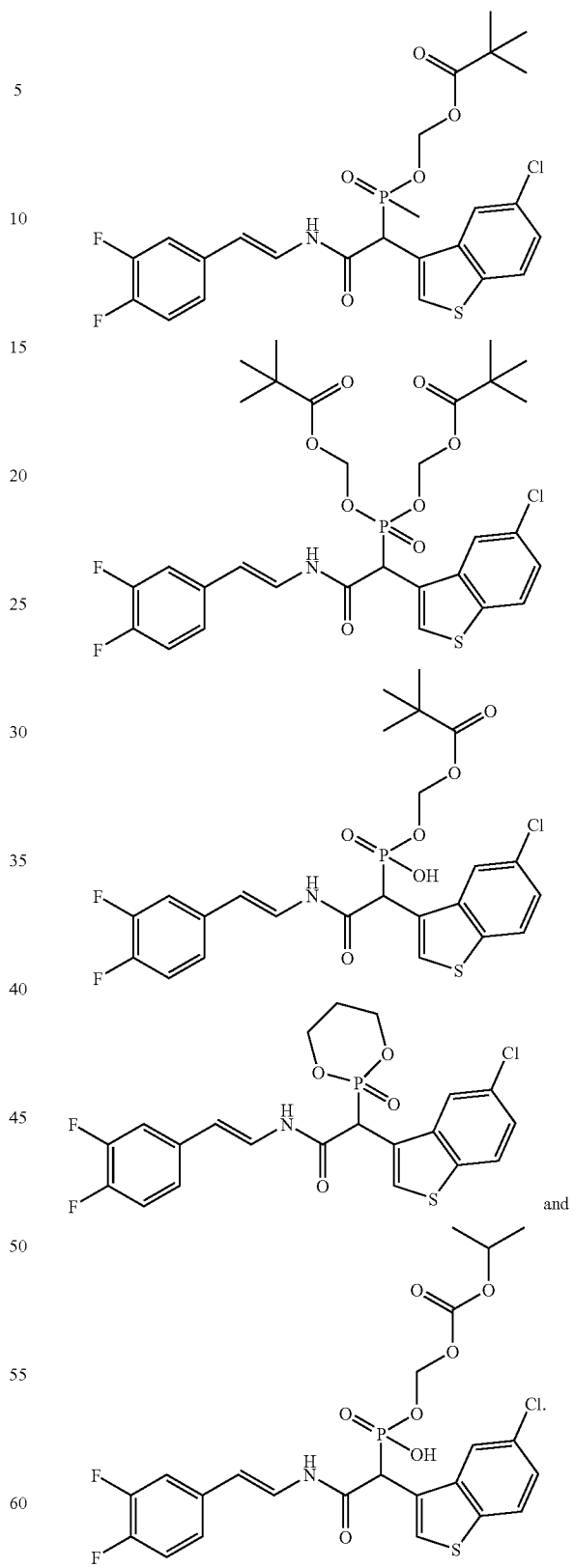
In another embodiment, the present invention is directed to a process for the preparation of a compound of formula (I) selected from the group consisting of:

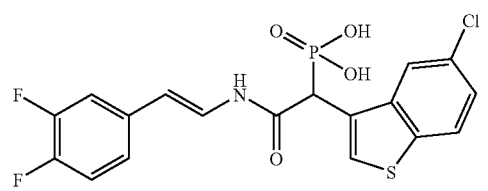
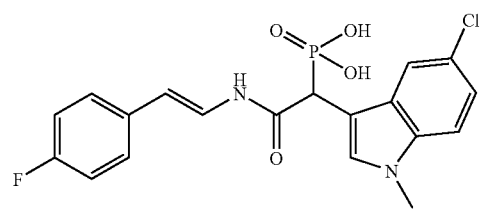
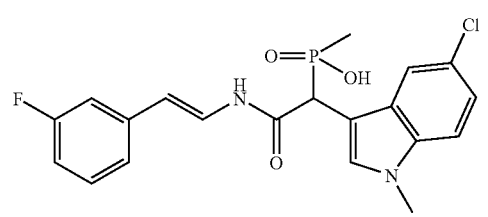
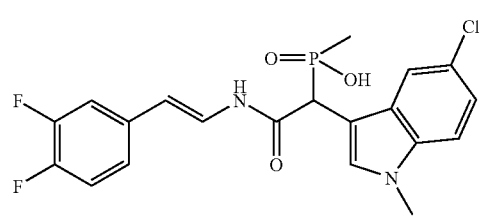
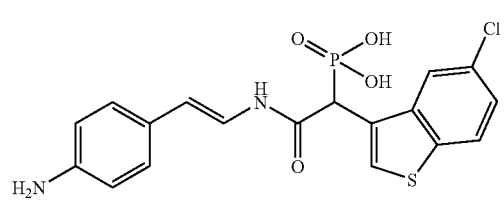
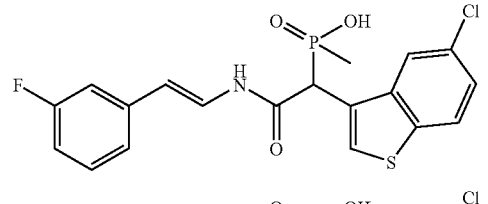
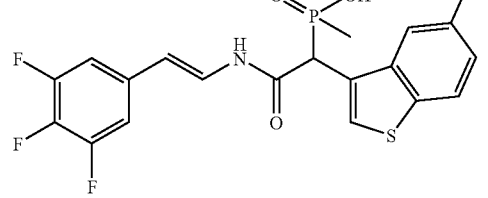
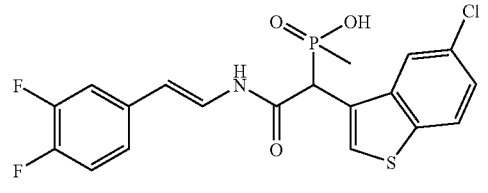
-continued
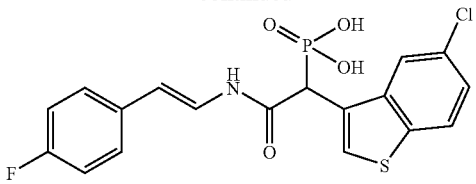
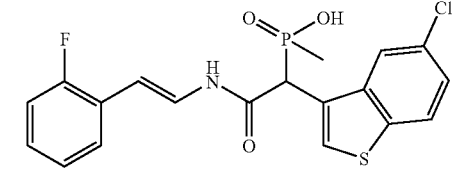
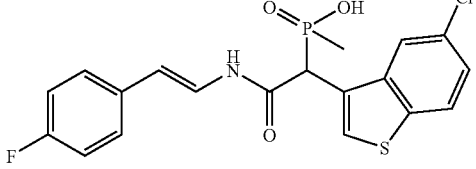
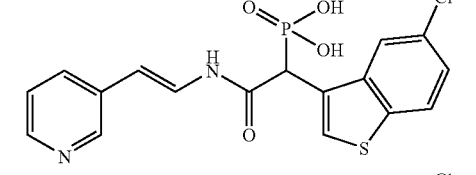
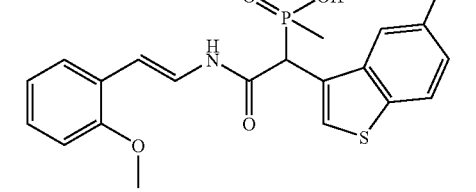
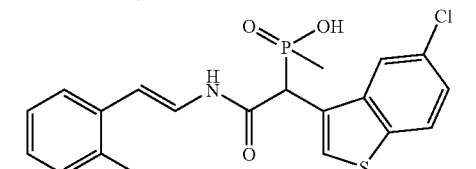
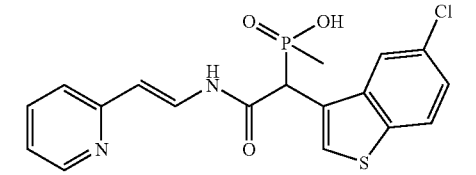
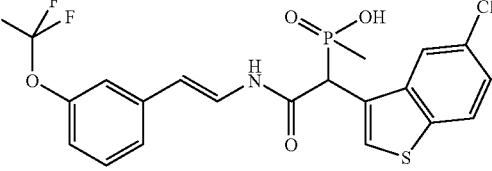
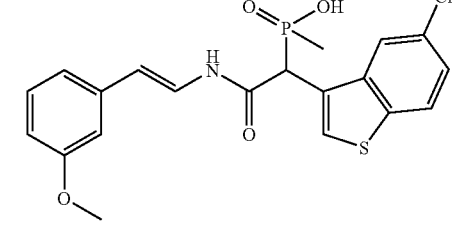

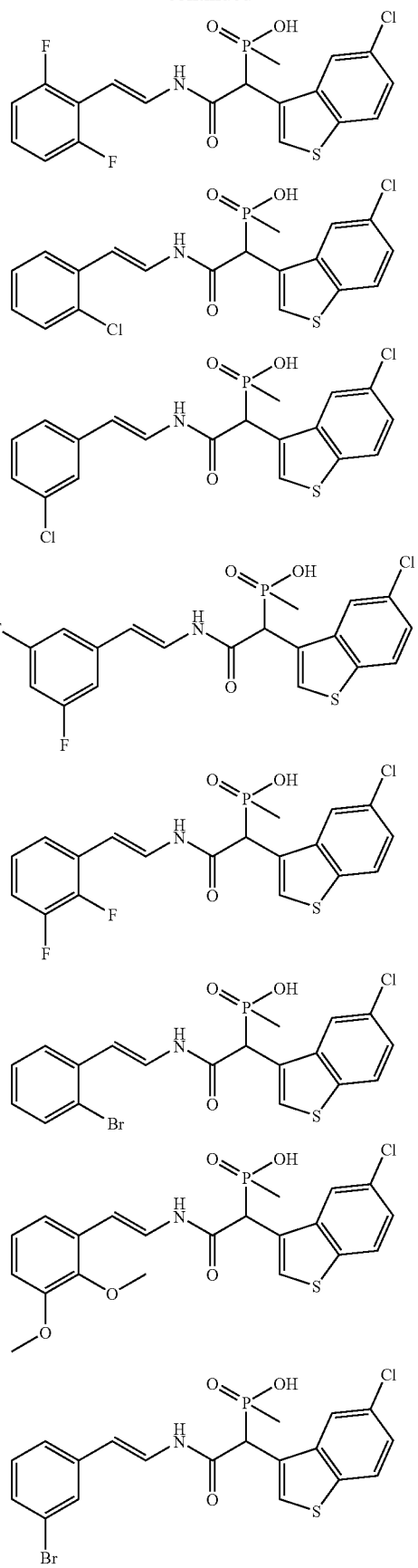
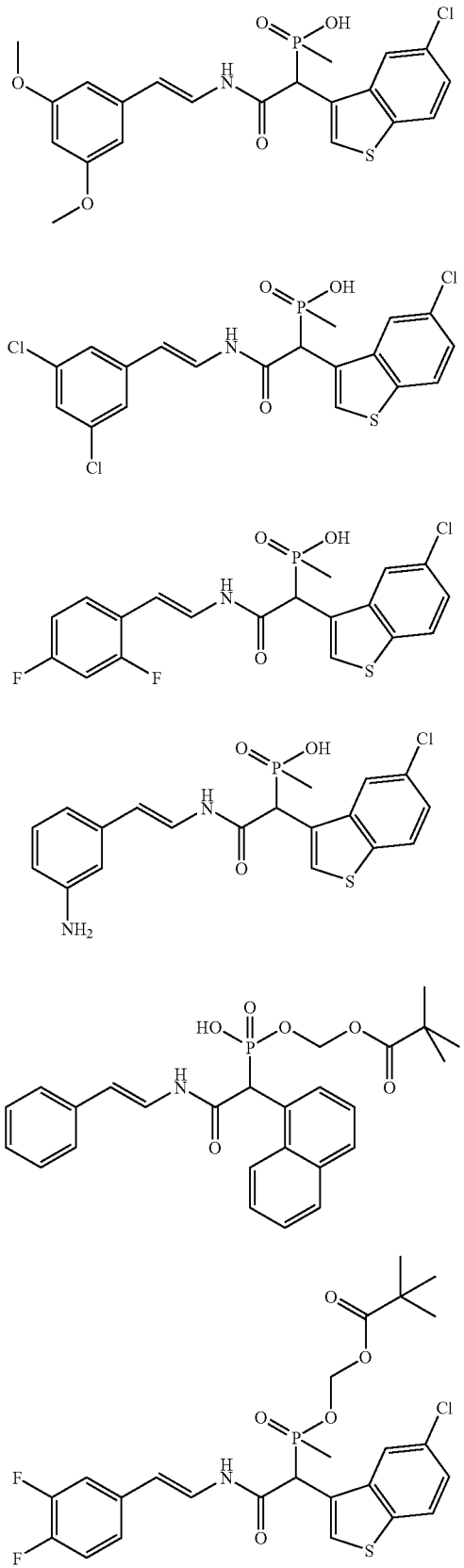

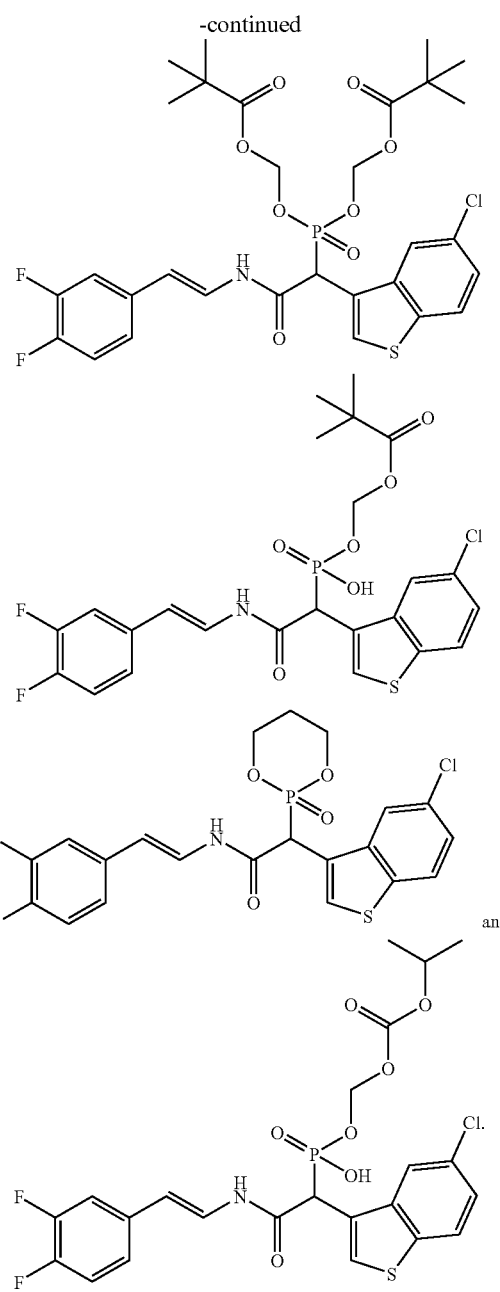

In an embodiment, the present invention is directed to a process for the preparation of a compound of formula (I) wherein ring A, $R^2$, $R^3$, $R^5$, $R^6$, Z, and $R^4$ are selected from the group consisting of:

| Formula | $R^2$  A  $R^3$ | $R^5$ | $R^6$ | Z-$R^4$ |
|---|---|---|---|---|
| (I-A) | 3,4-difluoro-phenyl | H | CH$_3$ | 5-chloro-benzo-thiophen-3-yl |
| (I-B) | 3,4-difluoro-phenyl | H | OH | 5-chloro-benzo-thiophen-3-yl |
| (I-C) | 3,4-difluoro-phenyl | —CH$_2$OC(O)-t-butyl | OH | 5-chloro-benzo-thiophen-3-yl |
| (I-D) | 3,4-difluoro-phenyl | —CH$_2$OC(O)-isopropyloxy | OH | 5-chloro-benzo-thiophen-3-yl |
| (I-E) | 3,5-dichloro-phenyl | H | CH$_3$ | 5-chloro-benzo-thiophen-3-yl |
| (I-F) | 3,5-dichloro-phenyl | H | OH | 5-chloro-benzo-thiophen-3-yl |
| (I-G) | 3,5-dichloro-phenyl | —CH$_2$OC(O)-t-butyl | OH | 5-chloro-benzo-thiophen-3-yl |
| (I-H) | 3,5-dichloro-phenyl | —CH$_2$OC(O)-isopropyloxy | OH | 5-chloro-benzo-thiophen-3-yl. |

In yet another embodiment, the present invention is directed to a process for the preparation of a compound of formula (I) selected from the group consisting of

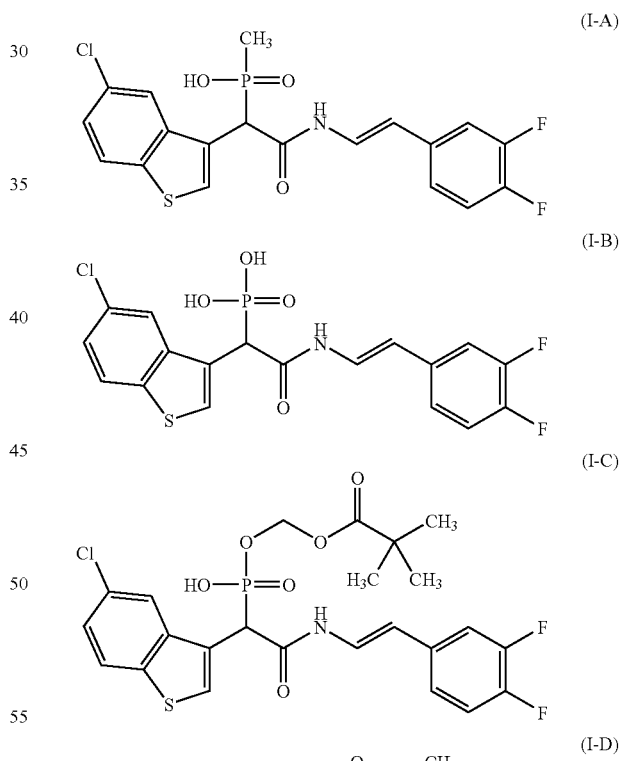

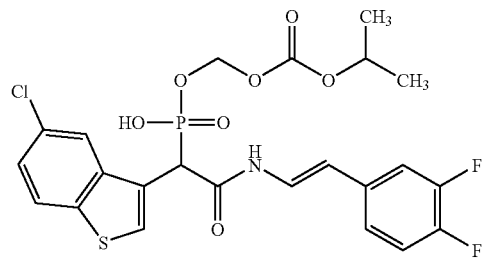

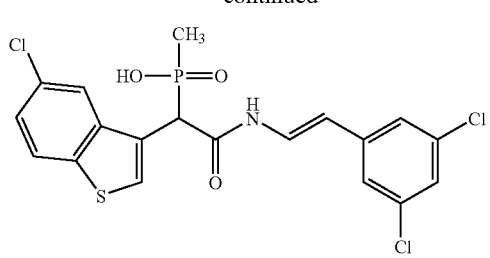
(I-E)

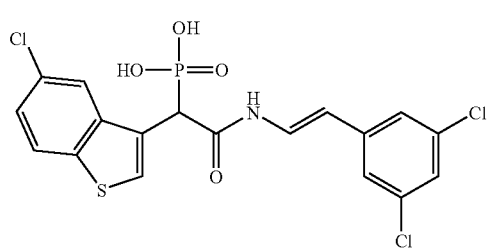
(I-F)

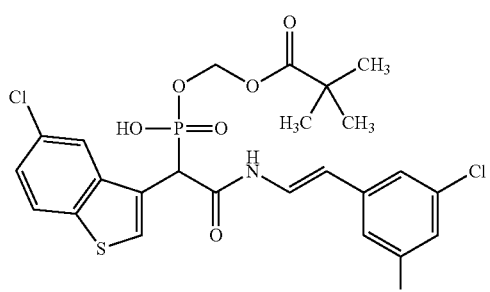
(I-G)

and

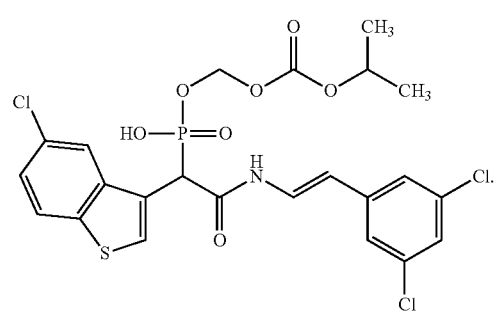
(I-H)

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a terminal carbon atom or, when acting as a linking group, within the carbon chain.

The term "cycloalkyl" refers to saturated or partially unsaturated, moncyclic or polycyclic hydrocarbon rings of from 3 to 20 carbon atom members (preferably from 3 to 14 carbon atom members). Further, a cycloalkyl ring may optionally be fused to one or more cycloalkyl rings. Examples of such rings include, and are not limited to, cyclopropyl, cyclobutyl, cyclopentyl, cyclohexyl, cycloheptyl, and adamantyl.

The term "heterocyclyl" refers to a nonaromatic cyclic ring of 5 to 10 members in which 1 to 4 members are nitrogen or a nonaromatic cyclic ring of 5 to 10 members in which zero, one or two members are nitrogen and up to two members is oxygen or sulfur; wherein, optionally, the ring contains zero, one or two unsaturated bonds. Alternatively, the heterocyclyl ring may be fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, the heterocyclyl can be bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl, and piperazinyl.

The term "aryl" refers to an unsaturated, aromatic monocyclic ring of 6 carbon members or to an unsaturated, aromatic polycyclic ring of from 10 to 20 carbon members. Examples of such aryl rings include, and are not limited to, phenyl, naphthalenyl and anthracenyl. Preferred aryl groups for the practice of this invention are phenyl and naphthalenyl.

The term "benzo fused cycloalkyl" refers to a bicyclic or tricyclic ring structure wherein at least one of the ring substituents is phenyl or naphthalenyl and at least one of the other substituents is a cycloalkyl ring (as cycloalkyl was previously defined). For the purpose of these definitions, the cycloalkyl rings may be fused to an additional benzene ring (to provide fused multiple ring systems such as fluorene). Example of such benzo fused cycloalkyls include, but are not limited to, indanyl, 1,2,3,4-tetrahydronaphthalenyl and fluorenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. Optionally, the heteroaryl ring is fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclo ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl, and quinazolinyl.

The term "arylalkyl" means an alkyl group substituted with an aryl group (e.g., benzyl and phenethyl). Similarly, the term "arylalkoxy" indicates an alkoxy group substituted with an aryl group (e.g., benzyloxy).

The term "halogen" refers to fluorine, chlorine, bromine, and iodine. Substituents that are substituted with multiple halogens are substituted in a manner that provides compounds which are stable.

Whenever the term "alkyl" or "aryl" or either of their prefix roots appear in a name of a substituent (e.g., arylalkyl and alkylamino), it shall be interpreted as including those limitations given above for "alkyl" and "aryl." Designated numbers of carbon atoms (e.g., $C_1-C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.). However, for clarity in the terms "$C_9-C_{14}$ benzo fused cycloalkyl", "$C_9-C_{14}$ benzo fused cycloalkenyl", "$C_9-C_{14}$ benzo fused aryl"; $C_9-C_{14}$ refers to the number of carbon atoms both in the benzene ring (6) and the number of atoms in the ring fused to the benzene ring, but does not include carbon atoms that may be pendent from these multiple ring systems. The amount of substituents attached to a moiety "optionally substituted with one to five substituents" is limited to that amount of open valences on the moiety available for substitution.

When a particular group is "substituted" (e.g., alkkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Similarly, wherein a compound of the present invention comprises one or more double bonds, said double bond(s) may each be independently present in a cis or trans configuration (also sometimes referred to as in an "Z" or "E" configurations, respectively). It is to be understood that cis and trans geometric isomers and all mixtures thereof are encompassed within the scope of the present invention. Wherein a compound comprising a single double bound is present in an excess of one of its corresponding geometric isomers (for example, in an excess of its corresponding trans isomer), said compound is preferably present such that the desired geometric isomer is present in amount of greater than about 50%, Further, more preferably, greater than about 75%, more preferably, greater than about 90%, more preferably, greater than about 95%, most preferably, greater than about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

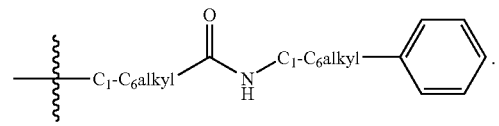

Abbreviations used in the specification, particularly the Schemes and Examples, are as follows

| | |
|---|---|
| DCE = | Dichloroethane |
| DCM = | Dichloromethane |
| DIPEA or DIEA = | Diisopropylethylamine |
| DMA or DMAc = | N,N-Dimethylacetamide |
| DME = | 1,2-Dimethoxyethane |
| DMF = | N,N-Dimethylformamide |
| EtOAc = | Ethyl acetate |
| HPLC = | High Pressure Liquid Chromatography |
| LiHMDS = | Lithium bis(trimethylsilyl)amide |
| Mn(OAc)$_2$ = | Manganese Acetate |
| MTBE = | Methyl t-Butyl Ether |
| NaHMDS = | Sodium bis(trimethylsilyl)amide |
| NBS = | N-bromosuccinimide |
| NMP = | N-methyl-2-pyrrolidinone |
| NH$_4$OAc = | Ammonium Acetate |
| TEA = | Triethylamine |
| THF = | Tetrahydrofuran |
| TLC = | Thin Layer Chromatography |
| TMS-Br = | Bromotrimethylsilane |
| TMS-Cl = | Chlorotrimetylsilane |
| TMS-I = | Iodotrimethylsilane |

As used herein, unless otherwise noted, the term "isolated form" shall mean that the compound is present in a form which is separate from any solid mixture with another compound(s), solvent system or biological environment. In an embodiment of the present invention, the compound of formula (I) is prepared as an isolated form. In additional embodiments of the present invention, the compound of formula (I-A), (I-B), (I-C), (I-D), (I-E), (I-F), (I-G) and/or (I-H) is prepared as an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is prepared as a substantially pure form. In additional embodiments of the present invention, the compounds of formula (I-A), (I-B), (I-C), (I-D), (I-E), (I-F), (I-G) and/or (I-H) is prepared as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is prepared in a form which is substantially free of corresponding salt form(s). In additional embodiments of the present invention, the compound of formula (I-A), (I-B), (I-C), (I-D), (I-E), (I-F), (I-G) and/or (I-H) is prepared in a form which is substantially free of corresponding salt form(s).

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The compounds of formula (I) (disclosed as in U.S. Pat. No. 7,459,444, issued Dec. 2, 2008, which is incorporated by reference herein in its entirety), prepared according to the process of the present invention, are useful serine protease inhibitors (in particular, inhibitors of chymase) useful for treating inflammatory, and serine protease mediated disorders. Serine proteases such as chymase produced by mast cells have been recognized to be involved in a variety of inflammatory and wound healing events (e.g., angiogenesis, collagen deposition and cell proliferation). Chymase plays these roles by activating a variety of pre-existing factors present in the microenvironment surrounding the mast cells. For example, just to name a few of these interactions chymase activates SCF, angiotensin I to angiotensin II, endothelin 1, type 1 procollagen, metalloprotienases, IL-1B, TGF-β, as well as, degrades the extracellular matrix (de Paulis et al. Int Arch Allerg Immunol 118 (1999) 422-425; Longley et al. Proc Natl Acad Sci USA 94 (1997) 9017-9021). Consequently, the release of chymase plays significant role in a variety of pathological conditions associated with vascular proliferation, fibrosis, tissue remodeling, inflammation, and the like.

Some of these, inflammatory and serine protease mediated disorders include, and are not limited to, allergic rhinitis, viral rhinitis, asthma, chronic obstructive pulmonary diseases, bronchitis, pulmonary emphysema, acute lung injury (e.g. adult (acute) respiratory distress syndrome), psoriasis, arthritis, reperfusion injury, ischemia, hypertension, hypercardia, myocardial infarction, heart failure damage associated with myocardial infarction, cardiac hypertrophy, arteriosclerosis, saroidosis, vascular stenosis or restenosis (e.g., associated with vascular injury, angioplasty, vascular stents or vascular grafts), pulmonary fibrosis, kidney fibrosis (e.g., associated with glomerulonephritis), liver fibrosis, post surgical adhesion formation, systemic sclerosis, keloid scars rheumatoid arthritis, bullous pemphigiod and atherosclerosis. Additionally, these compounds can be used for modulating wound healing and remodeling (e.g., cardiac hypertrophy) as well as immune modulation.

One skilled in the art will recognize that, where not otherwise specified, the reaction step(s) is performed under suitable conditions, according to known methods, to provide the desired product.

One skilled in the art will recognize that, in the specification and claims as presented herein, wherein a substituent group (e.g. protecting group such as $PG^1$ or $PG^2$; activating group such as $Y^1$; leaving group such as $Q^1$; alkyl substituent such as $A^1$; etc.) or reagent or reagent class/type (e.g. base, solvent, etc.) is recited in more than one step of a process, or in more than one process, the individual substituent groups and reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

One skilled in the art will recognize that in the processes as described herein it may be advantageous and/or desirable to protected terminal substituent groups such as hydroxy, alkoxy, alkylcarbonyloxy, alkoxycarbonyloxy, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

The processes of the present invention may be used in the preparation of compounds which act as prodrugs of the compounds of formula (I). In general, such prodrugs will be functional derivatives of the compounds which are readily convertible in vivo into the required pharmaceutically active compound. Thus, in the methods of treatment of the present invention, the term "administering" shall encompass the treatment of the various disorders described with the compound specifically disclosed or with a compound which may not be specifically disclosed, but which converts to the specified pharmaceutically active compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention is directed to a process for the preparation of a compound of formula (III), as outlined in more detail in Scheme 1, which follows herein. The compound of formula (III) is useful as an intermediate in the synthesis of, for example, a compound of formula (I-A), a compound of formula (I-B), a compound of formula (I-C) and/or a compound of formula (I-D).

In some embodiments, the present invention is directed to processes for the preparation of compounds of formula (L), more particularly to process for the preparation of compounds of formula (IX) and compounds of formula (XV), as described in more detail in Schemes 2 through 5, which follow herein. The compounds of formula (L), and more particularly the compounds of formula (IX) and the compounds of formula (XV), are useful as intermediates in the synthesis of compounds of formula (I).

In some embodiments, the present invention is directed to processes for the preparation of the compounds of formula (I), as described in more detail in Schemes 6 through 9, which follow herein. The compounds of formula (I) are useful as chymase modulators, as described in more detail herein. In additional embodiments, the present invention is directed to processes for the preparation of the compounds of formula (I-A), (I-B), (I-C), (I-D), (I-E), (I-F), (I-G) and (I-H), as described in more detail in Schemes 10 through 17, which follow herein.

The present invention is directed to a process for the preparation of a compound of formula (III), as outlined in Scheme 1, below.

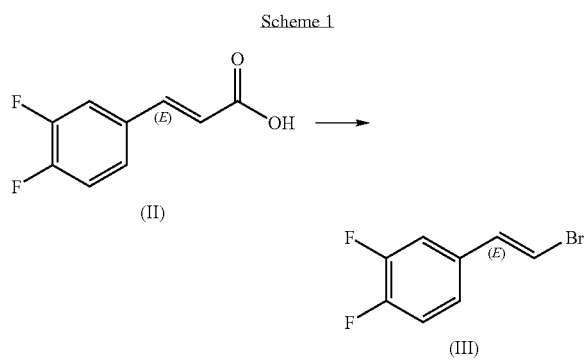

Accordingly, a suitably substituted compound of formula (II), a known compound or compound prepared by known methods, wherein the compound of formula (II) is preferably present in an excess of its corresponding trans form, more preferably present as its corresponding trans form; is reacted with a suitably selected brominating agent such as 1-bromo-pyrrolidine-2,5-dione, bromine gas, dibromohydantoin, and the like, preferably, 1-bromo-pyrrolidine-2,5-dione; wherein the brominating agent is preferably present in an amount in the range of from about 0.5 to about 2.0 molar equivalents (relative to the moles of the compound of formula (II), more preferably in an amount in the range of from about 0.8 to about 1.2 molar equivalents, more preferably still in an amount of about 1.1 molar equivalents;

in the presence of a suitably selected catalyst such as lithium acetate, manganese acetate hydrate, magnesium acetate, and the like, preferably manganese acetate hydrate; wherein the catalyst is preferably present in an amount in the range of from about 0.2 to about 1.0 molar equivalents (relative to the moles of the compound of formula (II), more preferably in an amount in the range of from about 0.3 to about 0.8 molar equivalents, more preferably still in an amount of about 0.5 molar equivalents;

in a mixture of water and an organic solvent such as acetonitrile, THF, and the like, preferably acetonitrile; preferably at a temperature in the range of from about 25° C. to about 70° C.; to yield the corresponding compound of formula (III).

The present invention is further directed to processes for the preparation of compounds of formula (IX) as outlined in Scheme 2, below.

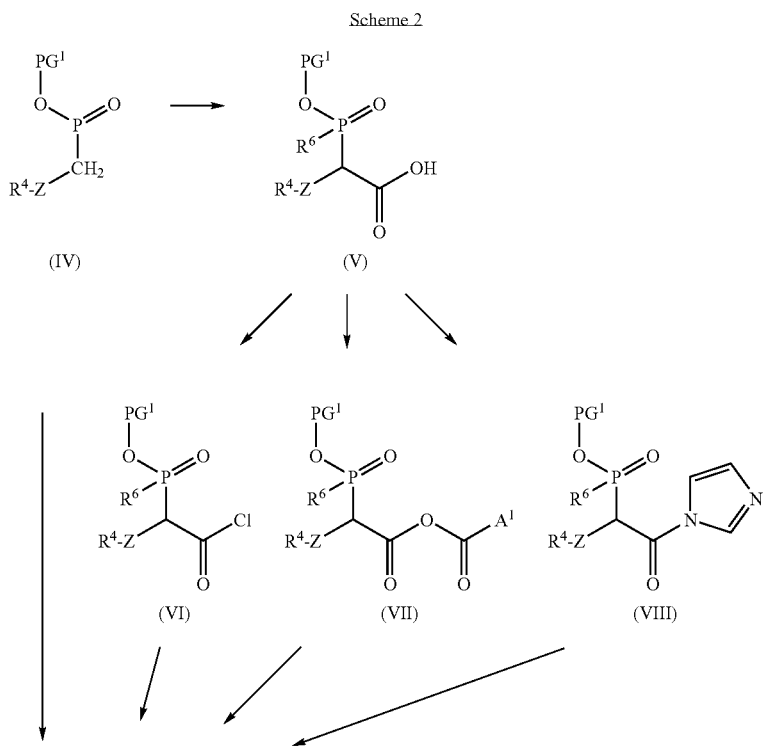

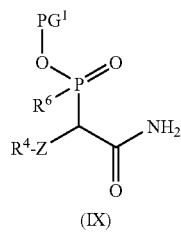

(IX)

Accordingly, a suitably substituted compound of formula (IV), a known compound or compound prepared by known methods, wherein $PG^1$ is a suitably selected oxygen protecting group such as $C_{1-4}$alkyl, and the like, preferably $PG^1$ is methyl, ethyl or t-butyl, more preferably, $PG^1$ is ethyl, is reacted with a suitably selected source of nitrogen such as LiHMDS, NaHMDS, and the like, preferably LiHMDS; wherein the source of nitrogen is preferably present in an amount in the range of from about 3.0 to about 6.0 molar equivalents, preferably about 3.0 molar equivalents;

in the presence of $CO_2$ gas; wherein the $CO_2$ gas is preferably bubbled into the reaction mixture in an excess amount; in an organic solvent such as THF, MTBE, DME, glyme, and the like; preferably THF; preferably at a temperature in the range of from about −10° C. to about 20° C., more preferably at a temperature in the range of from about 0° C. to about 20° C.; to yield the corresponding compound of formula (IX).

One skilled in the art will recognize that in the process as described above, the compound of formula (IX) is prepared in a mixture with the corresponding acid (a compound of formula (V)). Preferably, the compound of formula (IX) is isolated and/or further purified according to known methods, for example, the compound of formula (IX) may be further purified by acid/base workup.

Alternatively, a suitably substituted compound of formula (IV), a known compound or compound prepared by known methods is reacted with carbon dioxide; wherein the carbon dioxide is preferably bubbled into the reaction mixture in an excess amount, for example in an amount in the range of from about 10 to about 20 molar equivalents;

in the presence of a base such as n-butyl lithium, hexyllithium, and the like, preferably n-butyl lithium, wherein the base is preferably present in an amount in the range of from about 2.0 to bout 6.0 molar equivalents, more preferably about 3.0 molar equivalents; in an organic solvent or mixture thereof such as THF, THF/toluene, MTBE, and the like, preferably THF; preferably at a temperature in the range of from about −78° C. to about −40° C.; to yield the corresponding compound of formula (V).

The compound of formula (V) is reacted according to any of Methods A through C as outlined in more detail below, to yield the corresponding compound of formula (X). More particularly, as shown briefly below

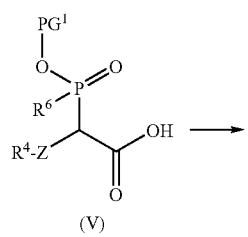

(V)

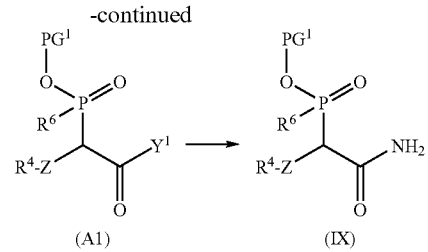

(A1)           (IX)

the compound of formula (V) is activated to yield the corresponding compound of formula (A1), wherein $Y^1$ is chloro (Method A), —O—C(O)—C1-4alkyl (Method B) of 1-imidazole (Method C); which compound of formula (A1) is then reacted with a source of ammonia, to yield the corresponding compound of formula (IX).

Method A: The compound of formula (V) is reacted with a suitably selected source of chlorine such as $SOCl_2$, oxalyl chloride, and the like, preferably $SOCl_2$; wherein the source of chlorine is preferably present in an amount in the range of from about 1.0 to about 1.5 molar equivalents; in an organic solvent such as DCE, DCM, acetonitrile, and the like, preferably DCM; preferably at a temperature in the range of from about 10° C. to about 40° C.; to yield the corresponding compound of formula (VI).

The compound of formula (VI) is reacted with a source of ammonia such as $NH_3$, $NH_4OH$, $NH_4OAc$, $NH_4Cl$, and the like, preferably $NH_3$; wherein the source of ammonia is preferably present in an amount in the range of form about 5 to about 10 molar equivalents; in an organic solvent such as toluene, DCM, THF, MTBE, and the like, preferably THF; preferably at a temperature in the range of from about 0° C. to about 50° C.; to yield the corresponding compound of formula (IX).

Method B: The compound of formula (V) is reacted with an alkyl chloroformate, such as n-butyl chloroformate, isobutyl chloroformate, ethylchloroformate, and the like, preferably isobutyl chloroformate; wherein the alkylchloroformate is preferably present in an amount in the range of from about 2.0 to about 5.0 molar equivalents; in an organic solvent such as MTBE, toluene, THF, DCM, and the like, preferably THF; preferably at a temperature in the range of from about −10° C. to about 50° C.; to yield the corresponding compound of formula (VII), wherein $A^2$ is the corresponding alkyl. For example, wherein the compound of formula (V) is reacted with isobutyl chloroformate, the product is the corresponding compound of formula (VII), wherein $A^1$ is isobutyl.

The compound of formula (VII) is reacted with a source of ammonia such as $NH_3$, $NH_4OH$, $NH_4OAc$, $NH_4Cl$, and the like, preferably $NH_4Cl$; wherein the source of ammonia is preferably present in an amount of from about 3.0 to about 10.0 molar equivalents; in an organic solvent such as acetone, acetonitrile, THF, and the like, preferably acetone; preferably at a temperature in the range of from about 0° C. to about 50° C.; to yield the corresponding compound of formula (IX).

Method C: The compound of formula (V) is reacted with CDI, a known compound; wherein the CDI is preferably present in an amount in the range of from about 1.0 to about 1.5 molar equivalent; in an organic solvent such as DMF, DMAc, NMP, and the like, preferably DMF; preferably at a temperature in the range of from about 0° C. to about 50° C.; to yield the corresponding compound of formula (VIII).

The compound of formula (VIII) is reacted with a source of ammonia such as $NH_3$, $NH_4OH$, $NH_4OAc$, $NH_4Cl$, and the like, preferably $NH_4Cl$; wherein the source of ammonia is preferably present in an amount in the range of from about 2.0 to about 6.0 molar equivalents; in an organic solvent such as DMF, acetonitrile, NMP, and the like; preferably at a temperature in the range of from about 0° C. to about 50° C.; to yield the corresponding compound of formula (IX).

The present invention is further directed to processes for the preparation of compounds of formula (XV) as outlined in Scheme 3, below.

LiHMDS, NaHMDS, and the like, preferably LiHMDS; wherein the source of nitrogen is preferably present in an amount in the range of from about 3.0 to about 6.0 molar equivalents, preferably about 3.0 molar equivalents;

in the presence of $CO_2$ gas; wherein the $CO_2$ gas is preferably bubbled into the reaction mixture in an excess amount; in an organic solvent such as THF, MTBE, DME, glyme, and the like; preferably THF; preferably at a temperature in the range of from about −10° C. to about 20° C., more preferably at a temperature in the range of from about 0° C. to about 20° C.; to yield the corresponding compound of formula (XV).

One skilled in the art will recognize that in the process as described above, the compound of formula (XV) is prepared in a mixture with the corresponding acid (a compound of formula (XI)). Preferably, the compound of formula (XV) is isolated and/or further purified according to known methods, for example, the compound of formula (XV) may be further purified by acid/base workup.

Alternatively, a suitably substituted compound of formula (X), a known compound or compound prepared by known

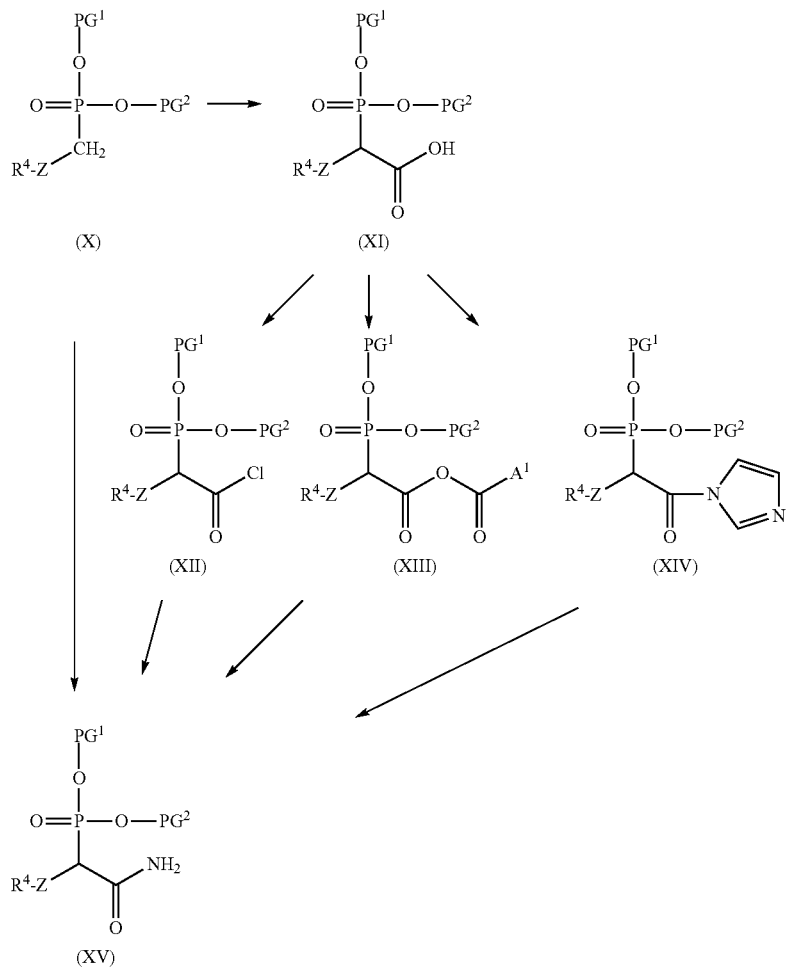

Scheme 3

Accordingly, a suitably substituted compound of formula (X), a known compound or compound prepared by known methods, wherein $PG^1$ is a suitably selected oxygen protecting group such as $C_{1-4}$alkyl, and the like, preferably $PG^1$ is methyl, ethyl or t-butyl, more preferably, $PG^1$ is ethyl, is reacted with a suitably selected source of nitrogen such as methods is reacted with carbon dioxide; wherein the carbon dioxide is preferably bubbled into the reaction mixture in an excess amount, for example in an amount in the range of from about 10 to about 20 molar equivalents;

in the presence of a base such as n-butyl lithium, hexyl-lithium, and the like, preferably n-butyl lithium, wherein the base is preferably present in an amount in the range of from about 2.0 to bout 6.0 molar equivalents, more preferably about 3.0 molar equivalents; in an organic solvent or mixture thereof such as THF, THF/toluene, MTBE, and the like, preferably THF; preferably at a temperature in the range of from about −78° C. to about −40° C.; to yield the corresponding compound of formula (XI).

The compound of formula (XI) is reacted according to any of Methods A through C as outlined in more detail below, to yield the corresponding compound of formula (XV). More particularly, as shown briefly below

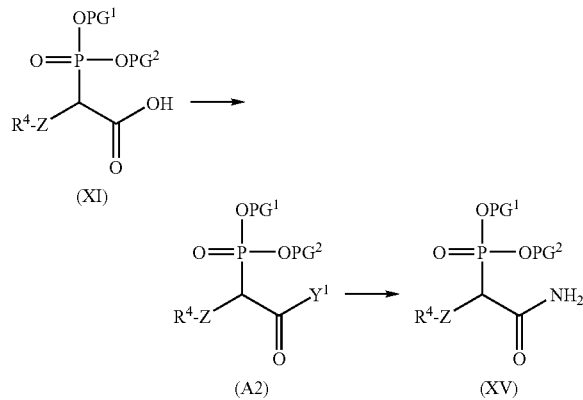

the compound of formula (XI) is activated to yield the corresponding compound of formula (A2), wherein $Y^1$ is chloro (Method A), —O—C(O)—$C_{1-4}$alkyl (Method B) of 1-imidazole (Method C); which compound of formula (A2) is then reacted with a source of ammonia, to yield the corresponding compound of formula (XV).

Method A: The compound of formula (XI) is reacted with a suitably selected source of chlorine such as $SOCl_2$, oxalyl chloride, and the like, preferably $SOCl_2$; wherein the source of chlorine is preferably present in an amount in the range of from about 1.0 to about 1.5 molar equivalents; in an organic solvent such as DCE, DCM, acetonitrile, and the like, preferably DCM; preferably at a temperature in the range of from about 10° C. to about 40° C.; to yield the corresponding compound of formula (XII).

The compound of formula (XII) is reacted with a source of ammonia such as $NH_3$, $NH_4OH$, $NH_4OAc$, $NH_4Cl$, and the like, preferably $NH_3$; wherein the source of ammonia is preferably present in an amount in the range of form about 5 to about 10 molar equivalents; in an organic solvent such as toluene, DCM, THF, MTBE, and the like, preferably THF; preferably at a temperature in the range of from about 0° C. to about 50° C.; to yield the corresponding compound of formula (XV).

Method B: The compound of formula (XI) is reacted with an alkyl chloroformate, such as n-butyl chloroformate, isobutyl chloroformate, ethylchloroformate, and the like, preferably isobutyl chloroformate; wherein the alkylchloroformate is preferably present in an amount in the range of from about 2.0 to about 5.0 molar equivalents; in an organic solvent such as MTBE, toluene, THF, DCM, and the like, preferably THF; preferably at a temperature in the range of from about −10° C. to about 50° C.; to yield the corresponding compound of formula (XIII), wherein $A^1$ is the corresponding alkyl. For example, wherein the compound of formula (XI) is reacted with isobutyl chloroformate, the product is the corresponding compound of formula (XIII), wherein $A^1$ is isobutyl.

The compound of formula (XIII) is reacted with a source of ammonia such as $NH_3$, $NH_4OH$, $NH_4OAc$, $NH_4Cl$, and the like, preferably $NH_4Cl$; wherein the source of ammonia is preferably present in an amount of from about 3.0 to about 10.0 molar equivalents; in an organic solvent such as acetone, acetonitrile, THF, and the like, preferably acetone; preferably at a temperature in the range of from about 0° C. to about 50° C.; to yield the corresponding compound of formula (XV).

Method C: The compound of formula (XI) is reacted with CDI, a known compound; wherein the CDI is preferably present in an amount in the range of from about 1.0 to about 1.5 molar equivalent; in an organic solvent such as DMF, DMAc, NMP, and the like, preferably DMF; preferably at a temperature in the range of from about 0° C. to about 50° C.; to yield the corresponding compound of formula (XIV).

The compound of formula (XIV) is reacted with a source of ammonia such as $NH_3$, $NH_4OH$, $NH_4OAc$, $NH_4Cl$, and the like, preferably $NH_4Cl$; wherein the source of ammonia is preferably present in an amount in the range of from about 2.0 to about 6.0 molar equivalents; in an organic solvent such as DMF, acetonitrile, NMP, and the like; preferably at a temperature in the range of from about 0° C. to about 50° C.; to yield the corresponding compound of formula (XV).

In an embodiment, the present invention is directed to processes for the preparation of a compound of formula (IX-S), as outlined in Scheme 4 below.

Scheme 4

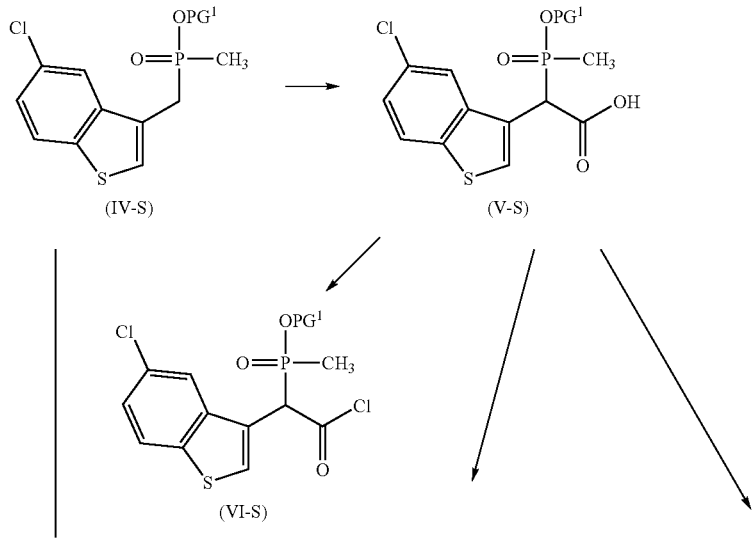

-continued

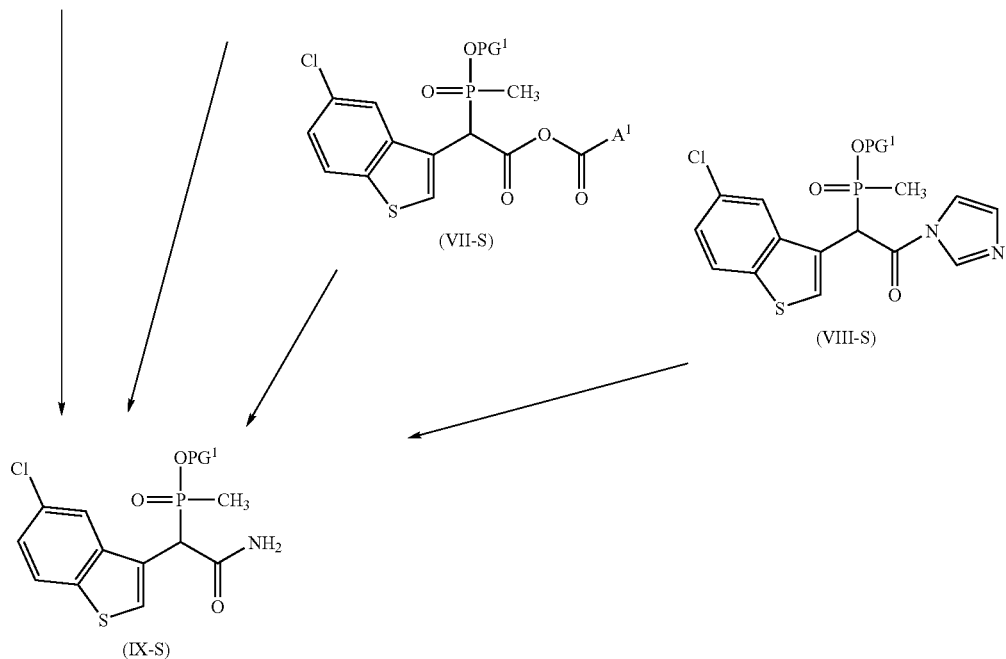

Accordingly, a suitably substituted compound of formula (IV-S), a known compound or compound prepared by known methods, wherein $PG^1$ is a suitably selected oxygen protecting group such as $C_{1-4}$alkyl, and the like, preferably $PG^1$ is methyl, ethyl or t-butyl, more preferably, $PG^1$ is ethyl, is reacted with a suitably selected source of nitrogen such as LiHMDS, NaHMDS, and the like, preferably LiHMDS; wherein the source of nitrogen is preferably present in an amount in the range of from about 3.0 to about 6.0 molar equivalents, preferably about 3.0 molar equivalents;

in the presence of $CO_2$ gas; wherein the $CO_2$ gas is preferably bubbled into the reaction mixture in an excess amount; in an organic solvent such as THF, MTBE, DME, glyme, and the like; preferably THF; preferably at a temperature in the range of from about −10° C. to about 20° C., more preferably at a temperature in the range of from about 0° C. to about 20° C.; to yield the corresponding compound of formula (IX-S).

One skilled in the art will recognize that in the process as described above, the compound of formula (IX-S) is prepared in a mixture with the corresponding acid (a compound of formula (V-S)). Preferably, the compound of formula (IX-S) is isolated and/or further purified according to known methods, for example, the compound of formula (IX-S) may be further purified by acid/base workup.

Alternatively, a suitably substituted compound of formula (IV-S), a known compound or compound prepared by known methods is reacted with carbon dioxide; wherein the carbon dioxide is preferably bubbled into the reaction mixture in an excess amount, for example in an amount in the range of from about 10 to about 20 molar equivalents;

in the presence of a base such as n-butyl lithium, hexyl-lithium, and the like, preferably n-butyl lithium, wherein the base is preferably present in an amount in the range of from about 2.0 to bout 6.0 molar equivalents, more preferably about 3.0 molar equivalents; in an organic solvent or mixture thereof such as THF, THF/toluene, MTBE, and the like, preferably THF; preferably at a temperature in the range of from about −78° C. to about −40° C.; to yield the corresponding compound of formula (V-S).

The compound of formula (V-S) is reacted according to any of Methods A through C as outlined in more detail below, to yield the corresponding compound of formula (IX-S). More particularly, as shown briefly below

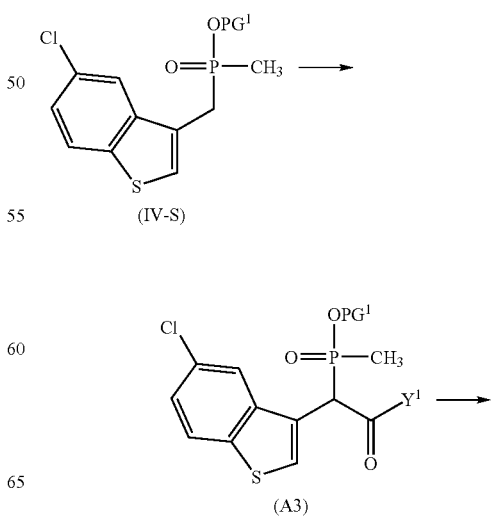

-continued

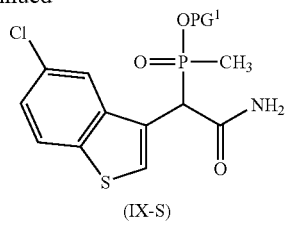

(IX-S)

the compound of formula (V-S) is activated to yield the corresponding compound of formula (A3), wherein $Y^1$ is chloro (Method A), —O—C(O)—$C_{1-4}$alkyl (Method B) of 1-imidazole (Method C); which compound of formula (A3) is then reacted with a source of ammonia, to yield the corresponding compound of formula (IX-S).

Method A: The compound of formula (V-S) is reacted with a suitably selected source of chlorine such as $SOCl_2$, oxalyl chloride, and the like, preferably $SOCl_2$; wherein the source of chlorine is preferably present in an amount in the range of from about 1.0 to about 1.5 molar equivalents; in an organic solvent such as DCE, DCM, acetonitrile, and the like, preferably DCM; preferably at a temperature in the range of from about 10° C. to about 40° C.; to yield the corresponding compound of formula (VI-S).

The compound of formula (VI-S) is reacted with a source of ammonia such as $NH_3$, $NH_4OH$, $NH_4OAc$, $NH_4Cl$, and the like, preferably $NH_3$; wherein the source of ammonia is preferably present in an amount in the range of form about 5 to about 10 molar equivalents; in an organic solvent such as toluene, DCM, THF, MTBE, and the like, preferably THF; preferably at a temperature in the range of from about 0° C. to about 50° C.; to yield the corresponding compound of formula (IX-S).

Method B: The compound of formula (V-S) is reacted with an alkyl chloroformate, such as n-butyl chloroformate, isobutyl chloroformate, ethylchloroformate, and the like, preferably isobutyl chloroformate; wherein the alkylchloroformate is preferably present in an amount in the range of from about 2.0 to about 5.0 molar equivalents; in an organic solvent such as MTBE, toluene, THF, DCM, and the like, preferably THF; preferably at a temperature in the range of from about −10° C. to about 50° C.; to yield the corresponding compound of formula (VII-S), wherein $A^1$ is the corresponding alkyl. For example, wherein the compound of formula (V-S) is reacted with isobutyl chloroformate, the product is the corresponding compound of formula (VII-S), wherein $A^1$ is isobutyl.

The compound of formula (VII-S) is reacted with a source of ammonia such as $NH_3$, $NH_4OH$, $NH_4OAc$, $NH_4Cl$, and the like, preferably $NH_4Cl$; wherein the source of ammonia is preferably present in an amount of from about 3.0 to about 10.0 molar equivalents; in an organic solvent such as acetone, acetonitrile, THF, and the like, preferably acetone; preferably at a temperature in the range of from about 0° C. to about 50° C.; to yield the corresponding compound of formula (IX-S).

Method C: The compound of formula (V-S) is reacted with CDI, a known compound; wherein the CDI is preferably present in an amount in the range of from about 1.0 to about 1.5 molar equivalent; in an organic solvent such as DMF, DMAc, NMP, and the like, preferably DMF; preferably at a temperature in the range of from about 0° C. to about 50° C.; to yield the corresponding compound of formula (VIII-S).

The compound of formula (VIII-S) is reacted with a source of ammonia such as $NH_3$, $NH_4OH$, $NH_4OAc$, $NH_4Cl$, and the like, preferably $NH_4Cl$; wherein the source of ammonia is preferably present in an amount in the range of from about 2.0 to about 6.0 molar equivalents; in an organic solvent such as DMF, acetonitrile, NMP, and the like; preferably at a temperature in the range of from about 0° C. to about 50° C.; to yield the corresponding compound of formula (IX-S).

In another embodiment, the present invention is directed to processes for the preparation of a compound of formula (XV-S), as outlined in Scheme 5 below.

Scheme 5

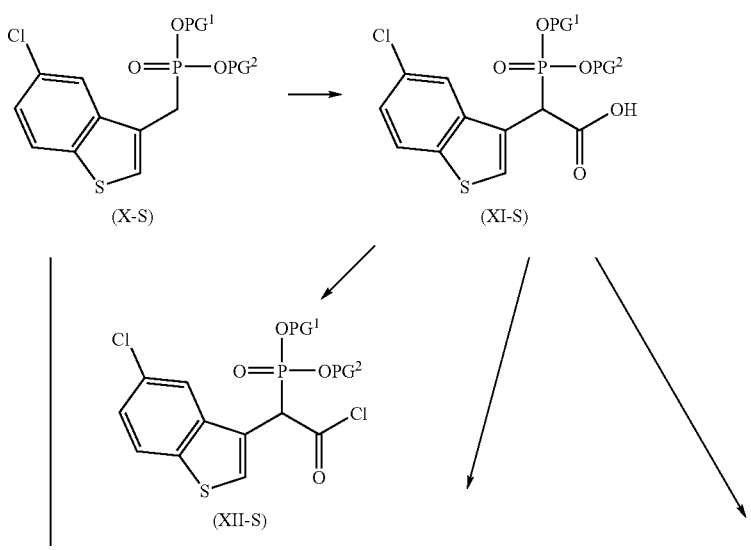

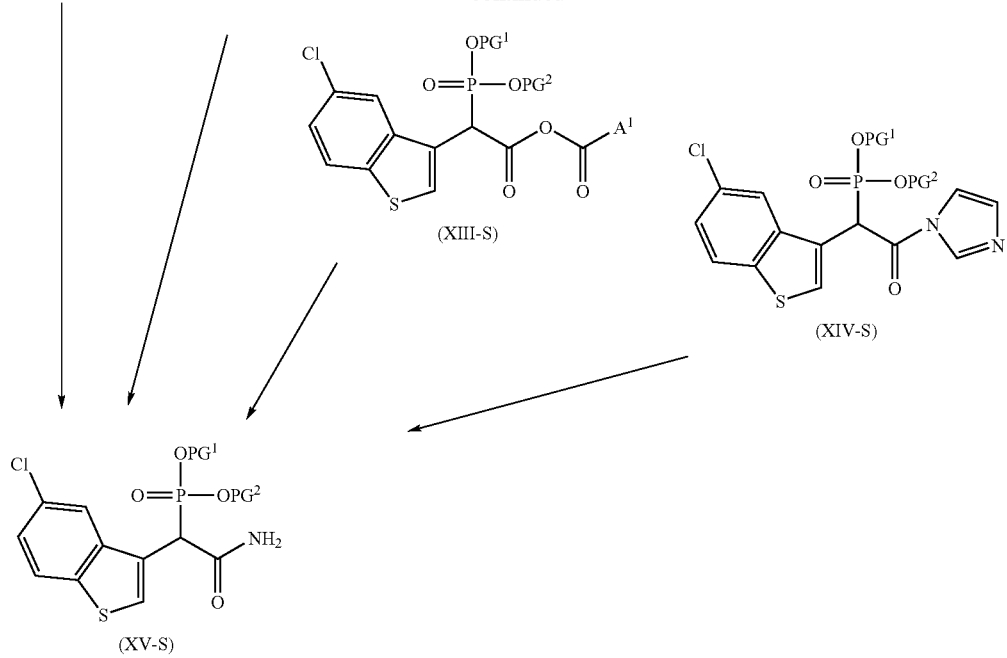

Accordingly, a suitably substituted compound of formula (X-S), a known compound or compound prepared by known methods, wherein $PG^1$ is a suitably selected oxygen protecting group such as $C_{1-4}$alkyl, and the like, preferably $PG^1$ is methyl, ethyl or t-butyl, more preferably, $PG^1$ is ethyl, and wherein $PG^2$ is a suitably selected oxygen protecting group such as $C_{1-4}$alkyl, and the like, preferably $PG^2$ is methyl, ethyl or t-butyl, more preferably, $PG^2$ is ethyl, wherein $PG^1$ and $PG^2$ are preferably the same; is reacted with a suitably selected source of nitrogen such as LiHMDS, NaHMDS, and the like, preferably LiHMDS; wherein the source of nitrogen is preferably present in an amount in the range of from about 3.0 to about 6.0 molar equivalents, preferably about 3.0 molar equivalents;

in the presence of $CO_2$ gas; wherein the $CO_2$ gas is preferably bubbled into the reaction mixture in an excess amount; in an organic solvent such as THF, MTBE, DME, glyme, and the like; preferably THF; preferably at a temperature in the range of from about −10° C. to about 20° C., more preferably at a temperature in the range of from about 0° C. to about 20° C.; to yield the corresponding compound of formula (XV-S).

One skilled in the art will recognize that in the process as described above, the compound of formula (XV-S) is prepared in a mixture with the corresponding acid (a compound of formula (XI-S)). Preferably, the compound of formula (XV-S) is isolated and/or further purified according to known methods, for example, the compound of formula (XV-S) may be further purified by acid/base workup.

Alternatively, a suitably substituted compound of formula (X-S), a known compound or compound prepared by known methods is reacted with carbon dioxide; wherein the carbon dioxide is preferably bubbled into the reaction mixture in an excess amount, for example in an amount in the range of from about 10 to about 20 molar equivalents;

in the presence of a base such as n-butyl lithium, hexyllithium, and the like, preferably n-butyl lithium, wherein the base is preferably present in an amount in the range of from about 2.0 to bout 6.0 molar equivalents, more preferably about 3.0 molar equivalents; in an organic solvent or mixture thereof such as THF, THF/toluene, MTBE, and the like, preferably THF; preferably at a temperature in the range of from about −78° C. to about −40° C.; to yield the corresponding compound of formula (XI-S).

The compound of formula (XI-S) is reacted according to any of Methods A through C as outlined in more detail below, to yield the corresponding compound of formula (XV-S). More particularly, as shown briefly below

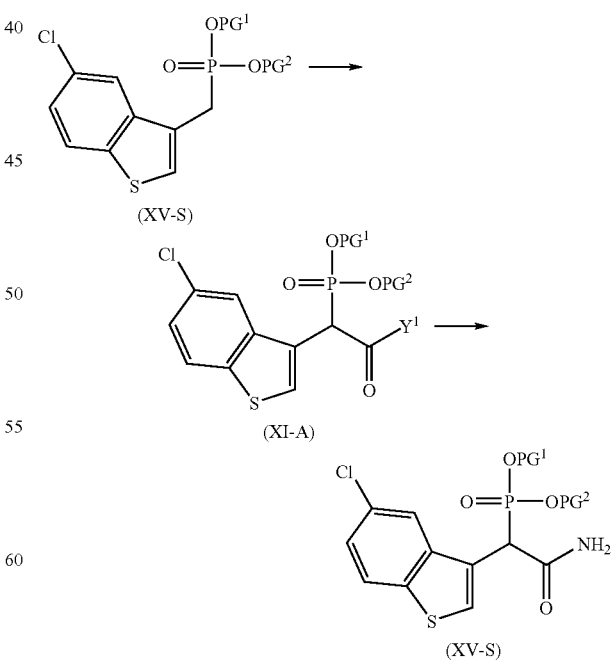

the compound of formula (XI-S) is activated to yield the corresponding compound of formula (A4), wherein $Y^1$ is chloro (Method A), —O—C(O)—C$_{1-4}$alkyl (Method B) of 1-imidazole (Method C); which compound of formula (A4) is then reacted with a source of ammonia, to yield the corresponding compound of formula (XV-S).

Method A: The compound of formula (XI-S) is reacted with a suitably selected source of chlorine such as SOCl$_2$, oxalyl chloride, and the like, preferably SOCl$_2$; wherein the source of chlorine is preferably present in an amount in the range of from about 1.0 to about 1.5 molar equivalents; in an organic solvent such as DCE, DCM, acetonitrile, and the like, preferably DCM; preferably at a temperature in the range of from about 10° C. to about 40° C.; to yield the corresponding compound of formula (XII-S).

The compound of formula (XII-S) is reacted with a source of ammonia such as NH$_3$, NH$_4$OH, NH$_4$OAc, NH$_4$Cl, and the like, preferably NH$_3$; wherein the source of ammonia is preferably present in an amount in the range of form about 5 to about 10 molar equivalents; in an organic solvent such as toluene, DCM, THF, MTBE, and the like, preferably THF; preferably at a temperature in the range of from about 0° C. to about 50° C.; to yield the corresponding compound of formula (XV-S).

Method B: The compound of formula (XI-S) is reacted with an alkyl chloroformate, such as n-butyl chloroformate, isobutyl chloroformate, ethylchloroformate, and the like, preferably isobutyl chloroformate; wherein the alkylchloroformate is preferably present in an amount in the range of from about 2.0 to about 5.0 molar equivalents; in an organic solvent such as MTBE, toluene, THF, DCM, and the like, preferably THF; preferably at a temperature in the range of from about –10° C. to about 50° C.; to yield the corresponding compound of formula (XIII-S), wherein A$^1$ is the corresponding alkyl. For example, wherein the compound of formula (XI-S) is reacted with isobutyl chloroformate, the product is the corresponding compound of formula (XIII-S), wherein A$^1$ is isobutyl.

The compound of formula (XIII-S) is reacted with a source of ammonia such as NH$_3$, NH$_4$OH, NH$_4$OAc, NH$_4$Cl, and the like, preferably NH$_4$Cl; wherein the source of ammonia is preferably present in an amount of from about 3.0 to about 10.0 molar equivalents; in an organic solvent such as acetone, acetonitrile, THF, and the like, preferably acetone; preferably at a temperature in the range of from about 0° C. to about 50° C.; to yield the corresponding compound of formula (XV-S).

Method C: The compound of formula (XI-S) is reacted with CDI, a known compound; wherein the CDI is preferably present in an amount in the range of from about 1.0 to about 1.5 molar equivalent; in an organic solvent such as DMF, DMAc, NMP, and the like, preferably DMF; preferably at a temperature in the range of from about 0° C. to about 50° C.; to yield the corresponding compound of formula (XIV-S).

The compound of formula (XIV-S) is reacted with a source of ammonia such as NH$_3$, NH$_4$OH, NH$_4$OAc, NH$_4$Cl, and the like, preferably NH$_4$Cl; wherein the source of ammonia is preferably present in an amount in the range of from about 2.0 to about 6.0 molar equivalents; in an organic solvent such as DMF, acetonitrile, NMP, and the like; preferably at a temperature in the range of from about 0° C. to about 50° C.; to yield the corresponding compound of formula (XV-S).

The present invention is directed to a process for the preparation of compounds of formula (I), preferably compounds of formula (I) wherein R$^6$ is other than hydroxy, as described in more detail in Scheme 6 below.

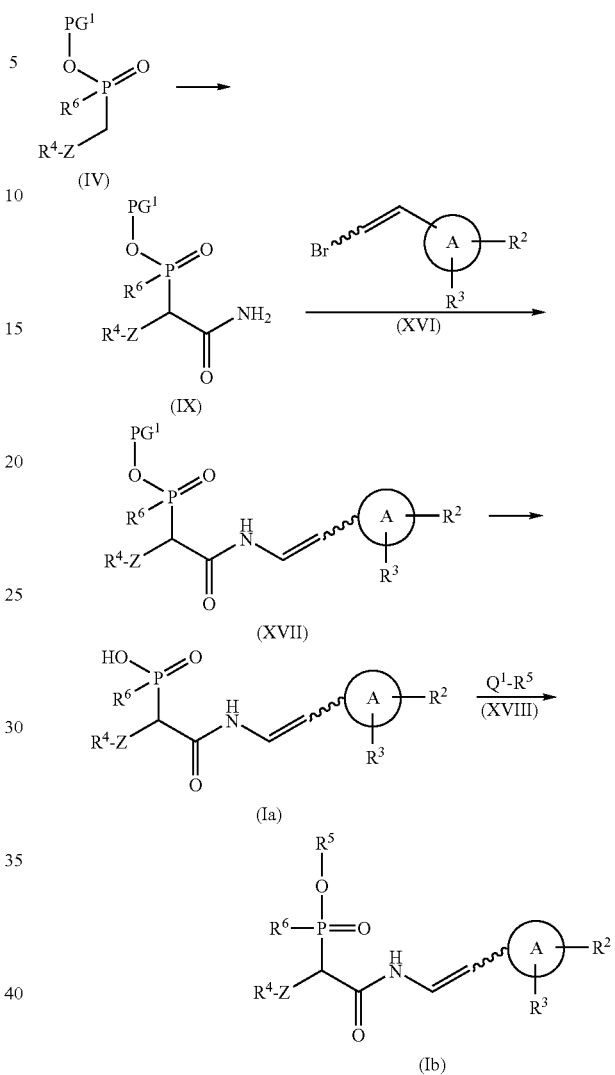

Scheme 6

Accordingly, a suitably substituted compound of formula (IV), wherein PG$^1$ is a suitably substituted oxygen protecting group such as C$_{1-4}$alkyl, phenyl, benzyl, and the like, preferably, PG$^1$ is methyl, ethyl or t-butyl, more preferably, PG$^1$ is ethyl; is reacted according to any of the methods as described in Scheme 2 above; to yield the corresponding compound of formula (IX).

The compound of formula (IX) is reacted with a suitably substituted compound of formula (XVI); wherein the compound of formula (XVI) is preferably present in an excess of the corresponding trans orientation, more preferably, the compound of formula (XVI) is present in the corresponding trans orientation; wherein the compound of formula (XVI) is preferably present in an amount in the range of from about 1.0 to about 2.0 molar equivalents (relative to the moles of the compound of formula (IX)), more preferably in an amount in the range of from about 1.0 to about 1.5 molar equivalents, more preferably still in an amount of about 1.1 to about 1.2 molar equivalents; in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as $Cs_2CO_3$, $K_2CO_3$, $K_3PO_4$, and the like, preferably $Cs_2CO_3$; wherein the inorganic base is preferably present in an amount in the range of from about 0.5 to about 2.0 molar equivalents, more preferably, in an amount in the range of from about 0.5 to about 3.0 molar equivalents, more preferably, in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;

in an organic solvent or mixtures thereof, such as DMA, N-methyl-pyrrolidinone, DMA/acetonitrile mixture, DMF, THF, and the like, preferably DMA; preferably, at a temperature in the range of from about 50° C. to about 100° C., preferably at about 75° C.; to yield the corresponding compound of formula (XVII).

Preferably, the compound of formula (IX) is reacted with the compound of formula (XVI) under an inert atmosphere, for example under nitrogen or argon. Preferably, a mixture of the compound of formula (IX), the CuI, the ligand, the inorganic base and the organic solvent is heated to a temperature in the range of from about 50° C. to about 100, to yield a homogeneous mixture; prior to addition of the compound of formula (XVI).

Preferably, in the reaction of the compound of formula (IX) with the compound of formula (XVI), the compound of formula (XVI) is present in an excess of its geometrical isomer, more particularly, its corresponding trans isomer, to yield the compound of formula (XVII) in its corresponding trans isomer.

When the compound of formula (IX) is reacted with a compound of formula (XVI), wherein the compound of formula (XVI) is present in either its corresponding cis configuration or as a mixture of its corresponding cis and trans configurations, then the reaction proceeds to yield the compound of formula (XVII) as a mixture of its corresponding cis and trans configurations.

The compound of formula (XVII) is de-protected according to known methods, to yield the corresponding compound of formula (Ia). For example, the compound of formula (XVII) may be reacted with a suitably selected de-alkylating agent such as TMS-Br, TMS-I, $Br_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine;

in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (Ia), a compound of formula (I) wherein $R^5$ is hydrogen.

Alternatively, the compound of formula (XVII) may be reacted with a suitably selected de-alkylating agent such as TMS-Cl, and the like; in the presence of NaI, and the like; in an organic solvent such as acetonitrile, and the like; to yield the corresponding compound of formula (Ia), a compound of formula (I) wherein $R^5$ is hydrogen.

The compound of formula (Ia) may be optionally further reacted with a suitably substituted compound of formula (XVIII), wherein $Q^1$ is a suitably selected leaving group such as Br, Cl, I, and the like, preferably Cl, a known compound or compound prepared by known methods; wherein the compound of formula (XVIII) is preferably present in an amount in the range of from about 1.0 to about 3.0 molar equivalents, more preferably about 1.7 molar equivalents; in the presence of an organic base such as DIPEA, TEA, pyridine, and the like, preferably DIPEA; wherein the organic base is preferably present in an amount in the range of from about 1.5 to about 5.0 molar equivalents; more preferably about 2.0 molar equivalents; in an organic solvent such DMF and the like; preferably at a temperature in the range of from about 50° C. to about 120° C., more preferably at about 73° C.; to yield the corresponding compound of formula (Ib), a compound of formula (I) wherein $R^5$ is other than hydrogen.

Compounds of formula (I) wherein $R^6$ is hydroxy may be prepared according to the process outlined in Scheme 7 below.

Scheme 7

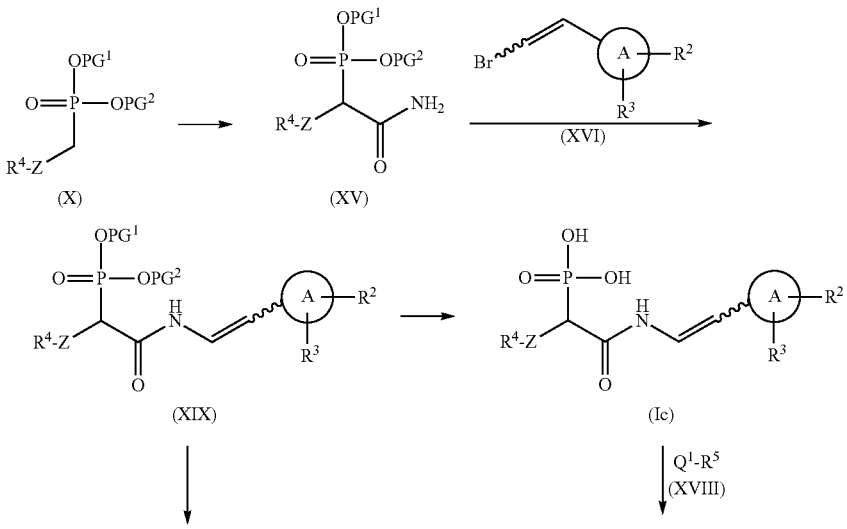

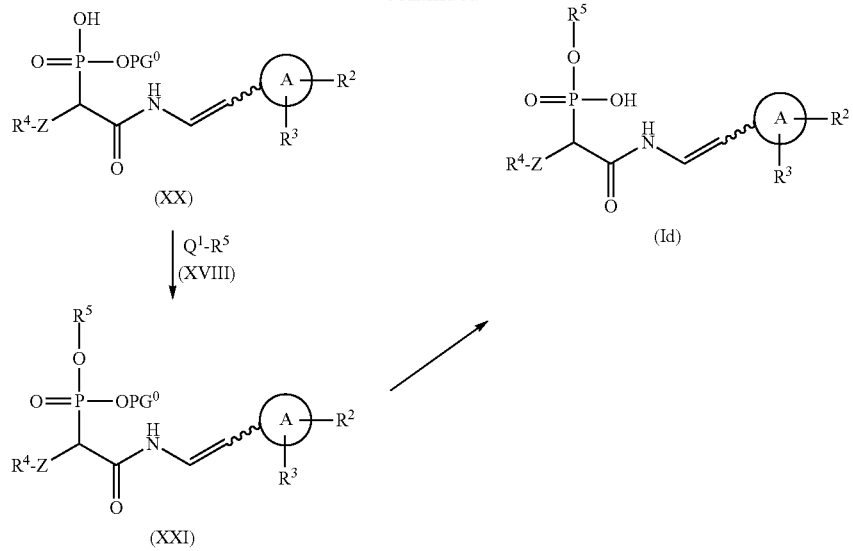

Accordingly, a suitably substituted compound of formula (X), wherein $PG^1$ is a suitably substituted oxygen protecting group such as $C_{1-4}$alkyl, phenyl, benzyl, and the like, and wherein $PG^2$ is a suitably selected oxygen protecting group such as $C_{1-4}$alkyl, phenyl, benzyl, and the like, and wherein $PG^1$ and $PG^2$ are the same or different oxygen protecting groups, preferably $PG^1$ and $PG^2$ are different oxygen protecting groups; is reacted according to any of the methods as described in Scheme 3 above; to yield the corresponding compound of formula (XV).

The compound of formula (XV) is reacted with a suitably substituted compound of formula (XVI); wherein the compound of formula (XVI) is preferably present in an excess of the corresponding trans orientation, more preferably, the compound of formula (XVI) is present in the corresponding trans orientation; wherein the compound of formula (XVI) is preferably present in an amount in the range of from about 1.0 to about 2.0 molar equivalents (relative to the moles of the compound of formula (XV)), more preferably in an amount in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as $Cs_2CO_3$, $K_2CO_3$, $K_3PO_4$, and the like, preferably $Cs_2CO_3$; wherein the inorganic base is preferably present in an amount in the range of from about 0.5 to about 2.0 molar equivalents, more preferably, in an amount in the range of from about 0.5 to about 3.0 molar equivalents, more preferably in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;

in an organic solvent or mixtures thereof, such as DMA, N-methyl-pyrrolidinone, DMA/acetonitrile mixture, DMF, THF, and the like, preferably DMA; at a temperature in the range of from about 50° C. to about 100° C., preferably at about 75° C.; to yield the corresponding compound of formula (XIX).

Preferably, the compound of formula (XV) is reacted with the compound of formula (XVI) under an inert atmosphere, for example under nitrogen or argon. Preferably, a mixture of the compound of formula (XV), the CuI, the ligand, the inorganic base and the organic solvent is heated to a temperature in the range of from about 50° C. to about 100, to yield a homogeneous mixture; prior to addition of the compound of formula (XVI).

Preferably, in the reaction of the compound of formula (XV) with the compound of formula (XVI), the compound of formula (XVI) is present in an excess of its geometrical isomer, more particularly, its corresponding trans isomer, to yield the compound of formula (XIX) in its corresponding trans isomer. When the compound of formula (XV) is reacted with a compound of formula (XVI), wherein the compound of formula (XVI) is present in either its corresponding cis configuration or as a mixture of its corresponding cis and trans configurations, then the reaction proceeds to yield the compound of formula (XIX) as a mixture of its corresponding cis and trans configurations.

The compound of formula (XIX) is de-protected at both the $PG^1$ and $PG^2$ according to known methods, to yield the corresponding compound of formula (Ic). For example, the compound of formula (XIX) is reacted with a suitably selected de-alkylating agent such as TMS-Br, TMS-I, $Br_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine; in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (Ic).

Alternatively, the compound of formula (XIX) may be reacted with a suitably selected de-alkylating agent such as TMS-Cl, and the like; in the presence of NaI, and the like; in an organic solvent such as acetonitrile, and the like; to yield the corresponding compound of formula (Ic).

The compound of formula (Ic) may be optionally further reacted with a suitably substituted compound of formula (XVIII), wherein $Q^1$ is a suitably selected leaving group such as Br, Cl, I, and the like, preferably Cl, a known compound or compound prepared by known methods; wherein the compound of formula (XVIII) is preferably present in an amount in the range of from about 1.0 to about 3.0 molar equivalents, more preferably about 1.7 molar equivalents; in the presence of an organic base such as DIPEA, TEA, pyridine, and the like, preferably DIPEA; wherein the organic base is preferably present in an amount in the range of from about 1.5 to about 5.0 molar equivalents; more preferably about 2.0 molar equivalents; in an organic solvent such DMF and the like; preferably at a temperature in the range of from about 50° C. to about 120° C., more preferably at about 73° C.; to yield the corresponding compound of formula (Id).

Alternatively, the compound of formula (XIX) is de-protected at either $PG^1$ or $PG^2$, according to known methods, to yield the corresponding compound of formula (XX), wherein $PG^0$ is the un-protected PG group. For example, wherein the compound of formula (XIX) is de-protected to remove $PG^1$, then in the resulting compound of formula (XX), $PG^0$ is $PG^2$. Alternatively, wherein the compound of formula (XIX) is de-protected to remove $PG^2$, then in the resulting compound of formula (XX), $PG^0$ is $PG^1$.

The compound of formula (XX) is reacted with a suitably substituted compound of formula (XVIII), wherein $Q^1$ is a suitably selected leaving group such as Br, Cl, I, and the like, preferably Cl, a known compound or compound prepared by known methods; wherein the compound of formula (XVIII) is preferably present in an amount in the range of from about 1.0 to about 3.0 molar equivalents, more preferably about 1.7 molar equivalents; in the presence of an organic base such as DIPEA, TEA, pyridine, and the like, preferably DIPEA; wherein the organic base is preferably present in an amount in the range of from about 1.5 to about 5.0 molar equivalents; more preferably about 2.0 molar equivalents; in an organic solvent such DMF and the like; preferably at a temperature in the range of from about 50° C. to about 120° C., more preferably at about 73° C.; to yield the corresponding compound of formula (XXI).

The compound of formula (XXI) is then de-protected according to known methods, as described herein, to yield the corresponding compound of formula (Id).

In an embodiment, the present invention is directed to a process for the preparation of compounds of formula (X-S), as outlined in Scheme 8 below.

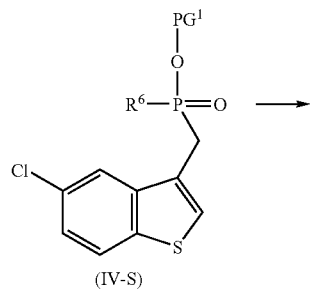

Accordingly, a suitably substituted compound of formula (IV-S), wherein $PG^1$ is a suitably substituted oxygen protecting group such as $C_{1-4}$alkyl, phenyl, benzyl, and the like, preferably, $PG^1$ is methyl, ethyl or t-butyl, more preferably, $PG^1$ is ethyl; is reacted according to any of the methods as described in Schemes 2 and 4 above; to yield the corresponding compound of formula (IX-S).

The compound of formula (IX-S) is reacted with a suitably substituted compound of formula (XVI-S); wherein the compound of formula (XVI-S) is preferably present in an excess of the corresponding trans orientation, more preferably, the compound of formula (XVI-S) is present in the corresponding trans orientation; wherein the compound of formula (XVI-S) is preferably present in an amount in the range of from about 1.0 to about 2.0 molar equivalents (relative to the moles of the compound of formula (IX-S)), more preferably in an amount in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as $Cs_2CO_3$, $K_2CO_3$, $K_3PO_4$, and the like, preferably $Cs_2CO_3$; wherein the inorganic base is preferably present in an amount in the range of from about 0.5 to about 2.0 molar equivalents, more preferably, in an amount in the range of from about 0.5 to about 3.0 molar equivalents, more preferably, in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;

in an organic solvent or mixtures thereof, such as DMA, N-methyl-pyrrolidinone, DMA/acetonitrile mixture, DMF, THF, and the like, preferably DMA; preferably, at a temperature in the range of from about 50° C. to about 100° C., preferably at about 75° C.; to yield the corresponding compound of formula (XVII-S).

Preferably, the compound of formula (IX-S) is reacted with the compound of formula (XVI-S) under an inert atmosphere, for example under nitrogen or argon. Preferably, a mixture of the compound of formula (IX-S), the CuI, the ligand, the inorganic base and the organic solvent is heated to a temperature in the range of from about 50° C. to about 100, to yield a homogeneous mixture; prior to addition of the compound of formula (XVI-S).

Preferably, in the reaction of the compound of formula (IX-S) with the compound of formula (XVI-S), the compound of formula (XVI-S) is present in an excess of its geometrical isomer, more particularly, its corresponding trans isomer, to yield the compound of formula (XVII-S) in its corresponding trans isomer. When the compound of formula (IX-S) is reacted with a compound of formula (XVI-S), wherein the compound of formula (XVI-S) is present in either its corresponding cis configuration or as a mixture of its corresponding cis and trans configurations, then the reaction proceeds to yield the compound of formula (XVII-S) as a mixture of its corresponding cis and trans configurations.

The compound of formula (XVII-S) is de-protected according to known methods, to yield the corresponding compound of formula (Ie). For example, the compound of formula (XVII-S) may be reacted with a suitably selected de-alkylating agent such as TMS-Br, TMS-I, $Br_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine;

in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (I-Sa), a compound of formula (X-S) wherein $R^5$ is hydrogen.

Alternatively, the compound of formula (XVII-S) may be reacted with a suitably selected de-alkylating agent such as TMS-Cl, and the like; in the presence of NaI, and the like; in an organic solvent such as acetonitrile, and the like; to yield the corresponding compound of formula (I-Sa), a compound of formula (X-S) wherein $R^5$ is hydrogen.

The compound of formula (I-Sa) may be optionally further reacted with a suitably substituted compound of formula (XVIII), wherein $Q^1$ is a suitably selected leaving group such as Br, Cl, I, and the like, preferably Cl, a known compound or compound prepared by known methods; wherein the compound of formula (XVIII) is preferably present in an amount in the range of from about 1.0 to about 3.0 molar equivalents, more preferably about 1.7 molar equivalents; in the presence of an organic base such as DIPEA, TEA, pyridine, and the like, preferably DIPEA; wherein the organic base is preferably present in an amount in the range of from about 1.5 to about 5.0 molar equivalents; more preferably about 2.0 molar equivalents; in an organic solvent such DMF and the like; preferably at a temperature in the range of from about 50° C. to about 120° C., more preferably at about 73° C.; to yield the corresponding compound of formula (I-Sb), a compound of formula (X-S) wherein $R^5$ is other than hydrogen.

In additional embodiments, the present invention is further directed to processes for the preparation of compounds of formula (X-S) wherein $R^6$ is hydroxy as outlined in Scheme 9 below.

Scheme 9

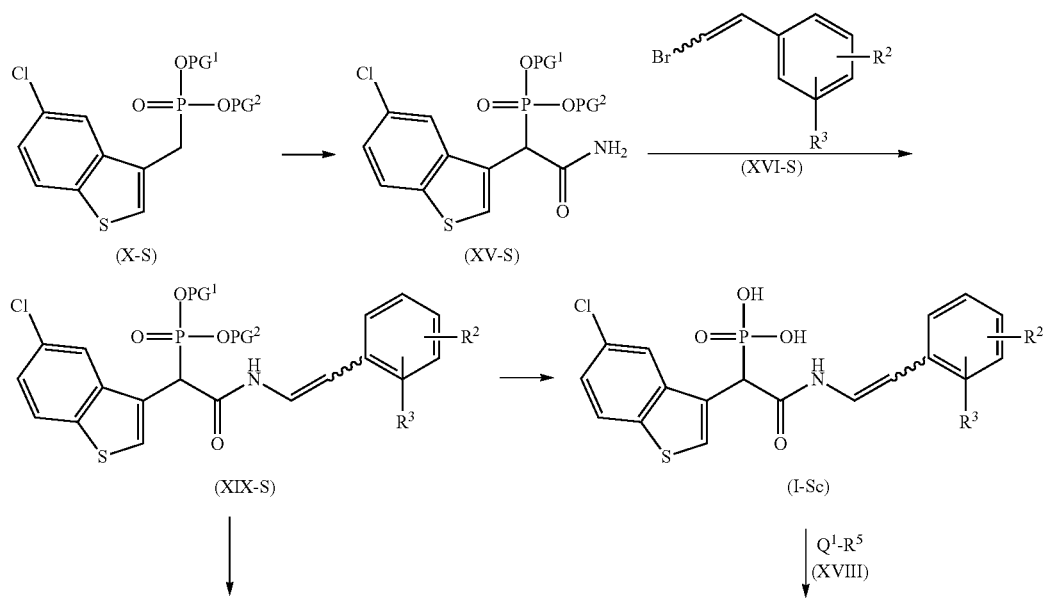

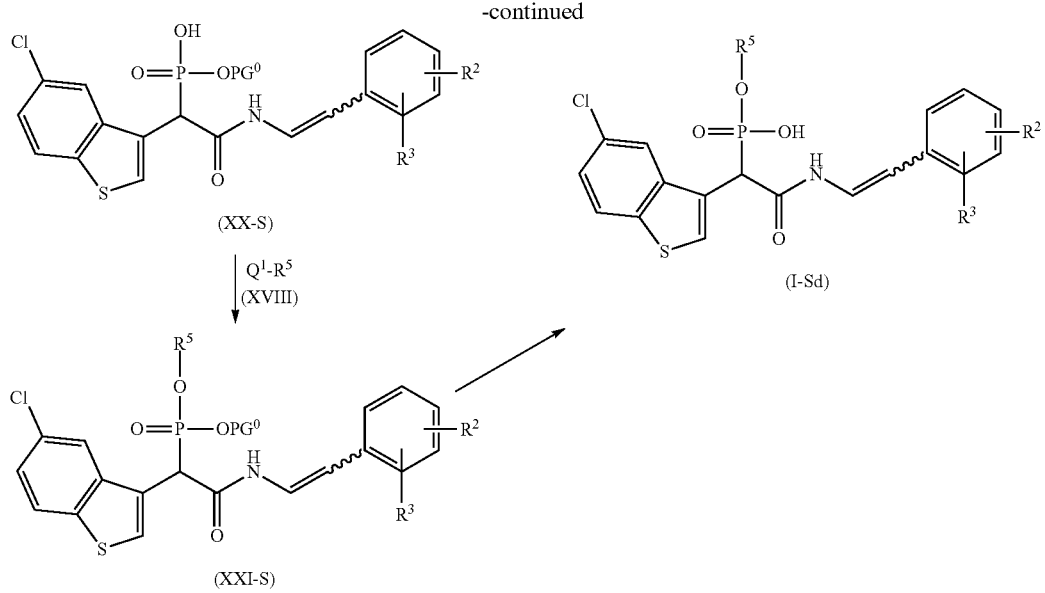

Accordingly, a suitably substituted compound of formula (X-S), wherein $PG^1$ is a suitably substituted oxygen protecting group such as $C_{1-4}$alkyl, phenyl, benzyl, and the like, and wherein $PG^2$ is a suitably selected oxygen protecting group such as $C_{1-4}$alkyl, phenyl, benzyl, and the like, and wherein $PG^1$ and $PG^2$ are the same or different oxygen protecting groups, preferably $PG^1$ and $PG^2$ are different oxygen protecting groups; is reacted according to any of the methods as described in Scheme 3 and 5 above; to yield the corresponding compound of formula (XV-S).

The compound of formula (XV-S) is reacted with a suitably substituted compound of formula (XVI-S); wherein the compound of formula (XVI-S) is preferably present in an excess of the corresponding trans orientation, more preferably, the compound of formula (XVI-S) is present in the corresponding trans orientation; wherein the compound of formula (XVI-S) is preferably present in an amount in the range of from about 1.0 to about 2.0 molar equivalents (relative to the moles of the compound of formula (XV-S)), more preferably in an amount in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as $Cs_2CO_3$, $K_2CO_3$, $K_3PO_4$, and the like, preferably $Cs_2CO_3$; wherein the inorganic base is preferably present in an amount in the range of from about 0.5 to about 2.0 molar equivalents, more preferably, in an amount in the range of from about 0.5 to about 3.0 molar equivalents, more preferably, in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;

in an organic solvent or mixtures thereof, such as DMA, N-methyl-pyrrolidinone, DMA/acetonitrile mixture, DMF, THF, and the like, preferably DMA; at a temperature in the range of from about 50° C. to about 100° C., preferably at about 75° C.; to yield the corresponding compound of formula (XIX-S).

Preferably, the compound of formula (XV-S) is reacted with the compound of formula (XVI-S) under an inert atmosphere, for example under nitrogen or argon. Preferably, a mixture of the compound of formula (XV-S), the CuI, the ligand, the inorganic base and the organic solvent is heated to a temperature in the range of from about 50° C. to about 100, to yield a homogeneous mixture; prior to addition of the compound of formula (XVI-S).

Preferably, in the reaction of the compound of formula (XV-S) with the compound of formula (XVI-S), the compound of formula (XVI-S) is present in an excess of its geometrical isomer, more particularly, its corresponding trans isomer, to yield the compound of formula (XIX-S) in its corresponding trans isomer. When the compound of formula (XV-S) is reacted with a compound of formula (XVI-S), wherein the compound of formula (XVI-S) is present in either its corresponding cis configuration or as a mixture of its corresponding cis and trans configurations, then the reaction proceeds to yield the compound of formula (XIX) as a mixture of its corresponding cis and trans configurations.

The compound of formula (XIX-S) is de-protected at both the $PG^1$ and $PG^2$ according to known methods, to yield the corresponding compound of formula (I-Sc). For example, the compound of formula (XIX-S) is reacted with a suitably selected de-alkylating agent such as TMS-Br, TMS-I, $Br_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine; in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (I-Sc).

Alternatively, the compound of formula (XIX-S) may be reacted with a suitably selected de-alkylating agent such as TMS-Cl, and the like; in the presence of NaI, and the like; in an organic solvent such as acetonitrile, and the like; to yield the corresponding compound of formula (I-Sc).

The compound of formula (I-Sc) may be optionally further reacted with a suitably substituted compound of formula (XVIII), wherein $Q^1$ is a suitably selected leaving group such as Br, Cl, I, and the like, preferably Cl, a known compound or compound prepared by known methods; wherein the compound of formula (XVIII) is preferably present in an amount in the range of from about 1.0 to about 3.0 molar equivalents, more preferably about 1.7 molar equivalents; in the presence of an organic base such as DIPEA, TEA, pyridine, and the like, preferably DIPEA; wherein the organic base is preferably present in an amount in the range of from about 1.5 to about 5.0 molar equivalents; more preferably about 2.0 molar equivalents; in an organic solvent such DMF and the like; preferably at a temperature in the range of from about 50° C. to about 120° C., more preferably at about 73° C.; to yield the corresponding compound of formula (I-Sd).

Alternatively, the compound of formula (XIX-S) is de-protected at either $PG^1$ or $PG^2$, according to known methods, to yield the corresponding compound of formula (X-S), wherein $PG^0$ is the un-protected PG group. For example, wherein the compound of formula (XIX-S) is de-protected to remove $PG^1$, then in the resulting compound of formula (X-S), $PG^0$ is $PG^2$. Alternatively, wherein the compound of formula (XIX-S) is de-protected to remove $PG^2$, then in the resulting compound of formula (X-S), $PG^0$ is $PG^1$.

The compound of formula (X-S) is reacted with a suitably substituted compound of formula (XVIII), wherein $Q^1$ is a suitably selected leaving group such as Br, Cl, I, and the like, preferably Cl, a known compound or compound prepared by known methods; wherein the compound of formula (XVIII) is preferably present in an amount in the range of from about 1.0 to about 3.0 molar equivalents, more preferably about 1.7 molar equivalents; in the presence of an organic base such as DIPEA, TEA, pyridine, and the like, preferably DIPEA; wherein the organic base is preferably present in an amount in the range of from about 1.5 to about 5.0 molar equivalents; more preferably about 2.0 molar equivalents; in an organic solvent such DMF and the like; preferably at a temperature in the range of from about 50° C. to about 120° C., more preferably at about 73° C.; to yield the corresponding compound of formula (XXI-S).

The compound of formula (XXI-S) is then de-protected according to known methods, as described herein, to yield the corresponding compound of formula (I-Sd).

The present invention is further directed to a process for the preparation of a compound of formula (I-A), as outlined in Scheme 10 below.

Scheme 10

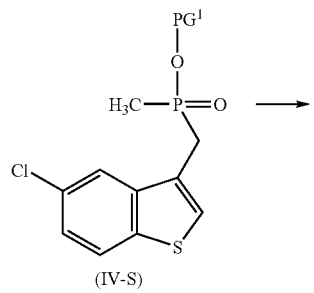

(IV-S)

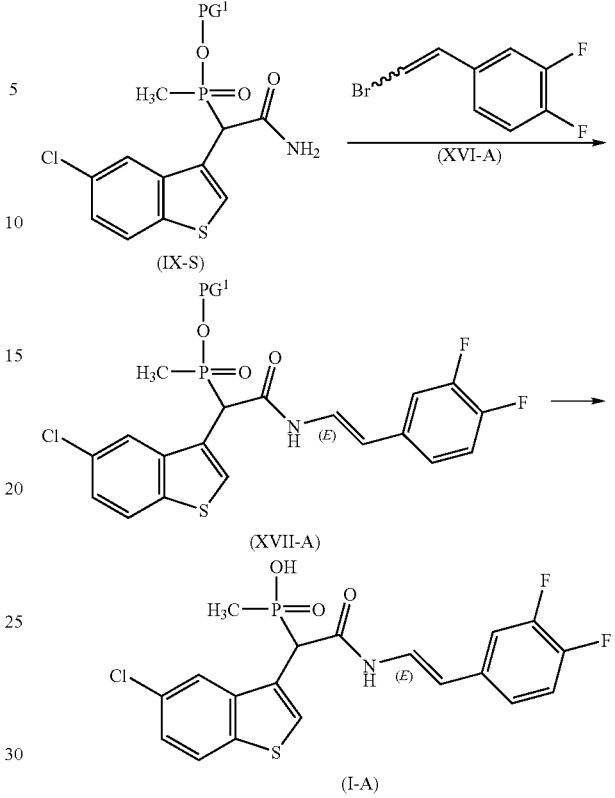

Accordingly, a suitably substituted compound of formula (IV-S), wherein $PG^1$ is a suitably substituted oxygen protecting group such as $C_{1-4}$alkyl, phenyl, benzyl, and the like, preferably, $PG^1$ is methyl, ethyl or t-butyl, more preferably, $PG^1$ is ethyl; is reacted according to any of the methods as described in Schemes 2 and 4 above; to yield the corresponding compound of formula (IX-S).

The compound of formula (IX-S) is reacted with a suitably substituted compound of formula (XVI-S); wherein the compound of formula (XVI-A) is preferably present in an excess of the corresponding trans orientation, more preferably, the compound of formula (XVI-A) is present in the corresponding trans orientation; wherein the compound of formula (XVI-A) is preferably present in an amount in the range of from about 1.0 to about 2.0 molar equivalents (relative to the moles of the compound of formula (IV-S)), more preferably in an amount in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as $Cs_2CO_3$, $K_2CO_3$, $K_3PO_4$, and the like, preferably $Cs_2CO_3$; wherein the inorganic base is preferably present in an amount in the range of from about 0.5 to about 2.0 molar equivalents, more preferably, in an amount in the range of from about 0.5 to about 3.0 molar equivalents, more preferably, in an amount of about 1.0 molar equivalents; in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents; in an organic solvent or mixtures thereof, such as DMA, N-methyl-pyrrolidinone, DMA/acetonitrile mixture, DMF, THF, and the like, preferably DMA; preferably at a temperature in the range of from about 50° C. to about 100° C., preferably at about 75° C.; to yield the corresponding compound of formula (IX-S).

Preferably, the compound of formula (IX-S) is reacted with the compound of formula (XVI-A) under an inert atmosphere, for example under nitrogen or argon. Preferably, a mixture of the compound of formula (IX-S), the CuI, the ligand, the inorganic base and the organic solvent is heated to a temperature in the range of from about 50° C. to about 100, to yield a homogeneous mixture; prior to addition of the compound of formula (XVI-A).

Preferably, in the reaction of the compound of formula (IX-S) with the compound of formula (XVI-A), the compound of formula (XVI-A) is present in an excess of its geometrical isomer, more particularly, its corresponding trans isomer, to yield the compound of formula (XVII-A) in its corresponding trans isomer. When the compound of formula (IX-S) is reacted with a compound of formula (XVI-A), wherein the compound of formula (XVI-A) is present in either its corresponding cis configuration or as a mixture of its corresponding cis and trans configurations, then the reaction proceeds to yield the compound of formula (XVII-A) as a mixture of its corresponding cis and trans configurations.

The compound of formula (XVII-A) is de-protected according to known methods, to yield the corresponding compound of formula (I-A). For example, the compound of formula (XVII-A) may be reacted with a suitably selected de-alkylating agent such as TMS-Br, TMS-I, $Br_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine; in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (I-A).

Alternatively, the compound of formula (XVII-A) may be reacted with a suitably selected de-alkylating agent such as TMS-Cl, and the like; in the presence of NaI, and the like; in an organic solvent such as acetonitrile, and the like; to yield the corresponding compound of formula (I-A).

The present invention is further directed to a process for the preparation of a compound of formula (I-B), as outlined in Scheme 11 below.

Scheme 11

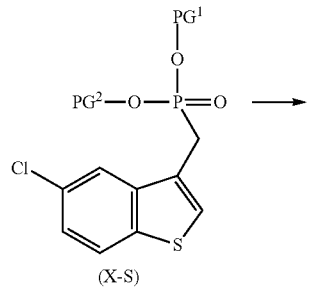

(X-S)

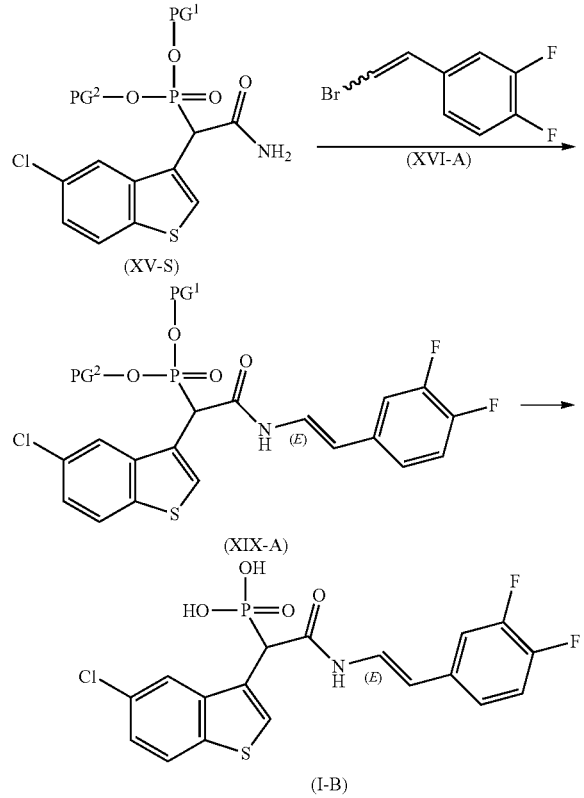

Accordingly, a suitably substituted compound of formula (X-S), wherein $PG^1$ is a suitably substituted oxygen protecting group such as $C_{1-4}$alkyl, phenyl, benzyl, and the like, preferably, $PG^1$ is methyl, ethyl or t-butyl, more preferably, $PG^1$ is ethyl; is reacted according to any of the methods as described in Schemes 3 and 5 above; to yield the corresponding compound of formula (XV-S).

The compound of formula (XV-S) is reacted with a suitably substituted compound of formula (XVI-A); wherein the compound of formula (XVI-A) is preferably present in an excess of the corresponding trans orientation, more preferably, the compound of formula (XVI-A) is present in the corresponding trans orientation; wherein the compound of formula (XVI-A) is preferably present in an amount in the range of from about 1.0 to about 2.0 molar equivalents (relative to the moles of the compound of formula (XV-S)), more preferably in an amount in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as $Cs_2CO_3$, $K_2CO_3$, $K_3PO_4$, and the like, preferably $Cs_2CO_3$; wherein the inorganic base is preferably present in an amount in the range of from about 0.5 to about 2.0 molar equivalents, more preferably, in an amount in the range of from about 0.5 to about 3.0 molar equivalents, more preferably, in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;
in an organic solvent or mixtures thereof, such as DMA, N-methyl-pyrrolidinone, DMA/acetonitrile mixture, DMF, THF, and the like, preferably DMA; preferably at a temperature in the range of from about 50° C. to about 100° C., preferably at about 75° C.; to yield the corresponding compound of formula (XIX-A).

Preferably, the compound of formula (XV-S) is reacted with the compound of formula (XVI-A) under an inert atmosphere, for example under nitrogen or argon. Preferably, a mixture of the compound of formula (XV-S), the CuI, the ligand, the inorganic base and the organic solvent is heated to a temperature in the range of from about 50° C. to about 100, to yield a homogeneous mixture; prior to addition of the compound of formula (XVI-A).

Preferably, in the reaction of the compound of formula (XV-S) with the compound of formula (XVI-A), the compound of formula (XVI-A) is present in an excess of its geometrical isomer, more particularly, its corresponding trans isomer, to yield the compound of formula (XIX-A) in its corresponding trans isomer. When the compound of formula (XV-S) is reacted with a compound of formula (XVI-A), wherein the compound of formula (XVI-A) is present in either its corresponding cis configuration or as a mixture of its corresponding cis and trans configurations, then the reaction proceeds to yield the compound of formula (XIX-A) as a mixture of its corresponding cis and trans configurations.

The compound of formula (XIX-A) is de-protected according to known methods, to yield the corresponding compound of formula (I-B). For example, the compound of formula (XIX-A) may be reacted with a suitably selected de-alkylating agent such as TMS-Br, TMS-I, $Br_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine; in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (I-B).

Alternatively, the compound of formula (XIX-A) may be reacted with a suitably selected de-alkylating agent such as TMS-Cl, and the like; in the presence of NaI, and the like; in an organic solvent such as acetonitrile, and the like; to yield the corresponding compound of formula (I-B).

The present invention is further directed to a process for the preparation of a compound of formula (I-C), as outlined in Scheme 12 below.

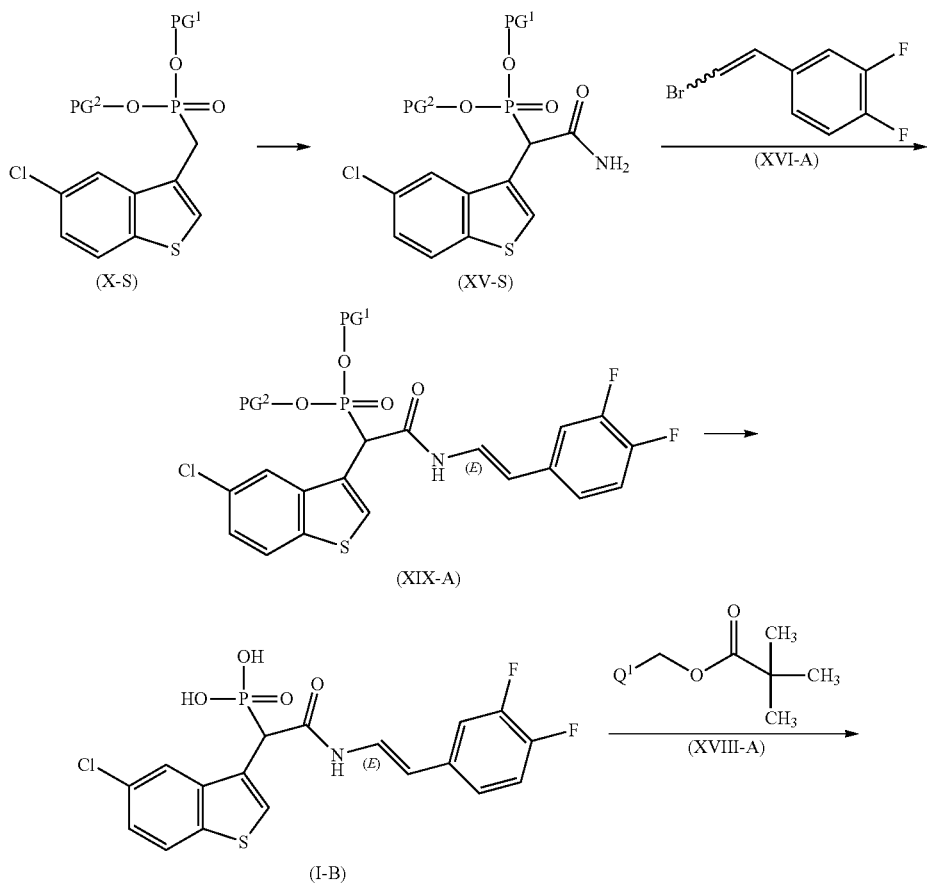

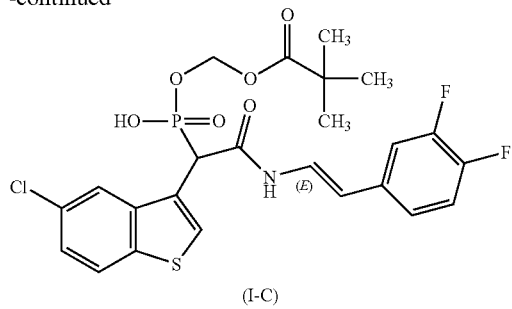

(I-C)

Accordingly, a suitably substituted compound of formula (X-S), wherein PG$^1$ is a suitably substituted oxygen protecting group such as C$_{1-4}$alkyl, phenyl, benzyl, and the like, preferably, PG$^1$ is methyl, ethyl or t-butyl, more preferably, PG$^1$ is ethyl; is reacted according to any of the methods as described in Schemes 3 and 5 above; to yield the corresponding compound of formula (XV-5).

The compound of formula (XV-S) is reacted with a suitably substituted compound of formula (XVI-A); wherein the compound of formula (XVI-A) is preferably present in an excess of the corresponding trans orientation, more preferably, the compound of formula (XVI-A) is present in the corresponding trans orientation; wherein the compound of formula (XVI-A) is preferably present in an amount in the range of from about 1.0 to about 2.0 molar equivalents (relative to the moles of the compound of formula (XV-S)), more preferably in an amount in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as Cs$_2$CO$_3$, K$_2$CO$_3$, K$_3$PO$_4$, and the like, preferably Cs$_2$CO$_3$; wherein the inorganic base is preferably present in an amount in the range of from about 0.5 to about 2.0 molar equivalents, more preferably, in an amount in the range of from about 0.5 to about 3.0 molar equivalents, more preferably in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;

in an organic solvent or mixtures thereof, such as DMA, N-methyl-pyrrolidinone, DMA/acetonitrile mixture, DMF, THF, and the like, preferably DMA; preferably at a temperature in the range of from about 50° C. to about 100° C., preferably at about 75° C.; to yield the corresponding compound of formula (XIX-A).

Preferably, the compound of formula (XV-S) is reacted with the compound of formula (XVI-A) under an inert atmosphere, for example under nitrogen or argon. Preferably, a mixture of the compound of formula (XV-S), the CuI, the ligand, the inorganic base and the organic solvent is heated to a temperature in the range of from about 50° C. to about 100, to yield a homogeneous mixture; prior to addition of the compound of formula (XVI-A).

Preferably, in the reaction of the compound of formula (XV-S) with the compound of formula (XVI-A), the compound of formula (XVI-A) is present in an excess of its geometrical isomer, more particularly, its corresponding trans isomer, to yield the compound of formula (XIX-A) in its corresponding trans isomer. When the compound of formula (XV-S) is reacted with a compound of formula (XVI-A), wherein the compound of formula (XVI-A) is present in either its corresponding cis configuration or as a mixture of its corresponding cis and trans configurations, then the reaction proceeds to yield the compound of formula (XIX-A) as a mixture of its corresponding cis and trans configurations.

The compound of formula (XIX-A) is de-protected according to known methods, to yield the corresponding compound of formula (I-B). For example, the compound of formula (XIX-A) may be reacted with a suitably selected de-alkylating agent such as TMS-Br, TMS-I, Br$_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine; in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (I-B).

Alternatively, the compound of formula (XIX-A) may be reacted with a suitably selected de-alkylating agent such as TMS-Cl, and the like; in the presence of NaI, and the like; in an organic solvent such as acetonitrile, and the like; to yield the corresponding compound of formula (I-B).

The compound of formula (I-B) is reacted with a suitably substituted compound of formula (XVIII-A), wherein Q$^1$ is a suitably selected leaving group such as Br, Cl, I, and the like, preferably Cl, a known compound or compound prepared by known methods; wherein the compound of formula (XVIII-A) is preferably present in an amount in the range of from about 1.0 to about 3.0 molar equivalents, more preferably about 1.7 molar equivalents; in the presence of an organic base such as DIPEA, TEA, pyridine, and the like, preferably DIPEA; wherein the organic base is preferably present in an amount in the range of from about 1.5 to about 5.0 molar equivalents; more preferably about 2.0 molar equivalents; in an organic solvent such DMF and the like; preferably at a temperature in the range of from about 50° C. to about 120° C., more preferably at about 73° C.; to yield the corresponding compound of formula (X-C).

The present invention is further directed to a process for the preparation of a compound of formula (I-D) as outlined in Scheme 13 below.

Scheme 13

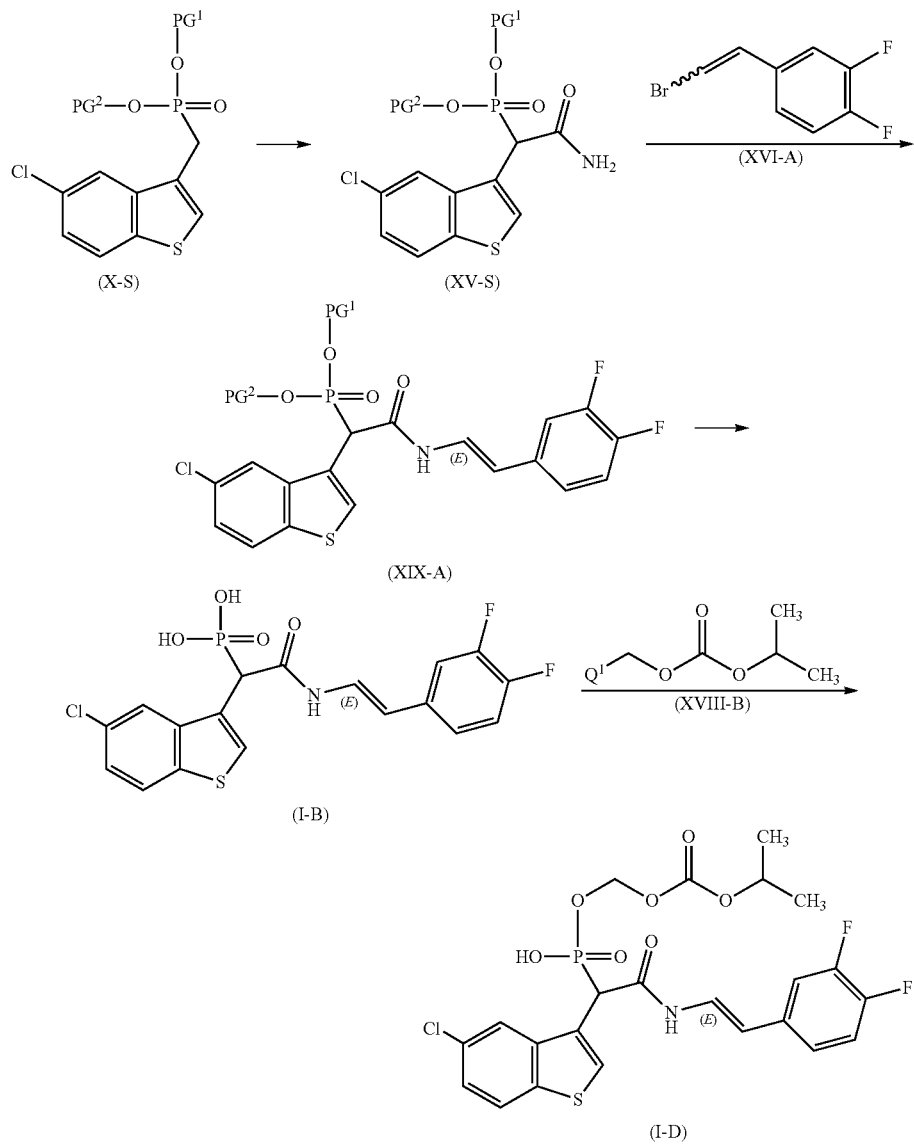

Accordingly, a suitably substituted compound of formula (X-S), wherein PG$^1$ is a suitably substituted oxygen protecting group such as C$_{1-4}$alkyl, phenyl, benzyl, and the like, preferably, PG$^1$ is methyl, ethyl or t-butyl, more preferably, PG$^1$ is ethyl; is reacted according to any of the methods as described in Schemes 3 and 5, above; to yield the corresponding compound of formula (XV-S).

The compound of formula (XV-S) is reacted with a suitably substituted compound of formula (XVI-A); wherein the compound of formula (XVI-A) is preferably present in an excess of the corresponding trans orientation, more preferably, the compound of formula (XVI-A) is present in the corresponding trans orientation; wherein the compound of formula (XVI-A) is preferably present in an amount in the range of from about 1.0 to about 2.0 molar equivalents (relative to the moles of the compound of formula (XV-S)), more preferably in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as Cs$_2$CO$_3$, K$_2$CO$_3$, K$_3$PO$_4$, and the like, preferably Cs$_2$CO$_3$; wherein the inorganic base is preferably present in an amount in the range of from about 0.5 to about 2.0 molar equivalents, more preferably, in an amount in the range of from about 0.5 to about 3.0 molar equivalents, more preferably, in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;

in an organic solvent or mixtures thereof, such as DMA, N-methyl-pyrrolidinone, DMA/acetonitrile mixture, DMF, THF, and the like, preferably DMA; preferably at a temperature in the range of from about 50° C. to about 100° C., preferably at about 75° C.; to yield the corresponding compound of formula (XIX-A).

Preferably, the compound of formula (XV-S) is reacted with the compound of formula (XVI-A) under an inert atmosphere, for example under nitrogen or argon. Preferably, a mixture of the compound of formula (XV-S), the CuI, the ligand, the inorganic base and the organic solvent is heated to a temperature in the range of from about 50° C. to about 100, to yield a homogeneous mixture; prior to addition of the compound of formula (XVI-A).

Preferably, in the reaction of the compound of formula (XV-S) with the compound of formula (XVI-A), the compound of formula (XVI-A) is present in an excess of its geometrical isomer, more particularly, its corresponding trans isomer, to yield the compound of formula (XIX-A) in its corresponding trans isomer. When the compound of formula (XV-S) is reacted with a compound of formula (XVI-A), wherein the compound of formula (XVI-A) is present in either its corresponding cis configuration or as a mixture of its corresponding cis and trans configurations, then the reaction proceeds to yield the compound of formula (XIX-A) as a mixture of its corresponding cis and trans configurations.

The compound of formula (XIX-A) is de-protected according to known methods, to yield the corresponding compound of formula (I-B). For example, the compound of formula (XIX-A) may be reacted with a suitably selected de-alkylating agent such as TMS-Br, TMS-I, $Br_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine; in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (I-B).

Alternatively, the compound of formula (XIX-A) may be reacted with a suitably selected de-alkylating agent such as TMS-Cl, and the like; in the presence of NaI, and the like; in an organic solvent such as acetonitrile, and the like; to yield the corresponding compound of formula (I-B).

The compound of formula (I-B) is reacted with a suitably substituted compound of formula (XVIII-B), wherein $Q^1$ is a suitably selected leaving group such as Br, Cl, I, and the like, preferably Cl, a known compound or compound prepared by known methods; wherein the compound of formula (XVIII-B) is preferably present in an amount in the range of from about 1.0 to about 3.0 molar equivalents, more preferably about 1.7 molar equivalents; in the presence of an organic base such as DIPEA, TEA, pyridine, and the like, preferably DIPEA; wherein the organic base is preferably present in an amount in the range of from about 1.5 to about 5.0 molar equivalents; more preferably about 2.0 molar equivalents; in an organic solvent such DMF and the like; preferably at a temperature in the range of from about 50° C. to about 120° C., more preferably at about 73° C.; to yield the corresponding compound of formula (I-D).

The present invention is further directed to a process for the preparation of a compound of formula (I-E), as outlined in Scheme 14 below.

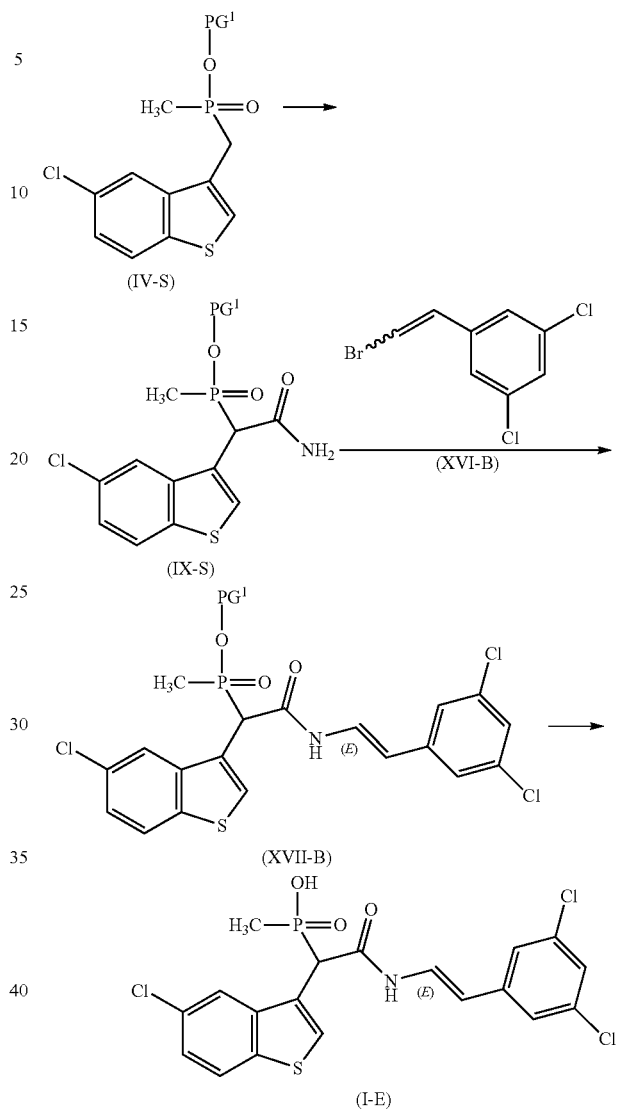

Scheme 14

Accordingly, a suitably substituted compound of formula (IV-S), wherein $PG^1$ is a suitably substituted oxygen protecting group such as $C_{1-4}$alkyl, phenyl, benzyl, and the like, preferably, $PG^1$ is methyl, ethyl or t-butyl, more preferably, $PG^1$ is ethyl; is reacted according to any of the methods as described in Scheme 2 and 4 above; to yield the corresponding compound of formula (IX-S).

The compound of formula (IX-S) is reacted with a suitably substituted compound of formula (XVI-B); wherein the compound of formula (XVI-B) is preferably present in an excess of the corresponding trans orientation, more preferably, the compound of formula (XVI-B) is present in the corresponding trans orientation; wherein the compound of formula (XVI-B) is preferably present in an amount in the range of from about 1.0 to about 2.0 molar equivalents (relative to the moles of the compound of formula (IX-S)), more preferably in an amount in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as $Cs_2CO_3$, $K_2CO_3$, $K_3PO_4$, and the like, preferably $Cs_2CO_3$; wherein the inorganic base is preferably present in an amount in the range of from about 0.5 to about 2.0 molar equivalents, more preferably, in an amount in the range of from about 0.5 to about 3.0 molar equivalents, more preferably, in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;

in an organic solvent or mixtures thereof, such as DMA, N-methyl-pyrrolidinone, DMA/acetonitrile mixture, DMF, THF, and the like, preferably DMA; preferably at a temperature in the range of from about 50° C. to about 100° C., preferably at about 75° C.; to yield the corresponding compound of formula (XVII-B).

Preferably, the compound of formula (IX-S) is reacted with the compound of formula (XVI-B) under an inert atmosphere, for example under nitrogen or argon. Preferably, a mixture of the compound of formula (IX-S), the CuI, the ligand, the inorganic base and the organic solvent is heated to a temperature in the range of from about 50° C. to about 100, to yield a homogeneous mixture; prior to addition of the compound of formula (XVI-B).

Preferably, in the reaction of the compound of formula (IX-S) with the compound of formula (XVI-B), the compound of formula (XVI-B) is present in an excess of its geometrical isomer, more particularly, its corresponding trans isomer, to yield the compound of formula (XVII-B) in its corresponding trans isomer. When the compound of formula (IX-S) is reacted with a compound of formula (XVI-B), wherein the compound of formula (XVI-B) is present in either its corresponding cis configuration or as a mixture of its corresponding cis and trans configurations, then the reaction proceeds to yield the compound of formula (XVII-B) as a mixture of its corresponding cis and trans configurations.

The compound of formula (XVII-B) is de-protected according to known methods, to yield the corresponding compound of formula (I-E). For example, the compound of formula (XVII-B) may be reacted with a suitably selected de-alkylating agent such as TMS-Br, TMS-1, $Br_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine; in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (I-E).

Alternatively, the compound of formula (XVII-B) may be reacted with a suitably selected de-alkylating agent such as TMS-Cl, and the like; in the presence of NaI, and the like; in an organic solvent such as acetonitrile, and the like; to yield the corresponding compound of formula (I-E).

The present invention is further directed to a process for the preparation of a compound of formula (I-F), as outlined in Scheme 15 below.

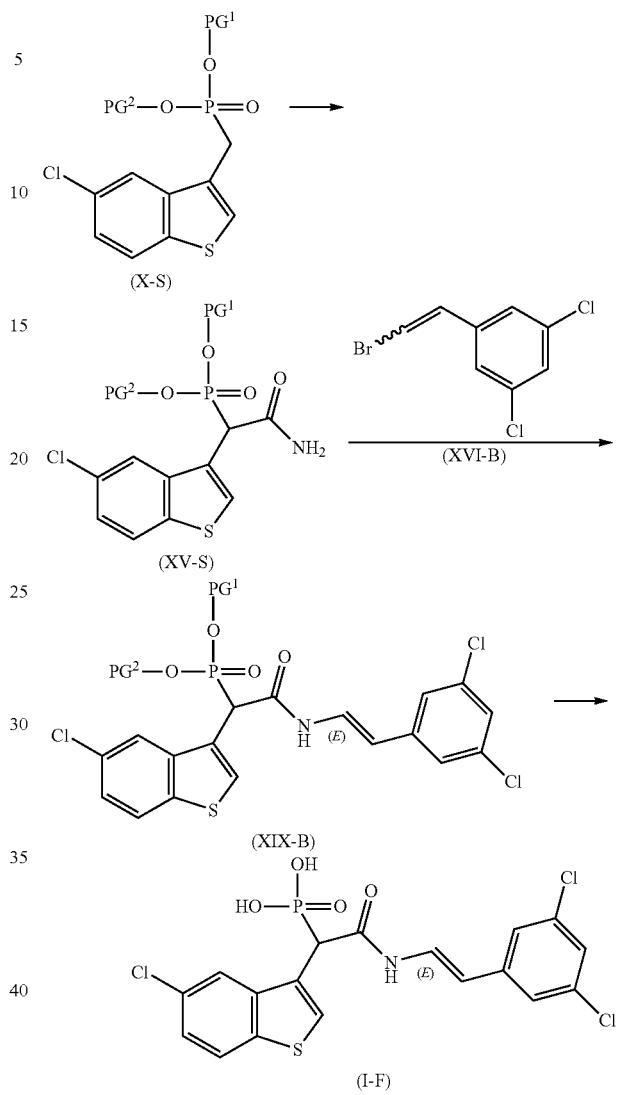

Scheme 15

Accordingly, a suitably substituted compound of formula (X-S), wherein $PG^1$ is a suitably substituted oxygen protecting group such as $C_{1-4}$alkyl, phenyl, benzyl, and the like, preferably, $PG^1$ is methyl, ethyl or t-butyl, more preferably, $PG^1$ is ethyl; is reacted according to any of the methods as described in Schemes 3 and 5 above; to yield the corresponding compound of formula (XV-S).

The compound of formula (XV-S) is reacted with a suitably substituted compound of formula (XVI-B); wherein the compound of formula (XVI-B) is preferably present in an excess of the corresponding trans orientation, more preferably, the compound of formula (XVI-B) is present in the corresponding trans orientation; wherein the compound of formula (XVI-B) is preferably present in an amount in the range of from about 1.0 to about 2.0 molar equivalents (relative to the moles of the compound of formula (X-B)), more preferably in an amount in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as Cs$_2$CO$_3$, K$_2$CO$_3$, K$_3$PO$_4$, and the like, preferably Cs$_2$CO$_3$; wherein the inorganic base is preferably present in an amount in the range of from about 0.5 to about 2.0 molar equivalents, more preferably, in an amount in the range of from about 0.5 to about 3.0 molar equivalents, more preferably, in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;

in an organic solvent or mixtures thereof, such as DMA, N-methyl-pyrrolidinone, DMA/acetonitrile mixture, DMF, THF, and the like, preferably DMA; preferably at a temperature in the range of from about 50° C. to about 100° C., preferably at about 75° C.; to yield the corresponding compound of formula (XIX-B).

Preferably, the compound of formula (XV-S) is reacted with the compound of formula (XVI-B) under an inert atmosphere, for example under nitrogen or argon. Preferably, a mixture of the compound of formula (XV-S), the CuI, the ligand, the inorganic base and the organic solvent is heated to a temperature in the range of from about 50° C. to about 100, to yield a homogeneous mixture; prior to addition of the compound of formula (XVI-B).

Preferably, in the reaction of the compound of formula (XV-S) with the compound of formula (XVI-B), the compound of formula (XVI-B) is present in an excess of its geometrical isomer, more particularly, its corresponding trans isomer, to yield the compound of formula (XIX-B) in its corresponding trans isomer. When the compound of formula (XV-S) is reacted with a compound of formula (XVI-B), wherein the compound of formula (XVI-B) is present in either its corresponding cis configuration or as a mixture of its corresponding cis and trans configurations, then the reaction proceeds to yield the compound of formula (XIX-B) as a mixture of its corresponding cis and trans configurations.

The compound of formula (XIX-B) is de-protected according to known methods, to yield the corresponding compound of formula (I-F). For example, the compound of formula (XIX-B) may be reacted with a suitably selected de-alkylating agent such as TMS-Br, TMS-I, Br$_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine; in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (I-F).

Alternatively, the compound of formula (XIX-B) may be reacted with a suitably selected de-alkylating agent such as TMS-Cl, and the like; in the presence of NaI, and the like; in an organic solvent such as acetonitrile, and the like; to yield the corresponding compound of formula (I-F).

The present invention is further directed to a process for the preparation of a compound of formula (I-G), as outlined in Scheme 16 below.

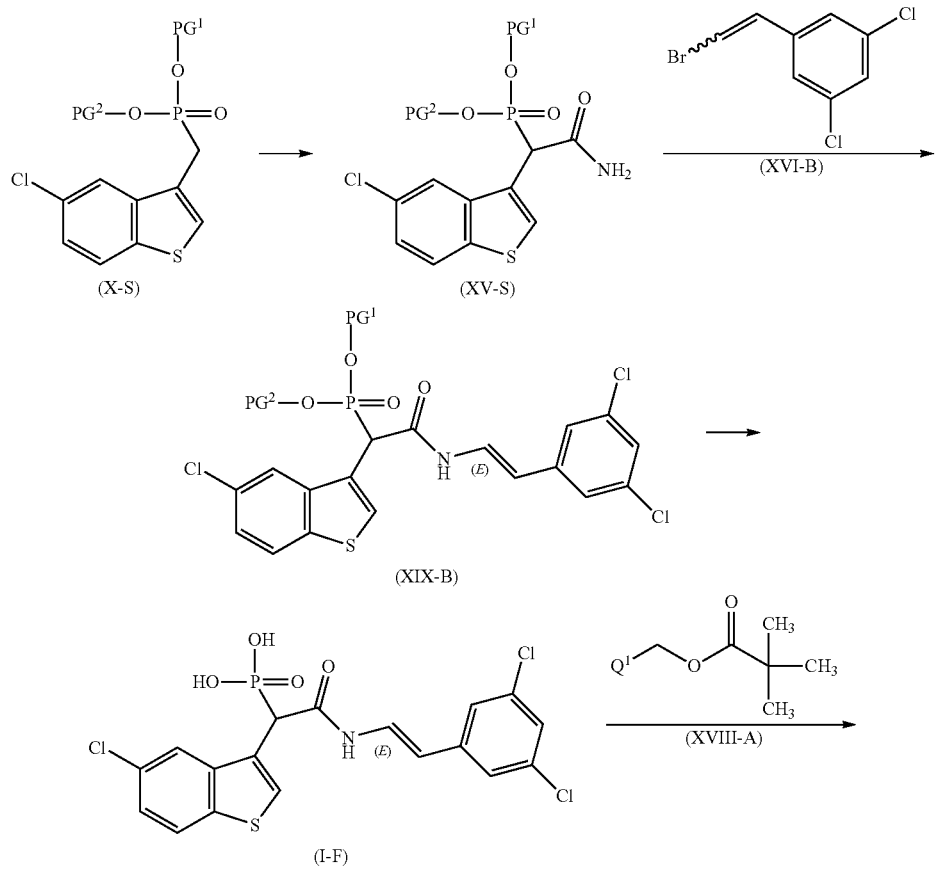

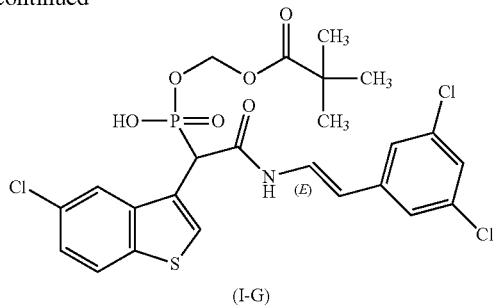

(I-G)

Accordingly, a suitably substituted compound of formula (X-S), wherein $PG^1$ is a suitably substituted oxygen protecting group such as $C_{1-4}$alkyl, phenyl, benzyl, and the like, preferably, $PG^1$ is methyl, ethyl or t-butyl, more preferably, $PG^1$ is ethyl; is reacted according to any of the methods as described in Schemes 3 and 5 above; to yield the corresponding compound of formula (XV-S).

The compound of formula (XV-S) is reacted with a suitably substituted compound of formula (XVI-B); wherein the compound of formula (XVI-B) is preferably present in an excess of the corresponding trans orientation, more preferably, the compound of formula (XVI-B) is present in the corresponding trans orientation; wherein the compound of formula (XVI-B) is preferably present in an amount in the range of from about 1.0 to about 2.0 molar equivalents (relative to the moles of the compound of formula (X-B)), more preferably in an amount in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as $Cs_2CO_3$, $K_2CO_3$, $K_3PO_4$, and the like, preferably $Cs_2CO_3$; wherein the inorganic base is preferably present in an amount in the range of from about 0.5 to about 2.0 molar equivalents, more preferably, in an amount in the range of from about 0.5 to about 3.0 molar equivalents, more preferably, in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;

in an organic solvent or mixtures thereof, such as DMA, N-methyl-pyrrolidinone, DMA/acetonitrile mixture, DMF, THF, and the like, preferably DMA; preferably at a temperature in the range of from about 50° C. to about 100° C., preferably at about 75° C.; to yield the corresponding compound of formula (XIX-B).

Preferably, the compound of formula (XV-S) is reacted with the compound of formula (XVI-B) under an inert atmosphere, for example under nitrogen or argon. Preferably, a mixture of the compound of formula (XV-S), the CuI, the ligand, the inorganic base and the organic solvent is heated to a temperature in the range of from about 50° C. to about 100, to yield a homogeneous mixture; prior to addition of the compound of formula (XVI-B).

Preferably, in the reaction of the compound of formula (XV-S) with the compound of formula (XVI-B), the compound of formula (XVI-B) is present in an excess of its geometrical isomer, more particularly, its corresponding trans isomer, to yield the compound of formula (XIX-B) in its corresponding trans isomer. When the compound of formula (XV-S) is reacted with a compound of formula (XVI-B), wherein the compound of formula (XVI-B) is present in either its corresponding cis configuration or as a mixture of its corresponding cis and trans configurations, then the reaction proceeds to yield the compound of formula (XIX-B) as a mixture of its corresponding cis and trans configurations.

The compound of formula (XIX-B) is de-protected according to known methods, to yield the corresponding compound of formula (I-F). For example, the compound of formula (XIX-B) may be reacted with a suitably selected de-alkylating agent such as TMS-Br, TMS-I, $Br_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine; in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (I-F).

Alternatively, the compound of formula (XIX-B) may be reacted with a suitably selected de-alkylating agent such as TMS-Cl, and the like; in the presence of NaI, and the like; in an organic solvent such as acetonitrile, and the like; to yield the corresponding compound of formula (I-F).

The compound of formula (I-F) is reacted with a suitably substituted compound of formula (XVIII-A), wherein $Q^1$ is a suitably selected leaving group such as Br, Cl, I, and the like, preferably Cl, a known compound or compound prepared by known methods; wherein the compound of formula (XVIII-A) is preferably present in an amount in the range of from about 1.0 to about 3.0 molar equivalents, more preferably about 1.7 molar equivalents; in the presence of an organic base such as DIPEA, TEA, pyridine, and the like, preferably DIPEA; wherein the organic base is preferably present in an amount in the range of from about 1.5 to about 5.0 molar equivalents; more preferably about 2.0 molar equivalents; in an organic solvent such DMF and the like; preferably at a temperature in the range of from about 50° C. to about 120° C., more preferably at about 73° C.; to yield the corresponding compound of formula (I-G).

The present invention is further directed to a process for the preparation of a compound of formula (X-H), as outlined in Scheme 17 below.

Scheme 17

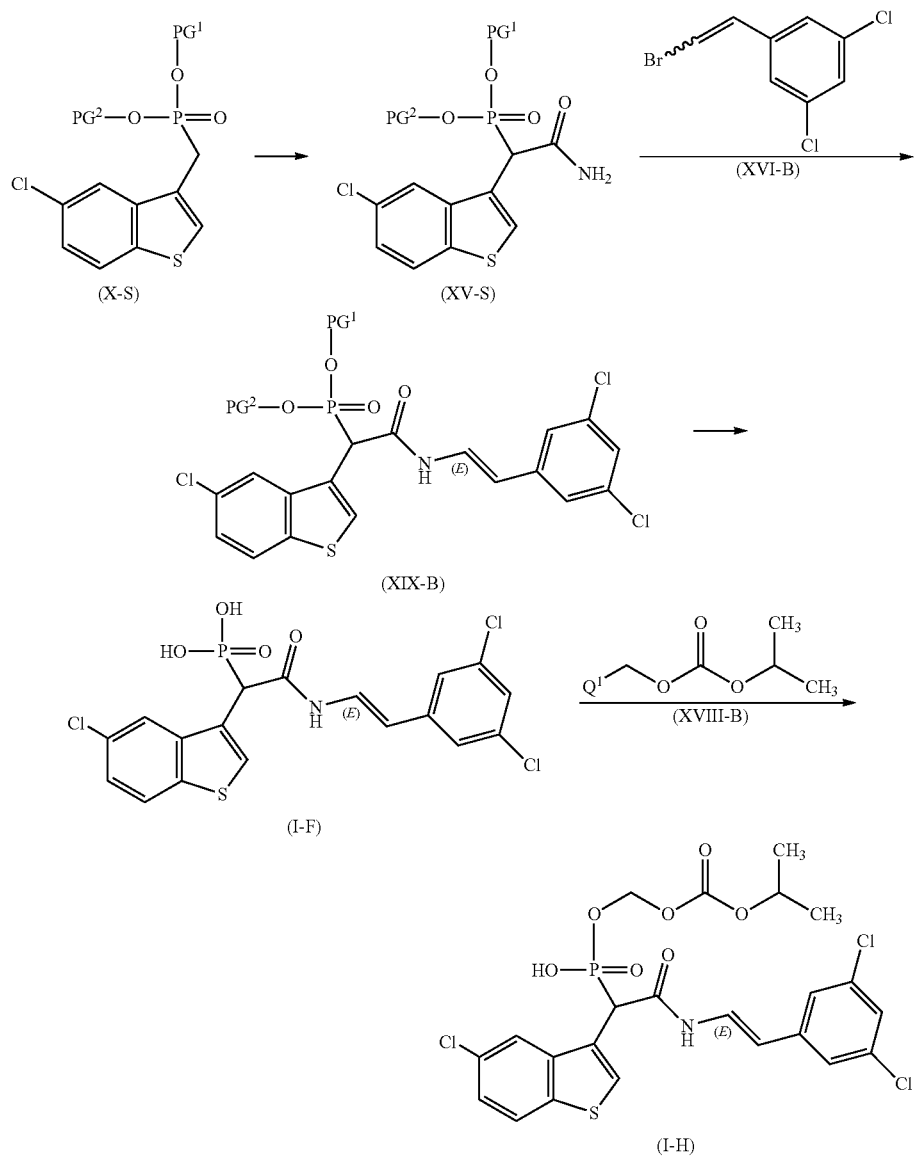

Accordingly, a suitably substituted compound of formula (X-S), wherein PG[1] is a suitably substituted oxygen protecting group such as $C_{1-4}$alkyl, phenyl, benzyl, and the like, preferably, PG[1] is methyl, ethyl or t-butyl, more preferably, PG[1] is ethyl; is reacted according to any of the methods as described in Schemes 3 and 5 above; to yield the corresponding compound of formula (XV-S).

The compound of formula (XV-S) is reacted with a suitably substituted compound of formula (XVI-B); wherein the compound of formula (XVI-B) is preferably present in an excess of the corresponding trans orientation, more preferably, the compound of formula (XVI-B) is present in the corresponding trans orientation; wherein the compound of formula (XVI-B) is preferably present in an amount in the range of from about 1.0 to about 2.0 molar equivalents (relative to the moles of the compound of formula (X-B)), more preferably in an amount in the range of from about 1.0 to about 1.5 molar equivalents, more preferably still in an amount of about 1.1 to about 1.2 molar equivalents;

in the presence of CuI, and the like, wherein the CuI is preferably present in an amount in the range of from about 0.1 to about 1.0 molar equivalents, more preferably, in an amount in the range of from about 0.1 to about 0.5 molar equivalents, more preferably in an amount of about 0.2 molar equivalents;

in the presence of an inorganic base, such as $Cs_2CO_3$, $K_2CO_3$, $K_3PO_4$, and the like, preferably $Cs_2CO_3$; wherein the inorganic base is preferably present in an amount in the range of from about 0.5 to about 2.0 molar equivalents, more preferably, in an amount in the range of from about 0.5 to about 3.0 molar equivalents, more preferably, in an amount of about 1.0 molar equivalents;

in the presence of a suitably selected ligand such as N,N-dimethylethylenediamine, N,N-dimethylglycine, dicyclohexyldiamine, and the like, preferably, N,N-dimethylethylenediamine; wherein the ligand is preferably present in an amount in the range of from about 0.2 to about 2.0 molar equivalents, more preferably, in an amount in the range of from about 0.2 to about 1.0 molar equivalents, more preferably, in an amount of about 0.4 molar equivalents;

in an organic solvent or mixtures thereof, such as DMA, N-methyl-pyrrolidinone, DMA/acetonitrile mixture, DMF, THF, and the like, preferably DMA; preferably at a temperature in the range of from about 50° C. to about 100° C., preferably at about 75° C.; to yield the corresponding compound of formula (XIX-B).

Preferably, the compound of formula (XV-S) is reacted with the compound of formula (XVI-B) under an inert atmosphere, for example under nitrogen or argon. Preferably, a mixture of the compound of formula (XV-S), the CuI, the ligand, the inorganic base and the organic solvent is heated to a temperature in the range of from about 50° C. to about 100, to yield a homogeneous mixture; prior to addition of the compound of formula (XVI-B).

Preferably, in the reaction of the compound of formula (XV-S) with the compound of formula (XVI-B), the compound of formula (XVI-B) is present in an excess of its geometrical isomer, more particularly, its corresponding trans isomer, to yield the compound of formula (XIX-B) in its corresponding trans isomer. When the compound of formula (XV-S) is reacted with a compound of formula (XVI-B), wherein the compound of formula (XVI-B) is present in either its corresponding cis configuration or as a mixture of its corresponding cis and trans configurations, then the reaction proceeds to yield the compound of formula (XIX-B) as a mixture of its corresponding cis and trans configurations.

The compound of formula (XIX-B) is de-protected according to known methods, to yield the corresponding compound of formula (I-F). For example, the compound of formula (XIX-B) may be reacted with a suitably selected de-alkylating agent such as TMS-Br, TMS-I, $Br_3$, and the like; wherein the de-alkylating agent is preferably present in an amount of about 2.0 molar equivalents; in the presence of a proton scavenger such as pyridine, N-methylmorpholine, proton sponge (i.e. N,N,N',N'-tetramethyl-1,8-diaminonaphthalene), and the like, preferably pyridine; in an organic solvent such as acetonitrile, DCM, DCE, and the like, preferably acetonitrile; preferably at a temperature in the range of from about 10° C. to about 30° C., more preferably at about 10° C.; to yield the corresponding compound of formula (I-F).

Alternatively, the compound of formula (XIX-B) may be reacted with a suitably selected de-alkylating agent such as TMS-Cl, and the like; in the presence of NaI, and the like; in an organic solvent such as acetonitrile, and the like; to yield the corresponding compound of formula (I-F).

The compound of formula (I-F) is reacted with a suitably substituted compound of formula (XVIII-B), wherein $Q^1$ is a suitably selected leaving group such as Br, Cl, I, and the like, preferably Cl, a known compound or compound prepared by known methods; wherein the compound of formula (XVIII-B) is preferably present in an amount in the range of from about 1.0 to about 3.0 molar equivalents, more preferably about 1.7 molar equivalents; in the presence of an organic base such as DIPEA, TEA, pyridine, and the like, preferably DIPEA; wherein the organic base is preferably present in an amount in the range of from about 1.5 to about 5.0 molar equivalents; more preferably about 2.0 molar equivalents; in an organic solvent such DMF and the like; preferably at a temperature in the range of from about 50° C. to about 120° C., more preferably at about 73° C.; to yield the corresponding compound of formula (I-H).

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

{(5-Chloro-benzo[b]thiophen-3-yl)-[2-(3,4-difluoro-phenyl)-vinylcarbamoyl]-methyl}-methyl-phosphinic acid ethyl ester

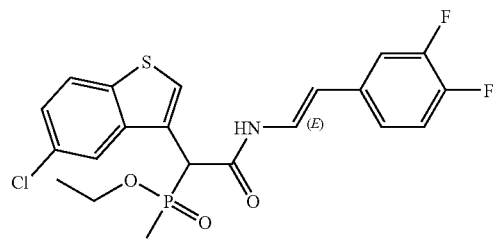

Cesium Carbonate Method:

A 3 L 4-necked round-bottomed flask equipped with addition funnel, mechanical stirrer, nitrogen inlet, heating mantle and thermocouple was charged with [carbamoyl-(5-chloro-benzo[b]thiophen-3-yl)-methyl]-methyl-phosphinic acid ethyl ester (100 g, 0.3 mol), $Cs_2CO_3$ (58.6 g, 0.18 mol), N,N-dimethylacetamide (DMA) (300 mL, anhydrous 99.8%), N,N'-dimethyl-ethylenediamine (10.6 g, 0.12 mol) and copper (I) iodide (11.4 g, 0.06 mol) and the resulting mixture heated to about 80° C., under nitrogen. To the resulting mixture was then added a solution of 4-(2-bromo-vinyl)-1,2-difluoro-benzene (78.8 g, 0.36 mol) in DMA (30 mL), slowly over a period of about 20 min and the resulting mixture stirred at this temperature for 5 hours. The resulting mixture was then quenched while hot with $H_2O$ (600 mL), and diluted with EtOAc (700 mL), added slowly through an addition funnel. The resulting biphasic mixture was cooled to 50-55° C. and at this temperature the layers were separated. The organic layer was washed with $H_2O$ (500 mL), 0.5N HCl aqueous solution (500 mL) and brine (500 mL), then filtered and concentrated under reduced pressure to approximately half the original volume (350-400 mL). The concentrated solution was heated to slow reflux. Heptane (250 mL) was then added slowly at this temperature. The resulting suspension was cooled to 5-10° C. over a period of 1 hr, diluted with additional heptane (100 mL) and aged at this temperature for a period of about 2 hrs. The resulting solid precipitate was filtered, rinsed with cold heptane/EtOAc (4/1) solvent mixture (100 ml), and dried at 55° C. in a vacuum oven overnight, to yield the title compound as a white solid.

HPLC on a sample of the isolated product indicated 95% purity.

EXAMPLE 2

{(5-Chloro-benzo[b]thiophen-3-yl)-[2-(3,4-difluoro-phenyl)-vinylcarbamoyl]-methyl}-methyl-phosphinic acid ethyl ester

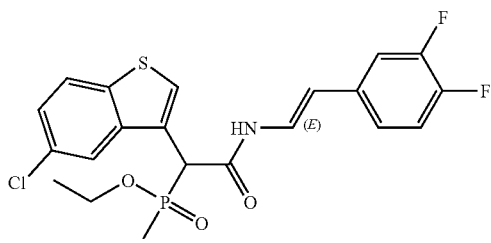

Potassium Carbonate Method:

A 3 L 4-necked round-bottomed flask equipped with addition funnel, mechanical stirrer, nitrogen inlet, heating mantle and thermocouple was charged with [carbamoyl-(5-chloro-benzo[b]thiophen-3-yl)-methyl]-methyl-phosphinic acid ethyl ester (10.5 g, 0.03 mol), $K_2CO_3$ (8.0 g, 0.03 mol), N,N-dimethylacetamide (DMA) (40 mL, anhydrous 99.8%), N,N'-dimethyl-ethylenediamine (1.6 g, 0.018 mol) and copper (I) iodide (1.14 g, 0.006 mol) and the resulting mixture heated to about 80° C. under nitrogen. To the resulting mixture was then added 4-(2-bromo-vinyl)-1,2-difluoro-benzene (7.9 g, 0.036 mol) slowly, over a about 20 minutes, at 80° C. and the resulting mixture stirred at this temperature for about 5 hours. The resulting mixture was then quenched while hot with $H_2O$ (60 mL), and diluted with EtOAc (70 mL), added slowly through an addition funnel. The resulting biphasic mixture was cooled to 50-55° C. and at this temperature the layers were separated. The organic layer was washed with $H_2O$ (50 mL), 0.5N HCl aq.solution (50 mL) and brine (50 mL), then filtered and concentrated under reduced pressure to about half the original volume (35-40 mL). The concentrated solution was heated to slow reflux and then heptane (25 mL) was added slowly at this temperature. The resulting suspension was cooled to 5-10° C. over a period of 1 hr, diluted with additional heptane (10 mL) and aged at this temperature for about 2 hrs. The resulting solid precipitate was filtered, rinsed with cold heptane/EtOAc (4/1) solvent mixture (10 ml), and dried 55° C. in a vacuum oven overnight, to yield the title compound as a white solid.

HPLC on a sample of the isolated product indicated 95% purity.

EXAMPLE 3

{(5-Chloro-benzo[b]thiophen-3-yl)-[2-(3,4-difluoro-phenyl)-vinylcarbamoyl]-methyl}-methyl-phosphinic acid

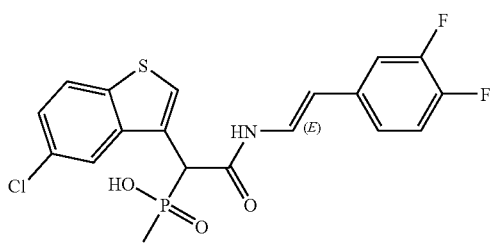

A 1 L four-necked round-bottomed flask equipped with mechanical stirrer, addition funnel, condenser, and a thermocouple was charged with {(5-Chloro-benzo[b]thiophen-3-yl)-[2-(3,4-difluoro-phenyl)-vinylcarbamoyl]methyl}-methyl-phosphinic acid ethyl ester (26.4 g, 0.056 mol), acetonitrile (200 mL) and pyridine (11.0 mL, 0.136 mol). To the resulting mixture was then added bromotrimethylsilane (15.5 mL, 0.117 mol), 15 minutes, while maintaining the temperature of the resulting mixture below about 30° C. The mixture was then stirred for an additional 15 minutes to yield a clear yellow solution, which was aged for about 2 hours. The resulting mixture was then cooled to about 0-5° C. To the mixture was then added concentrated sulfuric acid (5.4 mL) in water (90 mL), using vigorous agitation. To the resulting mixture was then added MTBE (150 mL) and the mixture aged with stirring until two homogeneous layers were obtained. The layers were separated and the organic layer was washed twice with water (45 mL) and then concentrated to yield a residue. The residue was digested with methanol (180 mL) under vigorous stirring. then concentrated to about 50% of its original volume under reduced pressure. The resulting slurry was cooled to about 0-5° C., then aged at this temperature for about 1 hours.

The resulting solids were filtered, washed twice with cold methanol (18 mL), dried in a vacuum oven at 50° C., overnight, to yield the title compound as a white crystalline solid

EXAMPLE 4

{(5-Chloro-benzo[b]thiophen-3-yl)-[2-(3,4-difluoro-phenyl)-vinylcarbamoyl]-methyl}-methyl-phosphinic acid Choline Salt

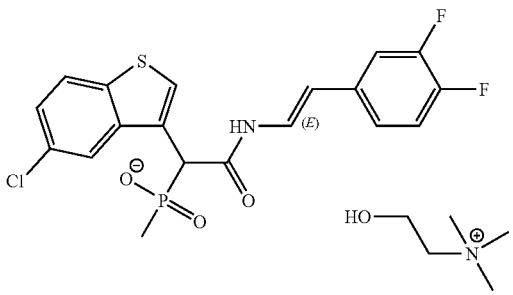

A 250 mL three-necked round-bottomed flask was charged with {(5-chloro-benzo[b]thiophen-3-yl)-[2-(3,4-difluoro-phenyl)-vinylcarbamoyl]-methyl}-methyl-phosphinic acid (20.0 g, 42.2 mol) and methanol (150 mL), under nitrogen. To the resulting slurry was then added 45% by wt. of choline hydroxide in methanol (12.8 mL, 45.3 mol), in one portion. Shortly after the addition, a homogeneous clear solution was obtained. The solution was aged at room temperature for about 1 hour, then clarified by filtration through a medium sintered glass filter. The resulting filtered solution was concentrated by distillation (at a temperature of about 63-65° C.) to a residual volume of about 55-60 mL. While at the elevated temperature, EtOAc (140-150 mL) was added by an addition funnel over a period of about 40 minutes, while maintaining a temperature of about 63-65° C. The resulting clear solution was seeded, then cooled slowly under moderate agitation to ambient temperature. The resulting slurry was then aged overnight, cooled to about 5-10° C. and aged at this temperature for about 2 hours. The resulting solid was collected by filtration, rinsed with cold EtOAc (40 mL, 2C) and dried in a vacuum oven at 50° C., overnight to yield the title compound as a white crystalline solid.

EXAMPLE 5

4-(2-Bromo-vinyl)-1,2-difluoro-benzene

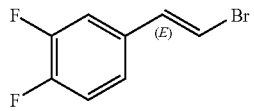

Method 1: (Adapted from the chemistry described in J. Org. Chem. 1997, 62, pp 199-200)

3,4-Difluorocinnamic acid (1.8 g, 10 mmol) was combined with acetonitrile (18.6 mL) and water (1.4 mL) and the resulting mixture treated with lithium acetate (0.12 g) and then N-bromosuccinimide (1.9 g). The resulting solution was then heated to about 70° C. and stirred at that temperature for about 2 hours. The resulting mixture was then cooled to 25° C. and quenched with 5% sodium thiosulfate solution (about 5 mL). The resulting mixture was extracted with heptane (2×30 mL) and the combined heptane layers were rinsed with water, dried over magnesium sulfate and the solvent evaporated to dryness to yield the title compound as a residue.

The $^1$H NMR was measured for a sample of the residue, which was determined to be a mixture of about 9:1 trans:cis isomers.

$^1$H NMR (CDCl$_3$): δ 7.21 (m, 3H), 6.60 (d, 1H, J=11.5 Hz), 6.39 (d, 1H, J=11.5 Hz)

EXAMPLE 6

4-(2-Bromo-vinyl)-1,2-difluoro-benzene

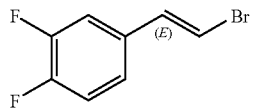

Method 2: (Adapted from the chemistry described in Synlett 2000, 10 pp 1439)

3,4-Difluorocinnamic acid (0.9 g, 5 mmol), lithium acetate (0.60 mg), N-bromosuccinimide (0.95 g), acetonitrile (9.3 mL) and water (0.7 mL) were placed in a microwave test tube and the resulting mixture was heated under microwave radiation for about 2 minutes. The resulting mixture was then cooled to ambient temperature and quenched with 5% sodium thiosulfate solution (about 2 mL). The resulting mixture was then extracted with heptane (2×10 mL), the combined organics dried over magnesium sulfate, and then concentrated under reduced pressure to yield the title compound as a residue.

The $^1$H NMR was measured for a sample of the residue, which was determined to be a mixture of about 9:1 trans:cis isomers.

$^1$H NMR (CDCl$_3$): δ 7.21 (m, 3H), 6.60 (d, 1H, J=11.5 Hz), 6.39 (d, 1H, J=11.5 Hz)

EXAMPLE 7

4-(2-Bromo-vinyl)-1,2-difluoro-benzene

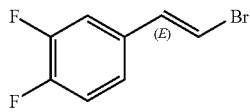

Method 3: (Adapted from the chemistry described in Tet. Lett. 1996, 37, pp 2623-2624)

3,4-Difluorocinnamic acid (1.8 g, 10 mmol) was combined with acetonitrile (8 mL0 and water (8 mL) and the resulting mixture was treated first with Mn(OAc)$_2$ hydrate (0.49 g) and then with NBS (1.9 g). The resulting mixture was then heated to about 50° C. and stirred at this temperature for about 16 hours. The resulting mixture was then cooled to about 25° C. and then quenched with 5% sodium thiosulfate solution (about 5 mL). The resulting mixture was extracted with heptane (2×30 mL) and the combined heptane layers were rinsed with water, dried over magnesium sulfate and the solvent evaporated to dryness to yield the title compound a residue.

The $^1$H NMR was measured for a sample of the residue, which was determined to be a mixture of about 20:1 trans:cis isomers.

$^1$H NMR (CDCl$_3$): δ 7.21 (m, 3H), 6.60 (d, 1H, J=11.5 Hz), 6.39 (d, 1H, J=11.5 Hz)

EXAMPLE 8

[Carbamoyl-(5-chloro-benzo[b]thiophen-3-yl)-methyl]-methyl-phosphinic acid ethyl ester

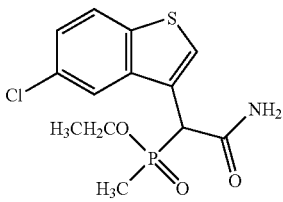

STEP A: Ethyl-1-(5-chlorobenzo[b]thiophen-3-yl)-2-oxoethyl-(methyl)-phosphinate-2-carboxylic acid To a dry 4N 3000 ml flask equipped with mechanical stirrer, nitrogen inlet, temperature probe and addition port was added ethyl (5-chlorobenzo[b]thiophen-3-yl)methyl (methyl)phosphinate (95.0 g, 329 mmol) and THF (100 mL), under nitrogen and the resulting solutin cooled to −20° C. To the resulting mixture was then added 20% 1.06M LiHMDS solution in THF (500 ml), while maintaining the temperature below 10° C. Into the resulting mixture, while maintaining the mixture temperature under 15° C., was continuously bubbled CO$_2$ until no exotherm was observed. The resulting mixture was then aged for 1 hour. Following the age, the resulting mixture was cooled to −10° C. and additional LiHMDS solution (100 ml) was added, followed by additional bubbled CO$_2$. The resulting mixture again cooled to −10° C., additional LiHMDS solution (100 ml) was added, followed by additional bubbled CO$_2$. The resulting mixture was allowed to warm to room temperature, aged at room temperature for 2 hours, then cooled to 4° C. 2N HCl was added (500 ml) slowly to maintain the cold temperature and the resulting precipitate was aged for 1 hour, at which time it was filtered and washed with water (100 mL). Filtration took approximately 1 hour. The resulting gelatinous solid was allowed to air dry for about 24 hours over which time the material slowly turned to a compact white solid. The solid was treated with 1N HCl (500 mL) and MTBE (500 mL) and the resulting slurry digested for 2 hours. The resulting easily filterable dense solid was isolated, washed with 1:1=1N HCl:MTBE (100 ml) and the solid dried for 72 hours at 50° C. under vacuum and nitrogen purge, to yield ethyl-1-(5-chlorobenzo[b]thiophen-3-yl)-2-oxoethyl (methyl)phosphinate-2-carboxylic acid as a solid.

STEP B: [Carbamoyl-(5-chloro-benzo[b]thiophen-3-yl)-methyl]-methyl-phosphinic acid ethyl ester A 2 L RBF with mechanical stirrer, addition port, temperature probe and nitrogen inlet was charged with ethyl-1-(5-chlorobenzo[b]thiophen-3-yl)-2-oxoethyl(methyl)phosphinate-2-carboxylic acid (80 g, 0.24 mole) and DMF (400 mL). To the resulting light suspension was added NaHCO$_3$ (40 g, 0.476 mole), the suspension cooled to 4° C. and 1,1'-carbonyldiimidazole (60 g, 0.37 mole) were added. The resulting mixture was aged for 1 hour while stirring, over which time off-gassing was observed to stop and the temperature observed to rise to 15° C. The resulting mixture was then cooled to 0° C. and ammonia added until no exotherm was observed. The resulting mixture was cooled to 0° C. and 5% NaHCO$_3$ (1200 mL) was added over 30 min. The resulting slurry was stirred and aged at room temperature overnight, then filtered, washed 2 times with 5% NaHCO$_3$ (500 mL) and 2 times with water (250 m). The filtercake was air dried, then slurried with ethyl acetate (400 m) overnight at room temperature. The resulting mixture was filtered and the filtercake washed with ethyl acetate (2×50 mL), then dried overnight at 45° C. to yield the title compound as a solid.

EXAMPLE 9

(5-Chloro-benzo[b]thiophen-3-yl)-(ethoxy-methyl-phosphinoyl)-acetic acid

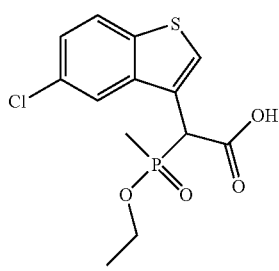

To a dry 4N 300 ml flask equipped with magnetic stirrer, nitrogen inlet, temperature probe and addition port was added ethyl (5-chlorobenzo[b]thiophen-3-yl)methyl(methyl)phosphinate (12.7, 43.99 mmol) and dry THF (15 mL) under nitrogen. The resulting solution was cooled to −20° C. To the mixture was then added a 40% (2.2 M) NaHMDS solution in THF (25 mL), maintaining the temperature below 10° C. Following the base addition, CO$_2$ was bubbled cautiously until no exotherm was observed, while maintaining the temperature of the reaction mixture below 15° C. The resulting mixture was then degassed with nitrogen and NaHMDS (10 mL) was added, followed by additional CO$_2$ bubbling. The addition of NaHMDS ad CO$_2$ was repeated 3 more times. The resulting solution was cooled to 0° C. and MTBE (80 mL) was added. To the resulting mixture was then added, slowly, 2N HCl (20 mL), followed by 6N HCl (40 mL), at which point the pH of the mixture was measured to be about 2. Throughout the addition of the acid, the temperature of the mixture was maintained between 0 and 15° C. Initial precipitation was observed upon acidification, while on completion of the acid addition, the mixture resolved in two clear layers. The layers were split, and the organic layer evaporated to yield an oil. The oil was digested overnight with MTBE (20 mL) to yield the title compound as a filterable solid.

EXAMPLE 10

[Carbamoyl-(5-chloro-benzo[b]thiophen-3-yl)-methyl]-methyl-phosphinic acid ethyl ester

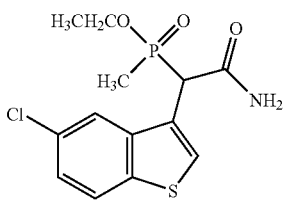

(5-Chloro-benzo[b]thiophen-3-yl)-(ethoxy-methyl-phosphinoyl)-acetic acid (9.0 g, 0.027 mol) was suspended in THF (250 mL), TEA (4.46 mL, 0.032 mol), and isobutylchloroformate (3.5 mL, 0.0027 mol) were slowly added and the resulting suspension cooled to −5° C. The resulting mixture was stirred for 1 hour at −2° C. and then ammonium acetate (2.1 g, 0.027 mol) was added in two portions. The cooling ice bath was then roomed and the resulting mixture was left overnight. To the resulting mixture was then added THF (100 mL) and additional isobutylchloroformate (0.5 ml) and the resulting mixture stirred for 30 minutes. To the resulting mixture was then added ammonium acetate (3.8 mmol) and the resulting mixture again stirred for 30 minutes.

To the resulting mixture was then added water (200 mL). Most of the THF was then evaporated and ethyl acetate (250 mL) added. To the resulting mixture was then added water (100 mL; for a total water amount of 300 mL) and ethyl acetate (150 mL; for a total ethyl acetate amount of 400 mL). The resulting mixture was heated to 40° C., the resulting layers were separated. The organic layer was washed with NaOH (0.1%, 200 mL) and brine (200 mL). The solvent was removed by evaporation to dryness to yield the title compound as a residue, as a white solid.

To the white solid was added acetonitrile (300 mL) and the resulting mixture heated on a steam bath to dissolve the solid. The heated mixture was then polish filtered through filter paper. The crystallized title compound was then isolated as a white solid.

The procedure described in Example 11 below represents a recipe for the preparation of the title compound. The recipe/procedure was applied to the preparation of 4 individual batches of the title compound.

EXAMPLE 11

{(5-Chloro-benzo[b]thiophen-3-yl)-[2-(3,4-difluorophenyl)-vinylcarbamoyl]-methyl}-methyl-phosphinic acid ethyl ester

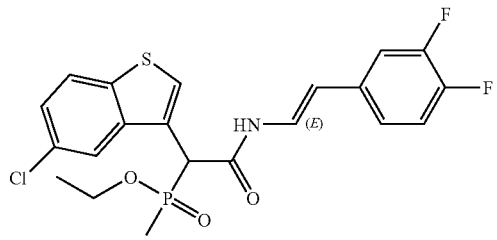

[Carbamoyl-(5-chloro-benzo[b]thiophen-3-yl)-methyl]-methyl-phosphinic acid ethyl ester (60.0 g, 181 mmol) was placed in a reactor under nitrogen, followed by addition of cesium carbonate (35.3 g, 108 mmol) and copper iodide (6.90 g, 36.2 mmol) and the resulting mixture was stirred at ambient temperature. DMA (123 g) and N,N'-dimethylethylenediame (6.36 g, 72.1 mmol) (with the addition flask washed with DMA (30 g)) were added and the resulting mixture heated to 70-75° C. with about 30-60 minutes, over which time a thin blue suspension was observed to form. To the resulting mixture was then added 4-(2-bromo-vinyl)-1,2-difluoro-benzene (47.6 g, 217 mmol) over about 10-30 minutes (with the addition flask washed with DMA (30 g)), then stirred for 5 to 7 hours at 75-85° C., with the progress of the reaction monitored by HPLC. When the reaction was deemed complete, the reaction mixture was cooled to 60-78° C., ethyl acetate (345 g) was added followed by addition of water (303 g), and the mixture stirred for 10-30 minutes. The resulting phases were separated. To the organic phase was added a solution of NaCl (30 g in 270 g H$_2$O), followed by stirring for 10-30 min at a temperature of 55-65° C. The resulting phases were separated, to the organic phase was added again a solution of NaCl (30 g in 270 g H$_2$O), followed by stirring for 10-30 min at a temperature of 55-65° C. The resulting phases were separated and treated a third time with addition of a solution of NaCl (30 g in 270 g H$_2$O), followed by stirring for 10-30 min at a temperature of 55-65° C. The resulting phases were separated, the organic phase heated to distill off 107-139 g of solvent (at 50-65° C.). To the resulting residue, cyclohexane (280 g) was added over 20-40 minutes and the resulting mixture cooled to 10-15° C., then stirred at this temperature for 2-3 hours, over which time a thick suspension was observed to form. The resulting suspension was filtered, the filtercake washed with a mixture of cyclohexane (135 g) and ethyl acetate (45 g), then dried at 55-60° C., under vacuum to yield the title compound as a solid.

EXAMPLE 12

Oral Formulation—Prophetic Example

As a specific embodiment of an oral composition, 100 mg of the compound prepared as in Example 1, 2, 3 or 4 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A process for the preparation of a compound of formula (I)

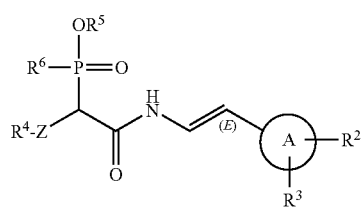

wherein

is independently selected from the group consisting of aryl, heteroaryl, and benzo fused heterocyclyl; optionally substituted with $R^2$ and $R^3$;

$R^2$ is one to three substituents independently selected from the group consisting of $C_{1-4}$alkyl, methoxy, $C_{2-6}$alkoxy, NH$_2$, NH($C_{1-6}$alkyl), —N($C_{1-6}$)dialkyl, aryl, heteroaryl, halogen, hydroxy, and nitro;

wherein the $C_{1-4}$alkyl and $C_{2-6}$ alkoxy substituents of $R^2$ are optionally substituted with a substituent independently selected from the group consisting of —NR$^{11}$R$^{12}$, aryl, heteroaryl, one to three halogens and hydroxy; wherein $R^{11}$ and $R^{12}$ are substituents independently selected from the group consisting of hydrogen, $C_{1-6}$ alkyl, and aryl; wherein the $C_{1-6}$alkyl substituent of $R^{11}$ or $R^{12}$ is optionally substituted with a substituent selected from the group consisting of hydroxy, aryl, —C(=O)C$_{1-4}$alkoxy, and —NR$^{15}$R$^{16}$;

wherein said $R^{15}$ and $R^{16}$ are substituents independently selected from the group consisting of hydrogen, $C_{1-6}$ alkyl, and aryl, alternatively, $R^{15}$ and $R^{16}$ are taken together with the atoms to which they are attached to form a ring of five to seven members;

$R^3$ is one to three substituents independently selected from the group consisting of $C_{1-6}$alkyl, $C_{2-6}$alkenyl, $C_{1-6}$alkoxy, —OCH$_2$(C$_{2-6}$)alkenyl, NH$_2$, —NH($C_{1-6}$alkyl), —N($C_{1-6}$)dialkyl, —NHC(=O)Cy, —N($C_{1-6}$alkyl)C(=O)Cy, —C(=O)C$_{1-4}$alkoxy, —C(=O)NR$^{17}$R$^{18}$, —C(=O)NHcycloalkyl, —C(=O)N($C_{1-6}$alkyl)cycloalkyl, —C(=O)NHCy, —C(=O)N($C_{1-6}$alkyl)Cy, —C(=O)Cy, —OC(=O)NR$^{19}$R$^{20}$, halogen, hydroxy, nitro, cyano, aryl, and aryloxy;

wherein alkyl and alkoxy are optionally substituted with one to three substituents independently selected from the group consisting of —NR$^{21}$R$^{22}$, —NHcycloalkyl, —N($C_{1-6}$alkyl)cycloalkyl, —NHCy, —N($C_{1-6}$alkyl)Cy, aryl, heteroaryl, halogen, —C(=O)NR$^{23}$R$^{24}$, —OC(=O)NR$^{25}$R$^{26}$, —C(=O)(C$_{1-4}$)alkoxy, and —C(=O)Cy; wherein alkenyl is optionally substituted on a terminal carbon with aryl and —C(=O)NR$^{27}$R$^{28}$; and, wherein aryl and cycloalkyl are optionally substituted with one to three substituents independently selected from $R^{14}$;

each $R^{14}$ is independently hydrogen, $C_{1-6}$alkyl, $C_{1-6}$alkoxy, $C_{2-6}$alkenyl, $C_{1-6}$alkylthio, —$NH_2$, —NH($C_{1-6}$)alkyl, —N($C_{1-6}$)dialkyl, aryl, heteroaryl, aryloxy, heteroaryloxy, halogen, hydroxy, or nitro; wherein any one of the foregoing $C_{1-6}$alkyl- or $C_{1-6}$alkoxy-containing substituents of $R^{14}$ is optionally substituted on a terminal carbon atom with a substituent selected from —$NR^{29}R^{30}$, aryl, heteroaryl, one to three halogen atoms, or hydroxy;

$R^{17}$, $R^{18}$, $R^{19}$, $R^{20}$, $R^{21}$, $R^{22}$, $R^{23}$, $R^{24}$, $R^{25}$ and $R^{26}$ are substituents independently selected from the group consisting of hydrogen, $C_{1-6}$alkyl and aryl; wherein the $C_{1-6}$alkyl and aryl are each optionally substituted with hydroxy, aryl, aryloxy, —C(=O)-aryl, —C(=O)$C_{1-4}$alkoxy, $NH_2$, —NH($C_{1-6}$alkyl), or —N($C_{1-6}$)dialkyl; alternatively, $R^{17}$ and $R^{18}$, $R^{19}$ and $R^{20}$, $R^{21}$ and $R^{22}$, $R^{23}$ and $R^{24}$ or $R^{25}$ and $R^{26}$ are taken together with the atoms to which they are attached to form a ring of five to seven members;

$R^{27}$ and $R^{28}$ are independently hydrogen; $C_{1-6}$alkyl optionally substituted with hydroxy, aryl, —C(=O)$C_{1-4}$alkoxy, $NH_2$, —NH($C_{1-6}$alkyl) or —N($C_{1-6}$)dialkyl; or aryl; alternatively, $R^{27}$ and $R^{28}$ are taken together with the atoms to which they are attached to form a ring of five to seven members;

$R^{29}$ and $R^{30}$ are independently hydrogen, $C_{1-6}$alkyl optionally substituted with hydroxy, aryl, —C(=O)$C_{1-4}$alkoxy, $NH_2$, —NH($C_{1-6}$alkyl), or —N($C_{1-6}$)dialkyl; or aryl; alternatively, $R^{29}$ and $R^{30}$ are taken together with the atoms to which they are attached to form a ring of five to seven members;

Cy is a heterocyclyl optionally substituted with a substituent selected from the group consisting of $C_{1-6}$ alkyl, $C_{1-6}$alkyl(=O)$C_{1-6}$alkyl, —$C_{1-6}$alkylC(=O)$C_{1-6}$alkoxy, $C_{1-6}$alkylC(=O)aryl, —C(=O)($C_{1-6}$)alkyl, —C(=O)($C_{1-6}$)alkoxy, —C(=O)aryl, —$SO_2$aryl, aryl, heteroaryl, and heterocyclyl; wherein aryl and the aryl portion of the $C_{1-6}$alkylC(=O)aryl, —C(=O)aryl and —$SO_2$aryl are optionally substituted with one to three substituents independently selected from the group consisting of $C_{1-6}$alkyl, $C_{1-6}$alkoxy, halogen, hydroxy, $NH_2$, NH($C_{1-6}$alkyl), or —N($C_{1-6}$)dialkyl; and wherein heterocyclyl is optionally substituted with aryl, one to three halogen atoms, or one to three oxo substituents; and, wherein heterocyclyl is optionally spiro-fused to said Cy;

$R^5$ is selected from the group consisting of hydrogen; $C_{1-3}$alkyl optionally substituted with $NH_2$, —NH($C_{1-6}$)alkyl, —N($C_{1-6}$)dialkyl, $C_{1-6}$alkylcarbonyloxy, $C_{1-6}$alkoxycarbonyloxy, $C_{1-6}$alkylcarbonylthio, ($C_{1-6}$)alkylaminocarbonyl, di($C_{1-6}$)alkylaminocarbonyl, one to three halogens, or hydroxy;

and aryl optionally substituted with $C_{1-6}$alkyl, $C_{1-6}$alkoxy, $C_{1-6}$alkylthio, $C_{2-6}$ alkenyl, —$NH_2$, —NH($C_{1-6}$)alkyl, —N($C_{1-6}$)dialkyl, aryl, heteroaryl, aryloxy, heteroaryloxy, halogen, hydroxy, or nitro;

alternatively, when $R^6$ is $C_{1-8}$alkoxy, $R^5$ and $R^6$ are taken together with the atoms to which they are attached to form a 5-8 membered monocyclic ring;

and provided that $R^5$ is other than $C_{1-3}$alkyl substituted with di($C_{1-6}$)alkylamino-carbonyl when ring system A is 3,4-difluoro-phenyl, $R^6$ is OH, and Z—$R^4$ is 5-chloro-benzothiophen-3-yl; and provided that $R^5$ is other than $C_{1-3}$alkyl substituted with $C_{1-6}$alkylcarbonylthio when ring system A is 3,4-difluoro-phenyl, $R^6$ is $CH_3$, and Z—$R^4$ is 5-chloro-benzothiophen-3-yl;

$R^6$ is selected from the group consisting of $C_{1-6}$alkyl, $C_{1-8}$alkoxy, heteroaryl, aryl, and hydroxy; wherein alkyl and $C_{1-8}$alkoxy are optionally substituted on a terminal carbon atom with a substituent selected from $C_{1-3}$alkoxy, aryl, or hydroxy; and alkoxy is optionally substituted on a terminal carbon with a substituent independently selected from the group consisting of $C_{1-6}$alkylcarbonyloxy, and di($C_{1-6}$)alkylaminocarbonyl; and wherein heteroaryl and aryl are optionally substituted with one to three substituents independently selected from the group consisting of aryl, hydroxy, $C_{1-6}$alkoxy, and halogen;

Z is a bicyclic aryl or bicyclic heteroaryl;

$R^4$ is one to three substituents selected from the group consisting of H, $C_{1-6}$alkyl, $C_{1-6}$alkenyl, $C_{1-6}$alkoxy, aryl ($C_{2-6}$)alkenyl, halogen, —C(=O)Cy, —C(=O)$NR^{31}R^{32}$, aryl, —$CO_2$H, oxo, and cyano; wherein the alkyl and alkoxy are optionally substituted with a substituent independently selected from the group consisting of —$NR^{33}R^{34}$, aryl, one to three halogen atoms, and hydroxy; wherein the aryl is optionally substituted with a substituent independently selected from the group consisting of hydrogen, $C_{1-6}$alkyl, $C_{1-6}$alkoxy, aryl, halogen, hydroxy, and nitro;

wherein said $R^{31}$, $R^{32}$, $R^{33}$, and $R^{34}$ are substituents independently selected from the group consisting of hydrogen, $C_{1-6}$ alkyl, and aryl, wherein alkyl is optionally substituted with hydroxy, aryl, —C(=O)$C_{1-4}$alkoxy, $NH_2$, NH($C_{1-6}$alkyl), or —N($C_{1-6}$)dialkyl; or $R^{31}$ with $R^{32}$, or $R^{33}$ with $R^{34}$ are optionally taken together with the atoms to which they are attached to form a ring of five to seven members;

or a pharmaceutically acceptable salt thereof; comprising the steps of

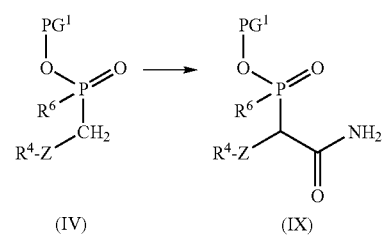

(a) reacting a compound of formula (IV), wherein $PG^1$ is an oxygen protecting group; with a source of nitrogen; in the presence of $CO_2$ gas; in an organic solvent; to yield the corresponding compound of formula (IX);

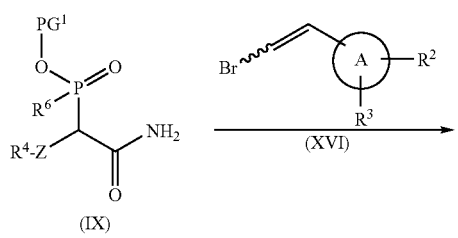

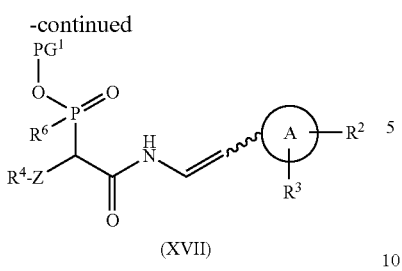

(XVII)

(b) reacting the compound of formula (IX) with a compound of formula (XVI); in the presence of CuI; in the presence of an inorganic base; in the presence of a ligand; in an organic solvent or mixture thereof; to yield the corresponding compound of formula (XVII);

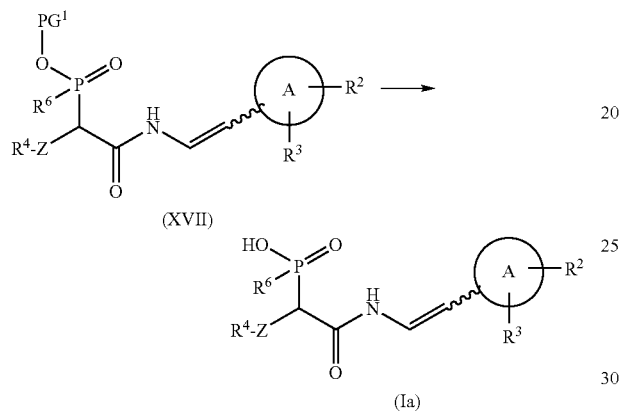

(c) de-protecting the compound of formula (XVII); to yield the corresponding compound of formula (Ia); and

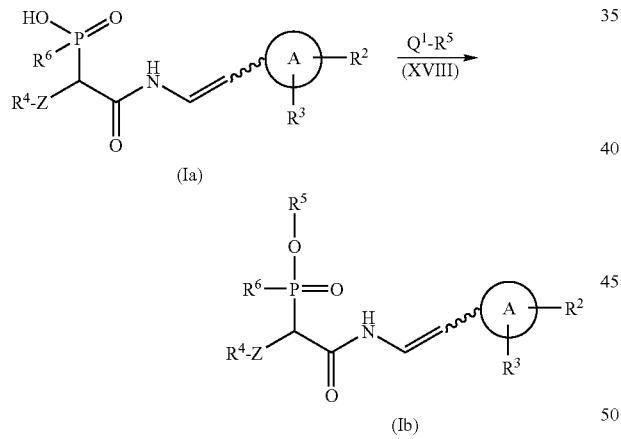

(d) optionally reacting the compound of formula (Ia) with a compound of formula (XVIII), wherein $Q^1$ is a leaving group and wherein $R^5$ is other than hydrogen; in the presence of an organic base; in an organic solvent; to yield the corresponding compound of formula (Ib), wherein $R^5$ is other than hydrogen.

2. A process as in claim 1, wherein

is selected from the group consisting of 3,4-difluorophenyl and 3,5-dichlorophenyl; $R^5$ is selected from the group consisting of hydrogen; —$CH_2$—O—C(O)—C($CH_3$)$_3$, and —$CH_2$—OC(O)O—$CH_3$)$_2$; $R^6$ is selected from the group consisting of methyl and hydroxy; and $R^4$—Z is 5-chlorobenzo[b]thiophen-3-yl.

3. A process for the preparation of a compound of formula (I-A)

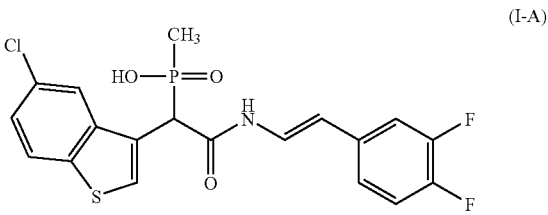

or a pharmaceutically acceptable salt thereof; comprising the steps of

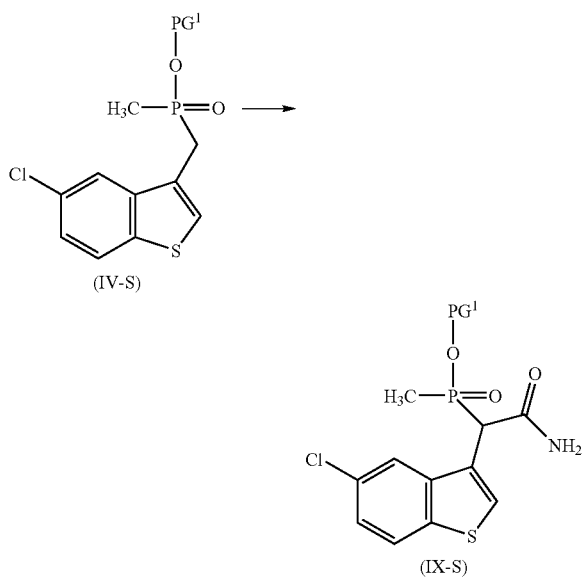

(a) reacting a compound of formula (IV-S) wherein $PG^1$ is an oxygen protecting group with a source of nitrogen, in the presence of $CO_2$ gas, in an organic solvent; to yield the corresponding compound of formula (IX-S);

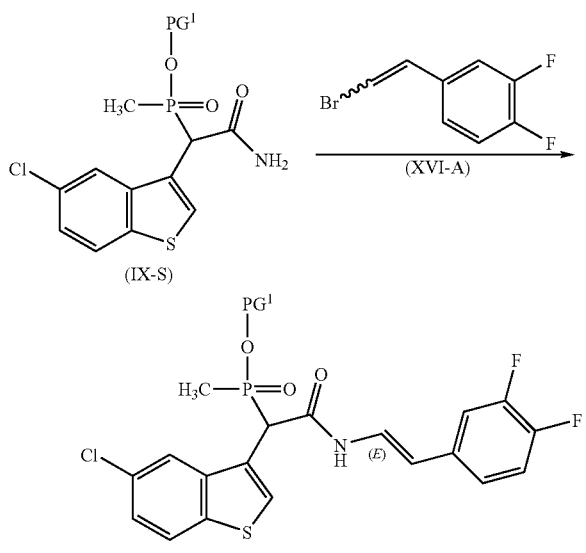

(b) reacting the compound of formula (IX-S) with a compound of formula (XVI-A); in the presence of CuI; in the presence of an inorganic base; in the presence of a ligand; in an organic solvent; to yield the corresponding compound of formula (XVII-A); and

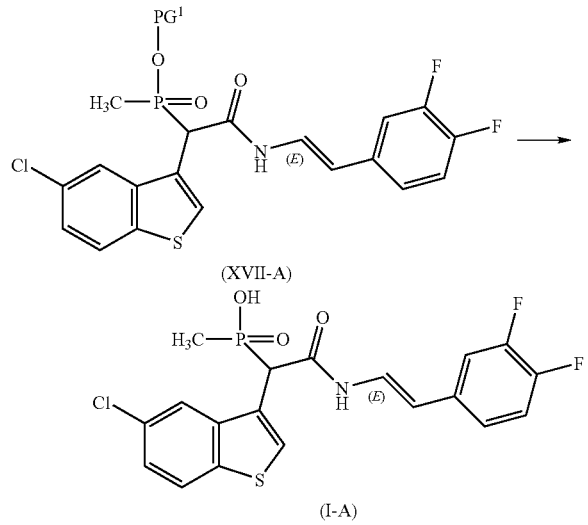

(c) de-protecting the compound of formula (XVII-A); to yield the corresponding compound of formula (I-A).

4. A process as in claim 3, wherein the $PG^1$ is ethyl.

5. A process as in claim 3, wherein the source of nitrogen is LiHMDS and wherein the source of nitrogen is present in an amount in the range of from about 3.0 to about 6.0 molar equivalents.

6. A process as in claim 3, wherein the $CO_2$ is bubbled in an excess amount.

7. A process as in claim 3, wherein the compound of formula (IV-S) is reacted with the source of nitrogen at a temperature in the range of from about 0° C. to about 20° C.

8. A process as in claim 3, wherein the compound of formula (XVI-A) is present in an excess of its corresponding trans orientation; and wherein the compound of formula (XVI-A) is present in an amount in the range of from about 1.0 to about 2.0 molar equivalents.

9. A process as in claim 3, wherein the CuI is present in an amount in the range of from about 0.1 to about 0.5 molar equivalents.

10. A process as in claim 3, wherein the inorganic base in step (b) is $Cs_2CO_3$ and wherein the $Cs_2CO_3$ is present in an amount in the range of from about 0.5 to about 3.0 molar equivalents.

11. A process as in claim 3, wherein the ligand in step (b) is N,N-dimethylethylenediamine, and wheren the ligand is present in an amount in the range of from about 0.2 to about 2.0 molar equivalents.

12. A process as in claim 3, wherein the compound of formula (IX-S) is reacted with the compound of formula (XVI-A) at a temperature in the range of from about 50° C. to about 100° C.

13. A process as in claim 3, wherein the compound of formula (IX-S) is reacted with the compound of formula (XVI-A) under an inert atmosphere.

14. A process as in claim 3, wherein in step (b) a mixture of the compound of formula (IX-S), the CuI, the ligand, the inorganic base and the organic solvent is heated to a temperature in the range of from about 50° C. to about 100° C., prior to addition of the compound of formula (XVI-A).

15. A process as in claim 3, wherein the organic solvent in step (a) is THF and wherein the organic solvent in step (b) is DMA.

16. A process for the preparation of a compound of formula (IX)

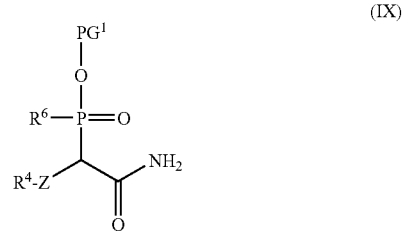

wherein
$PG^1$ is an oxygen protecting group;
$R^6$ is selected from the group consisting of $C_{1-6}$alkyl, $C_{1-8}$alkoxy, heteroaryl, aryl, and hydroxy; wherein alkyl and $C_{1-8}$alkoxy are optionally substituted on a terminal carbon atom with a substituent selected from $C_{1-3}$alkoxy, aryl, or hydroxy; and alkoxy is optionally substituted on a terminal carbon with a substituent independently selected from the group consisting of $C_{1-6}$alkylcarbonyloxy, and di($C_{1-6}$)alkylaminocarbonyl; and wherein heteroaryl and aryl are optionally substituted with one to three substituents independently selected from the group consisting of aryl, hydroxy, $C_{1-6}$alkoxy, and halogen;
Z is a bicyclic aryl or bicyclic heteroaryl;
$R^4$ is one to three substituents selected from the group consisting of H, $C_{1-6}$alkyl, $C_{1-6}$alkenyl, $C_{1-6}$alkoxy, aryl $(C_{2-6})$alkenyl, halogen, —C(=O)Cy, —C(=O)$NR^{31}R^{32}$, aryl, —$CO_2H$, oxo, and cyano; wherein the alkyl and alkoxy are optionally substituted with a substituent independently selected from the group consisting of —$NR^{33}R^{34}$, aryl, one to three halogen atoms, and hydroxy; wherein the aryl is optionally substituted with a substituent independently selected from the group consisting of hydrogen, $C_{1-6}$alkyl, $C_{1-6}$alkoxy, aryl, halogen, hydroxy, and nitro;
wherein said $R^{31}$, $R^{32}$, $R^{33}$, and $R^{34}$ are substituents independently selected from the group consisting of hydrogen, $C_{1-6}$ alkyl, and aryl, wherein alkyl is optionally substituted with hydroxy, aryl, —C(=O)$C_{1-4}$alkoxy, $NH_2$, NH($C_{1-6}$alkyl), or —N($C_{1-6}$)dialkyl; or $R^{31}$ with $R^{32}$, or $R^{33}$ with $R^{34}$ are optionally taken together with the atoms to which they are attached to form a ring of five to seven members;
or a pharmaceutically acceptable salt thereof; comprising the step of

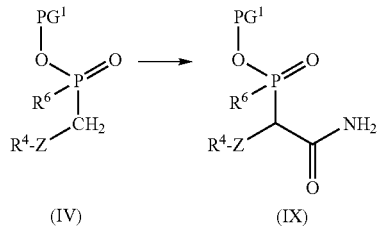

(A) reacting a compound of formula (iv) with a source of nitrogen; in the presence of $CO_2$ gas; in an organic solvent; to yield the corresponding compound of formula (IX).

17. process as in claim 16, wherein $PG^1$ is ethyl, $R^6$ is selected from the group consisting of methyl and hydroxy, and $R^4$—Z IS 5-chloro-benzo[B] thiophen-3-yl.

18. a process for the preparation of a compound of formula (IX-S)

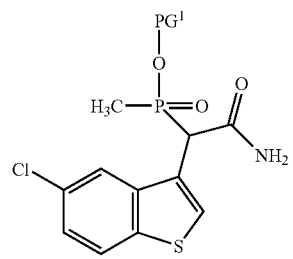
(IX-S)

comprising

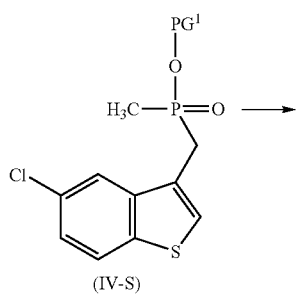
(IV-S)

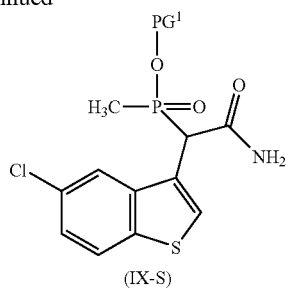
(IX-S)

(a) reacting a compound of formula (IV-S) wherein $PG^1$ is an oxygen protecting group with a source of nitrogen, in the presence of $CO_2$ gas, in an organic solvent; to yield the corresponding compound of formula (IX-S).

19. A process as in claim 18 wherein $PG^1$ is ethyl; wherein the source of nitrogen is LiHMDS;

wherein the source of nitrogen is present in an amount in the range of from about 3.0 to about 6.0 molar equivalents; and wherein the $CO_2$ gas is bubbled in an excess amount.

* * * * *